(12) United States Patent
Kirschenman et al.

(10) Patent No.: US 8,343,096 B2
(45) Date of Patent: Jan. 1, 2013

(54) ROBOTIC CATHETER SYSTEM

(75) Inventors: Mark B. Kirschenman, Waverly, MN (US); John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 822 days.

(21) Appl. No.: 12/347,811

(22) Filed: Dec. 31, 2008

(65) Prior Publication Data
US 2009/0247993 A1 Oct. 1, 2009

Related U.S. Application Data

(60) Provisional application No. 61/040,143, filed on Mar. 27, 2008, provisional application No. 61/099,904, filed on Sep. 24, 2008.

(51) Int. Cl.
*A61M 31/00* (2006.01)

(52) U.S. Cl. .................................. 604/95.04

(58) Field of Classification Search ............... 604/95.04, 604/264, 95.05, 22; 606/41, 130; 600/141, 600/145; 424/422; 318/568.11; 607/122
See application file for complete search history.

(56) References Cited

U.S. PATENT DOCUMENTS

| | | |
|---|---|---|
| 4,802,487 A | 2/1989 | Martin et al. |
| 4,884,557 A | 12/1989 | Takehana et al. |
| 5,170,817 A | 12/1992 | Sunderland |
| 5,441,483 A | 8/1995 | Avitall |
| 5,545,200 A | 8/1996 | West et al. |
| 5,579,442 A | 11/1996 | Kimoto et al. |
| 5,630,783 A | 5/1997 | Steinberg |
| 5,706,827 A | 1/1998 | Ehr et al. |
| 5,807,377 A | 9/1998 | Madhani et al. |
| 6,348,911 B1 | 2/2002 | Rosenberg et al. |
| 6,396,232 B2 | 5/2002 | Haanpaa et al. |
| 6,709,667 B1 | 3/2004 | Lowe et al. |
| 6,850,252 B1 | 2/2005 | Hoffberg |
| 6,869,390 B2 | 3/2005 | Elliott et al. |
| 6,869,396 B2 | 3/2005 | Belson |
| 7,199,790 B2 | 4/2007 | Rosenberg et al. |
| 7,276,044 B2 | 10/2007 | Ferry et al. |
| 2005/0075538 A1 | 4/2005 | Banik et al. |
| 2006/0293643 A1 | 12/2006 | Wallace et al. |

(Continued)

FOREIGN PATENT DOCUMENTS

WO WO2008/101228 8/2008

(Continued)

OTHER PUBLICATIONS

"International Search Report & Written Opinion", PCT/US2009/069712 Feb. 25, 2010.

(Continued)

*Primary Examiner* — Nicholas Lucchesi
*Assistant Examiner* — Brooke Matney
(74) *Attorney, Agent, or Firm* — Dykema Gossett PLLC

(57) ABSTRACT

A robotic catheter system including one or more robotic catheter manipulator assemblies supported on a manipulator support structure. The robotic catheter manipulator assembly may include one or more removably mounted robotic catheter device cartridges and robotic sheath device cartridges, with each cartridge being generally linearly movable relative to the robotic catheter manipulator assembly. An input control system may be provided for controlling operation of the robotic catheter manipulator assembly. A visualization system may include one or more display monitors for displaying a position of a catheter and/or a sheath respectively attached to the robotic catheter and sheath device cartridges.

51 Claims, 45 Drawing Sheets

U.S. PATENT DOCUMENTS

| | | |
|---|---|---|
| 2007/0142726 A1 | 6/2007 | Carney et al. |
| 2007/0185486 A1 | 8/2007 | Hauck et al. |
| 2007/0198008 A1 | 8/2007 | Hauck et al. |
| 2007/0233044 A1 | 10/2007 | Wallace et al. |
| 2008/0009791 A1 | 1/2008 | Cohen et al. |
| 2008/0013809 A1 | 1/2008 | Zhu et al. |
| 2008/0312536 A1 | 12/2008 | Dala-Krishna |
| 2009/0033623 A1 | 2/2009 | Lin |
| 2009/0247993 A1 | 10/2009 | Kirschenman et al. |
| 2009/0322697 A1 | 12/2009 | Cao |

FOREIGN PATENT DOCUMENTS

| | | |
|---|---|---|
| WO | WO-2009/120992 | 10/2009 |

OTHER PUBLICATIONS

Bressler, James E. et al., "Cartridge for vascular device", US2006-0155321 Jul. 13, 2006.

Brock, David L. et al., "Flexible Instrument", US2002-0087048 A1 Jul. 4, 2002.

Cohen, Todd J. et al., "Remotely controlled catheter insertion system", US2008-0009791 Jan. 10, 2008.

Falwell, Gary S. et al., "Electrophysiology catheter for mapping and/or ablation", US2004-0193239 Sep. 30, 2004.

Govari, Assaf et al., "Robotically guided catheter", US2005-0203382 A1 Sep. 15, 2005 , Y p. 2, 3, 15 and 19.

Kang, Hyosig et al., "Method and apparatus for controlling a haptic device", US2007-0270685 Nov. 22, 2007.

Mansouri-Ruiz, Idriss , "Automatic/manual longitudinal position translator and rotary drive system for catheters", US2002-0072704 A1 Jun. 13, 2002.

Massey, Joe B. et al., "Medical device introduction systems and methods", WO 2007-146325 A2 Dec. 21, 2007.

Moll, Frederic H. at al., "Robotic catheter system and methods", US2007-0197896 Aug. 23, 2007.

Moll, Frederic H. et al., "Robotic Catheter System and methods", US2007-0043338 Feb. 22, 2007.

Morales, Ruiz , "Robotic surgical system for performing minimally invasive medical procedures", WO 2007-088208 Aug. 9, 2007.

Rosenberg, Louis B. et al., "Haptic Feedback Device", US2007-0298877 Dec. 27, 2007.

Rosenberg, Craig R. et al., "Robotic Catheter system", US2006-0276775 Dec. 7, 2006 , Entire document.

Thompson, Russell B. et al., "Assemblies for creating compound curves in distal catheter regions", US2002-0068868 Jun. 6, 2002.

Wallace, Daniel T. , "Apparatus for measuring distal forces on a working instrument", US2007-0233044 A1 Oct. 4, 2007.

Wallace, Daniel T. et al., "Method of sensing forces on a working instrument", US2007-0197939 A1 Aug. 23, 2007.

Werneth, Randell L. et al., "Ablation Catheter", US2006-0089637 Apr. 27, 2006.

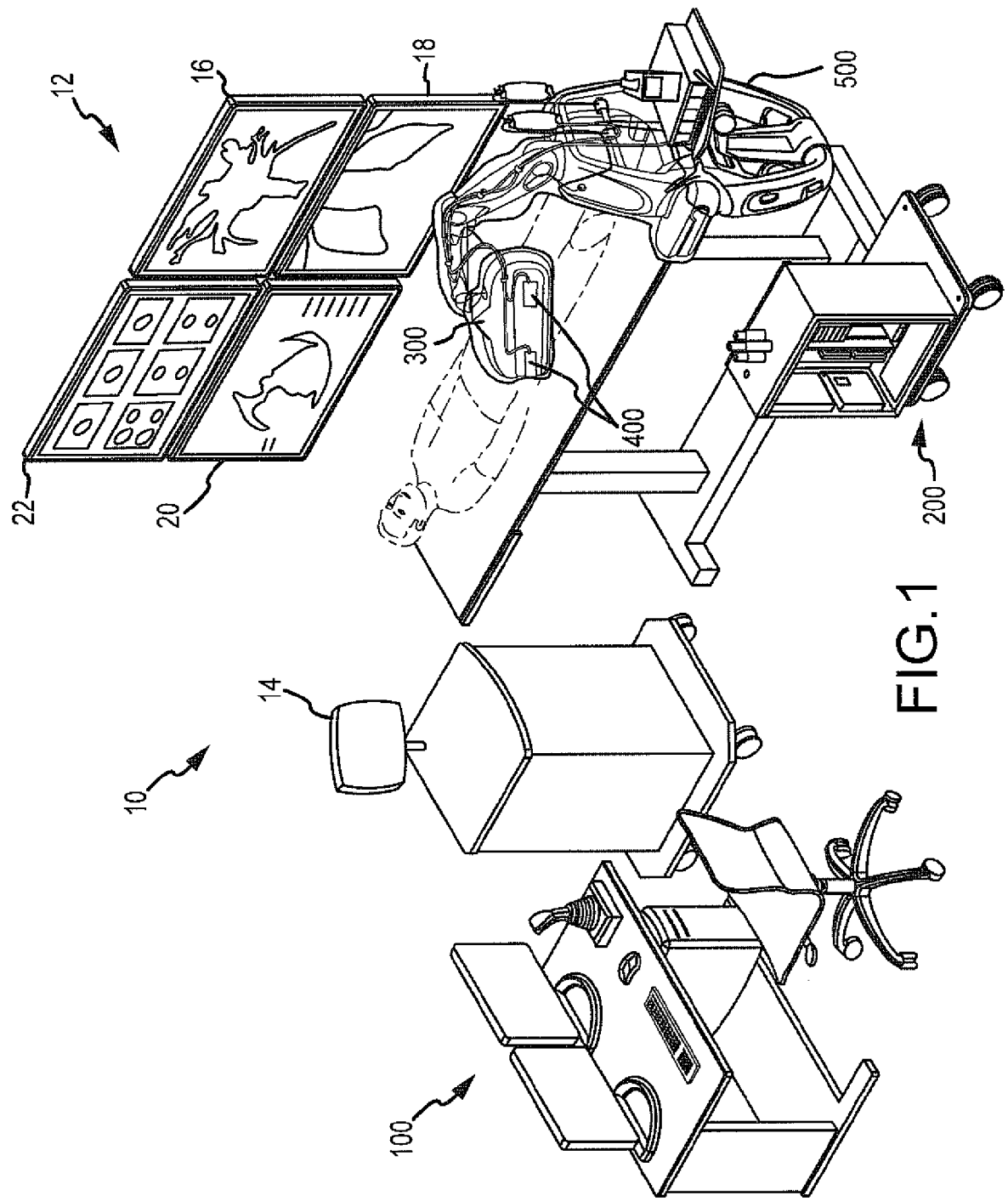

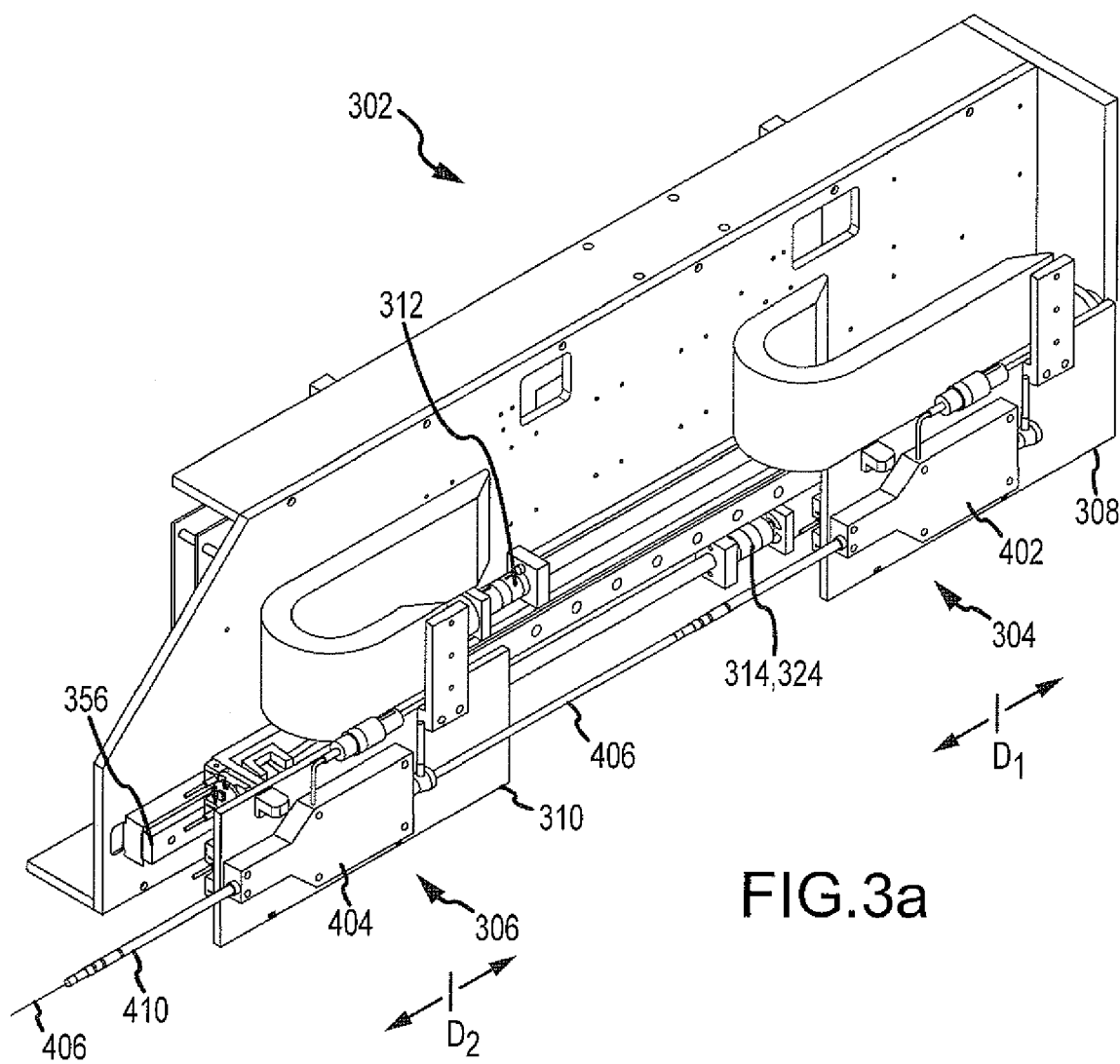
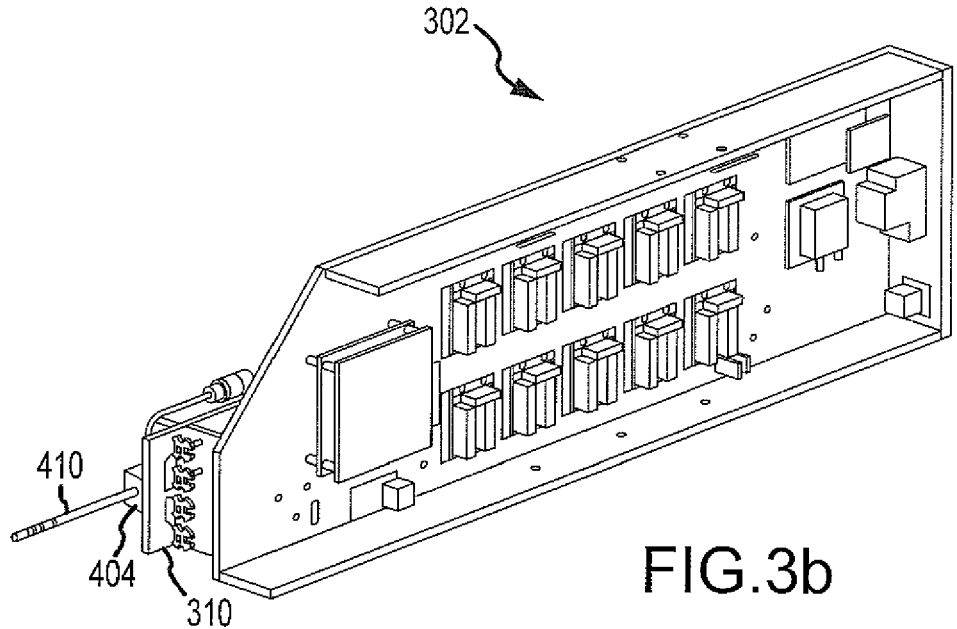

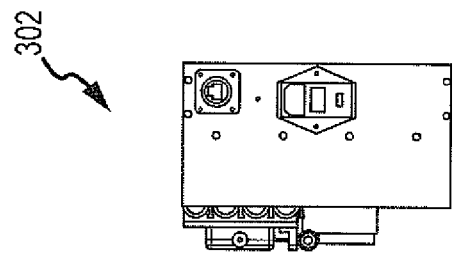
FIG. 3e
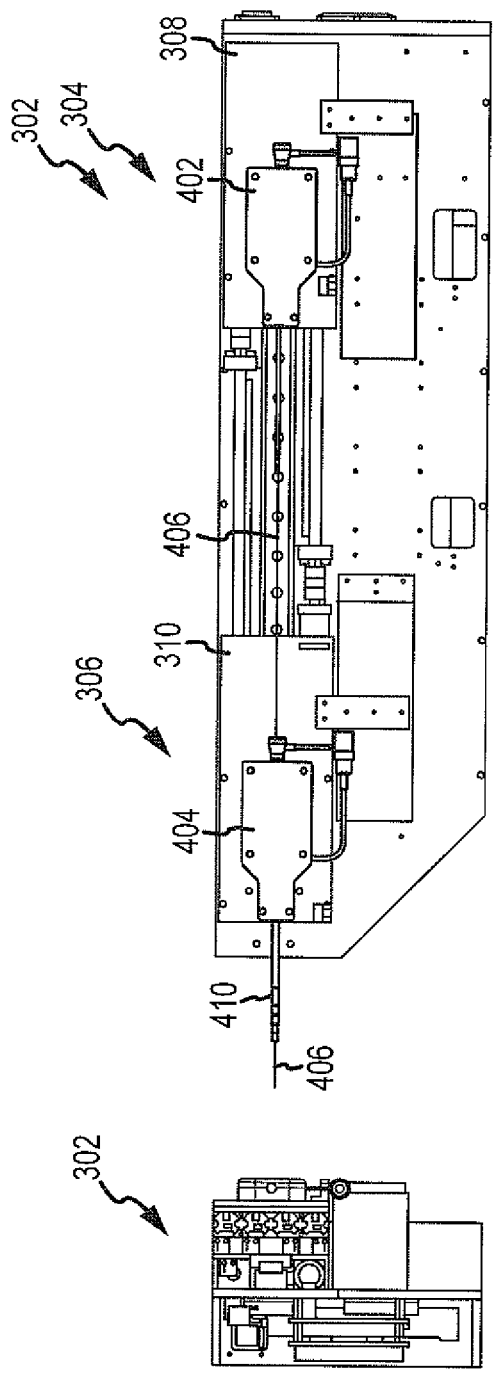
FIG. 3f
FIG. 3d
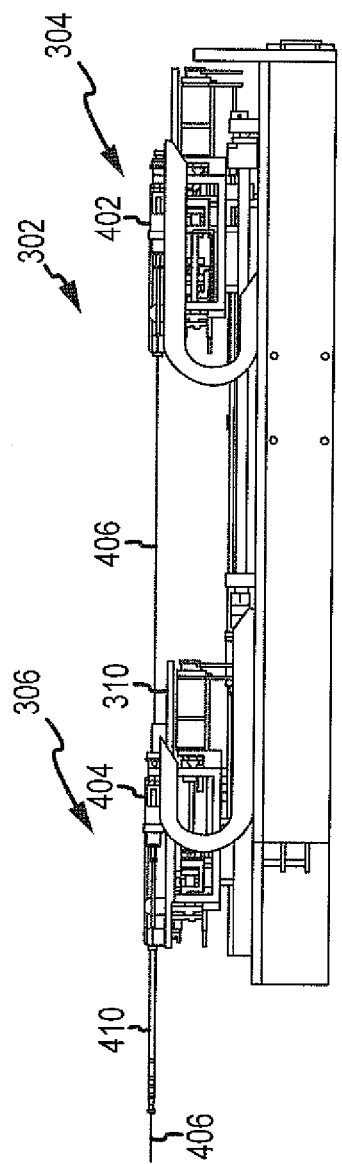
FIG. 3g

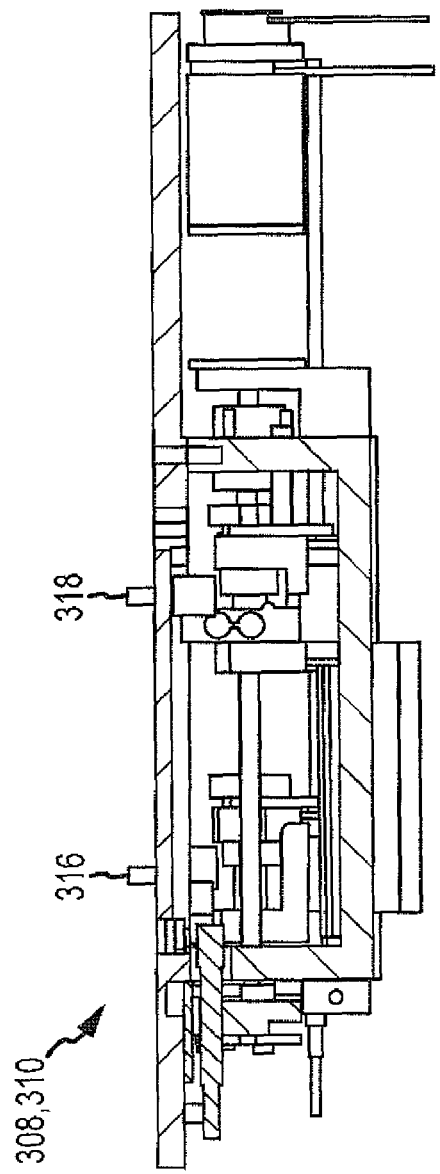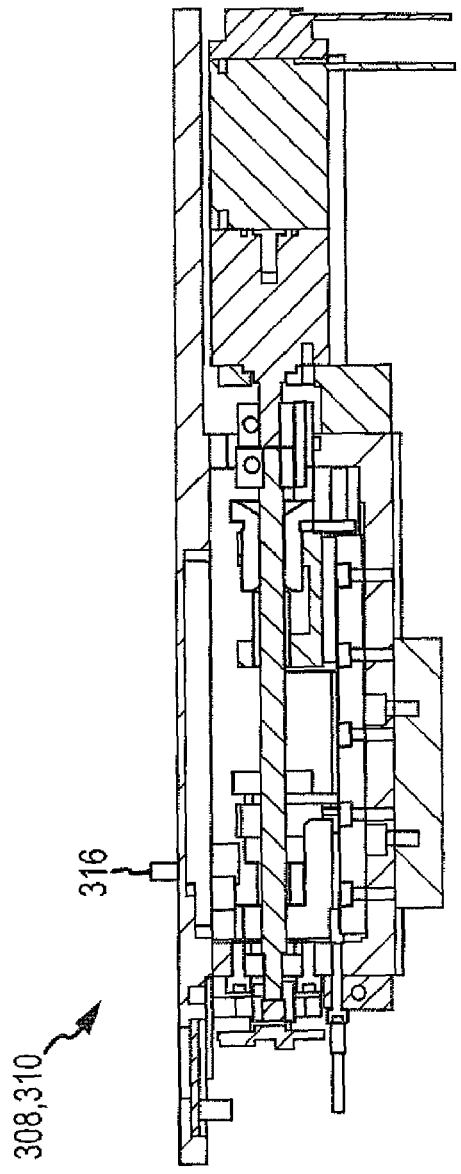

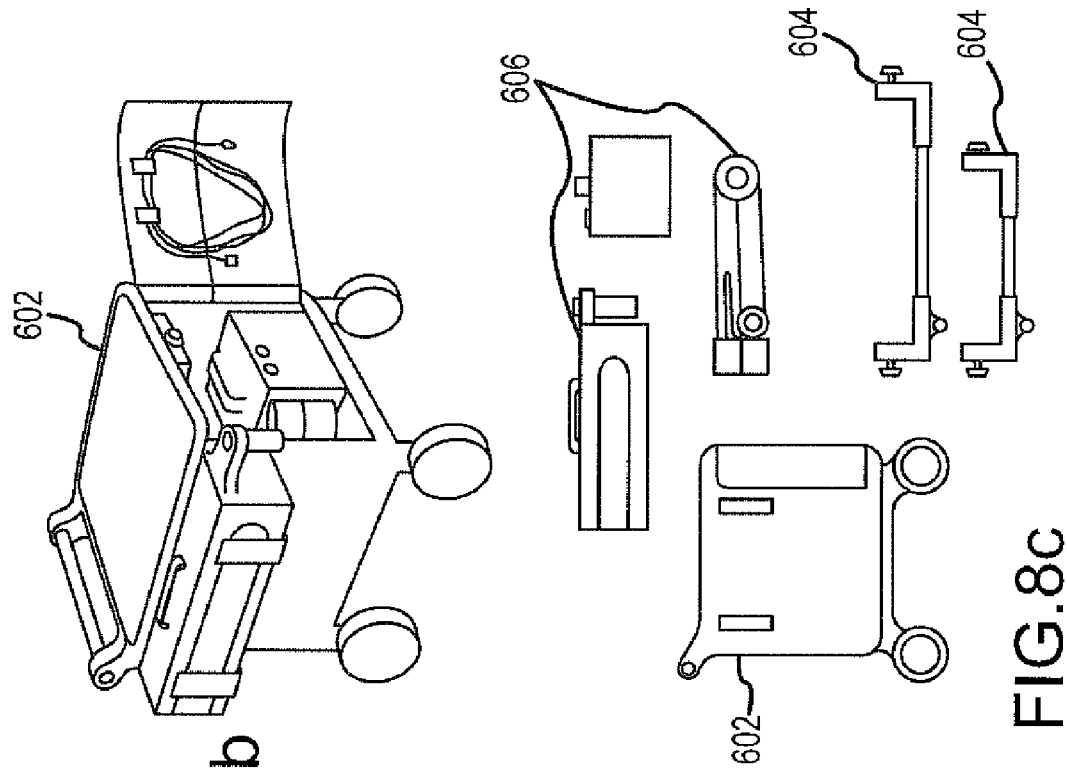
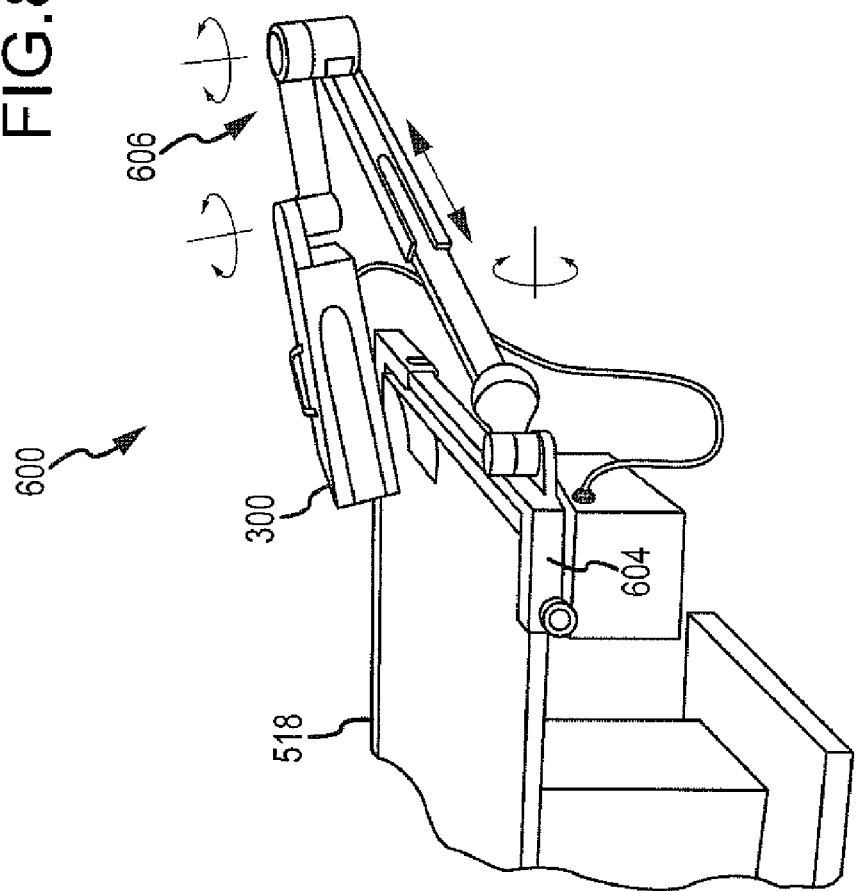

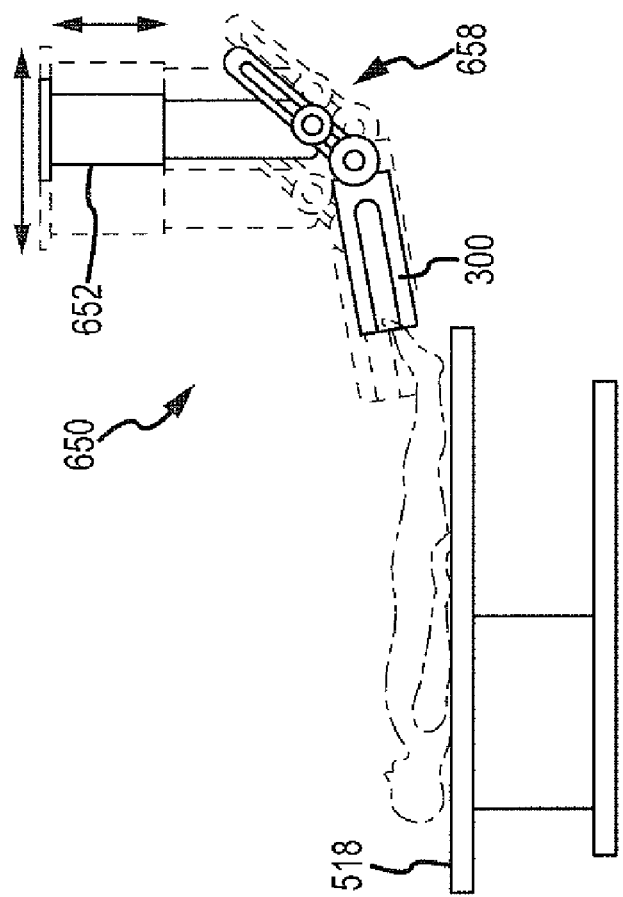
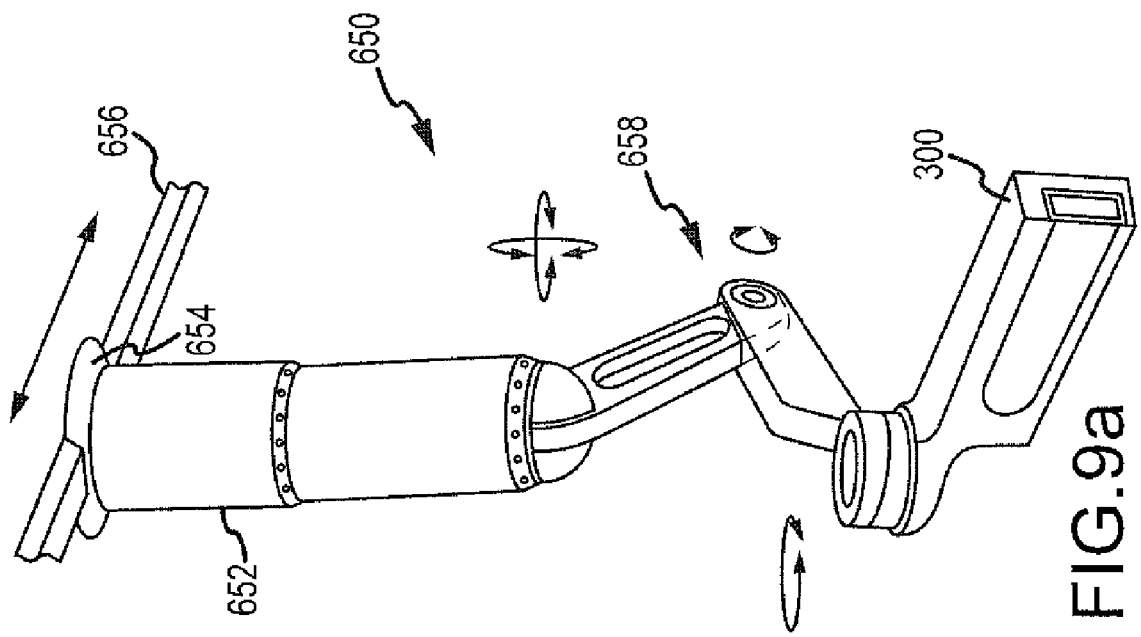
FIG.9b
FIG.9a

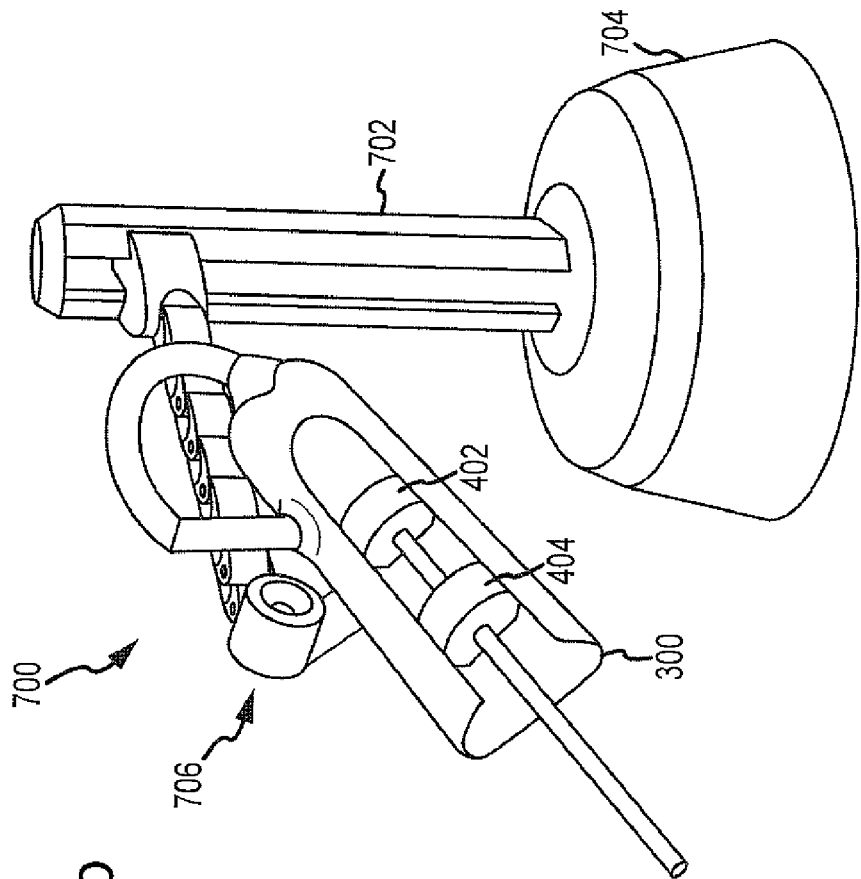
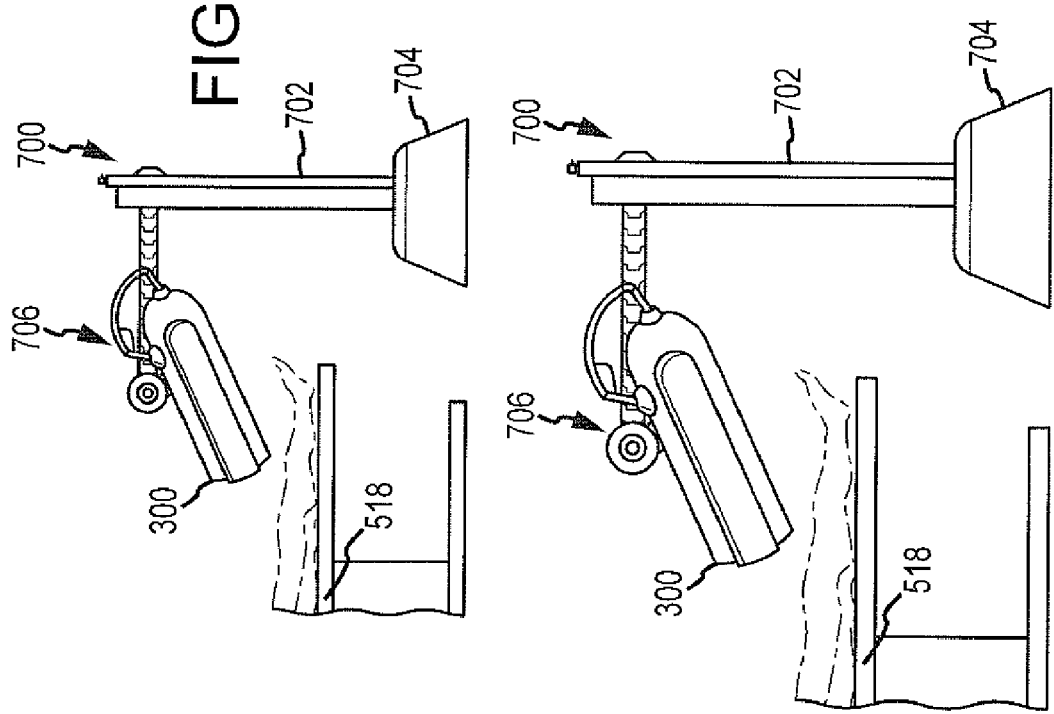

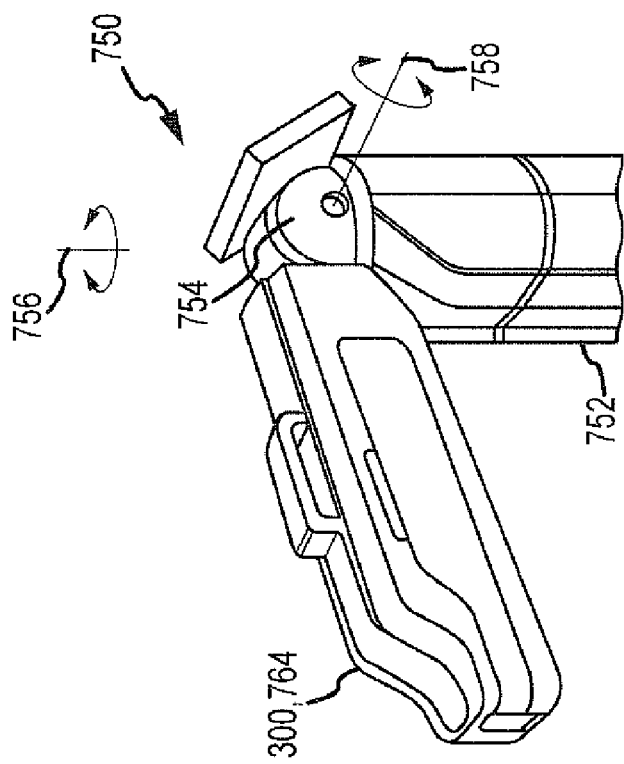
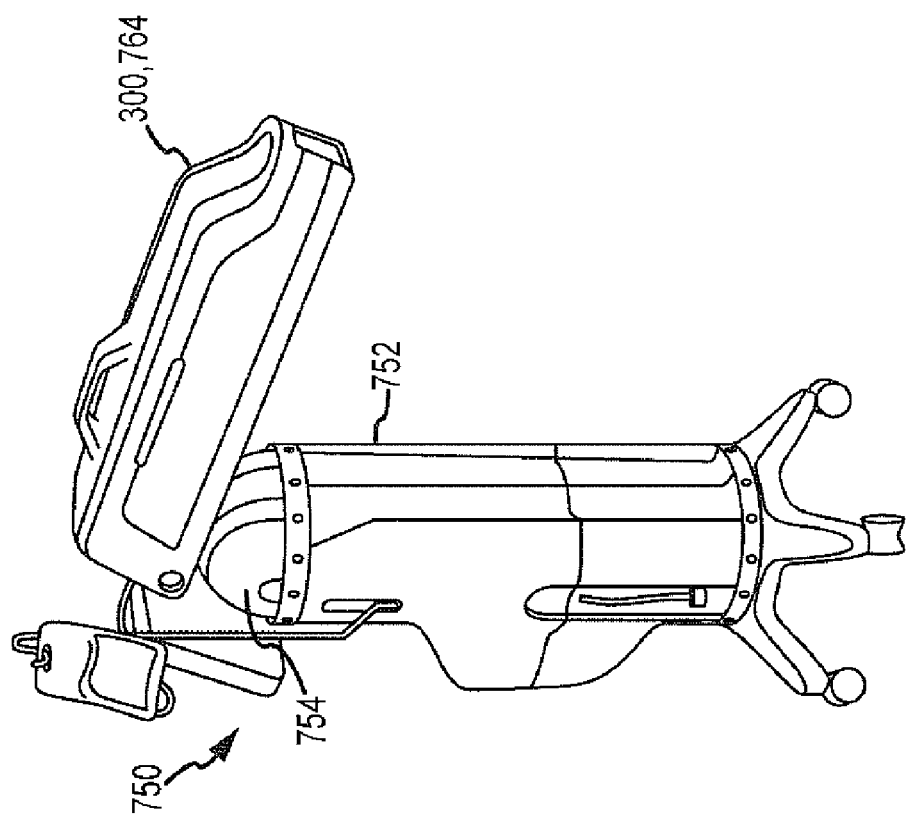
FIG.11b
FIG.11a

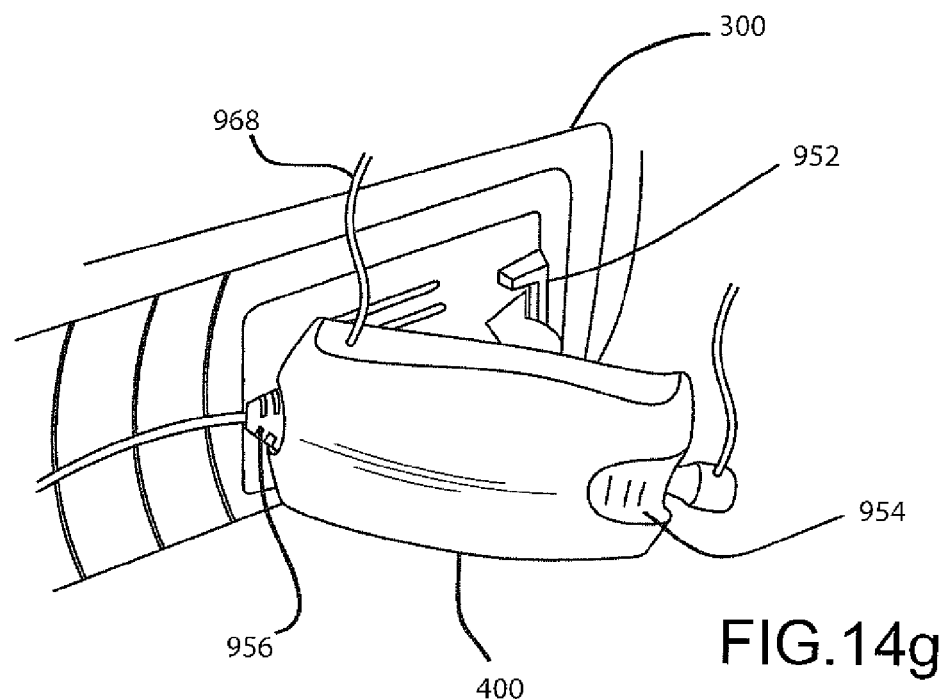
FIG.14g
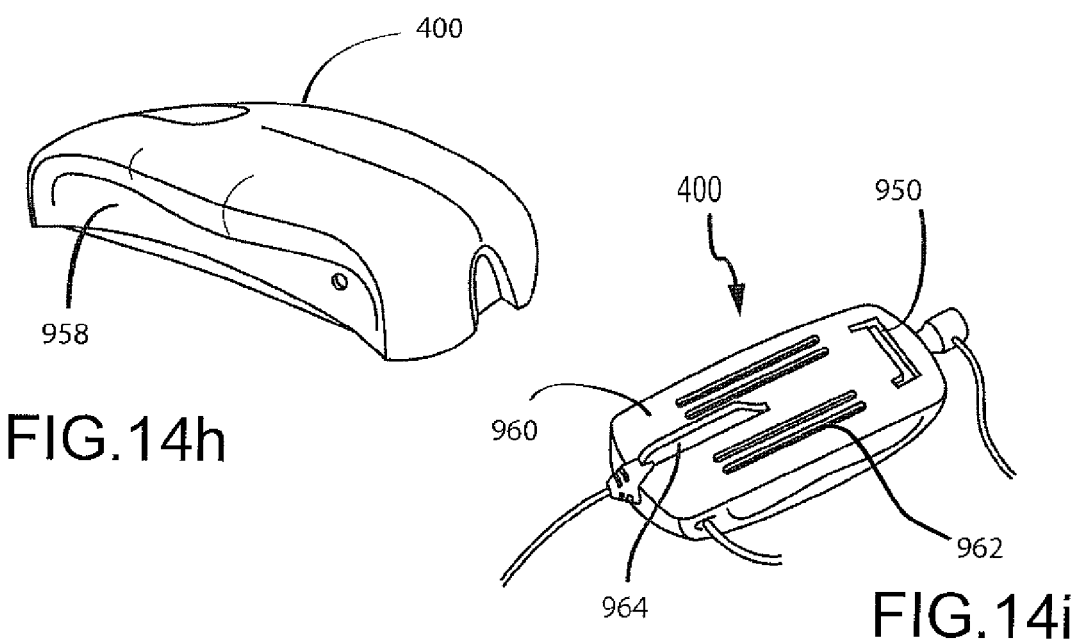
FIG.14h
FIG.14i
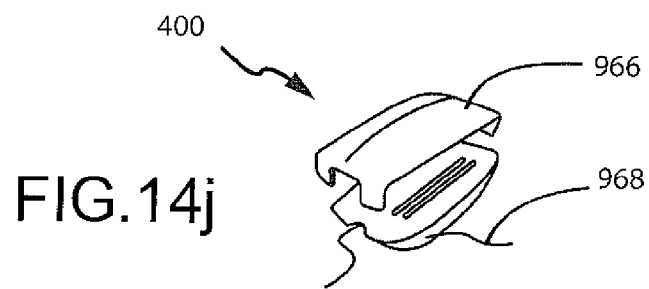
FIG.14j

ROBOTIC CATHETER SYSTEM

CROSS REFERENCE TO RELATED APPLICATIONS

This application claims the benefit of priority to U.S. Provisional Application Nos. 61/040,143, filed Mar. 27, 2008 and 61/099,904, filed Sep. 24, 2008, the entire disclosures of which are incorporated herein by reference.

BACKGROUND OF THE INVENTION a. Field of the Invention

This invention relates to a robotic catheter system and method for automated control of a catheter and related components. In particular, the instant invention relates to a robotic catheter system for manipulating a catheter and related components, for example, for diagnostic, therapeutic, mapping and ablative procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

The inventors herein have thus recognized a need for a system and method for precise and dynamic automated control of a catheter and its related components, for example, for diagnostic, therapeutic, mapping and ablative procedures, that will minimize and/or eliminate procedural variability due to a user's skill level. The inventors herein have also recognized a need for a system and method for performing user-specified procedures at the patient site or from a remote location.

BRIEF SUMMARY OF THE INVENTION

It is desirable to provide a system and method for precise and dynamic automated control of a catheter and its related components. In particular, it is desirable to provide a system and method for precise and dynamic automated control, for example, for diagnostic, therapeutic, mapping and ablative procedures, that will minimize and/or eliminate procedural variability due to a user's skill level, with the procedures being optionally performed at the patient site or from a remote location.

A system and method for precise and dynamic automated control of a catheter and its related components may include a robotic catheter system including one or more robotic catheter manipulator assemblies supported on a manipulator support structure. The robotic catheter manipulator assembly may include one or more removably mounted robotic catheter device cartridges and robotic sheath device cartridges, with each cartridge being generally linearly movable relative to the robotic catheter manipulator assembly. An input control system may be provided for controlling operation of the robotic catheter manipulator assembly. A visualization system may include one or more display monitors for displaying a position of a catheter and/or a sheath respectively attached to the robotic catheter and sheath device cartridges.

For the robotic catheter system described above, in one embodiment, the manipulator support structure may include an attachment assembly for attaching the robotic catheter manipulator assembly to an operation bed. In one embodiment, the manipulator support structure may include one or more retractable wheels for facilitating transport of the robotic catheter manipulator assembly. In one embodiment, the manipulator support structure may include one or more support arms for adjustably supporting the robotic catheter manipulator assembly, or multiple support arms for supporting multiple robotic catheter manipulator assemblies. In one embodiment, the support arm may adjustably position the robotic catheter manipulator assembly in a plane disposed at an acute angle relative to a generally horizontally disposed operation bed. Alternatively, the support arm may adjustably position the robotic catheter manipulator assembly in plane disposed generally orthogonal to a generally horizontally disposed operation bed. In one embodiment, the support arm may adjustably position the robotic catheter and sheath device cartridges for movement in a plane disposed at an acute angle relative to a generally horizontally disposed operation bed. Alternatively, the support arm may adjustably position the robotic catheter and sheath device cartridges for movement in a plane disposed generally orthogonal to a generally horizontally disposed operation bed.

For the robotic catheter system described above, in one embodiment, the robotic catheter manipulator assembly support structure may be substantially fixedly disposed relative to an operation bed. The robotic catheter system may further include a case for transport and sterile use of the robotic catheter manipulator assembly. In one embodiment, a sterile shield may be provided for preventing contamination of the robotic catheter manipulator assembly. In one embodiment, the robotic catheter system may be portable (e.g. movable without lifting). In one embodiment, one or more of the catheter and sheath cartridges may be rotatable relative to the robotic catheter manipulator assembly.

For the robotic catheter system described above, in one embodiment, the robotic catheter manipulator assembly may include a support member including one or more catheter manipulation bases and one or more sheath manipulation bases movable relative to each other and to the support member, with each respective manipulation base being releasably connectable to the catheter and sheath device cartridges. In one embodiment, the catheter manipulation base or the catheter device cartridge may include one or more first elements engageable with one or more complementary second elements slidably engaged with the other one of the catheter manipulation base or the catheter device cartridge for controlling movement of the catheter by pulling a steering wire attached to the catheter and the first or second elements. In one embodiment, the sheath manipulation base or the sheath device cartridge may include one or more first elements engageable with one or more complementary second elements slidably engaged with the other one of the sheath manipulation base or the sheath device cartridge for controlling movement of the sheath by pulling a steering wire attached to the sheath and the first or second elements. In one embodiment, the catheter and sheath manipulation bases may be linearly movable relative to each other and to the support member. In one embodiment, the catheter manipulation base may be disposed generally behind the sheath manipulation base to allow insertion of the catheter into the sheath.

For the robotic catheter system described above, in one embodiment, the input control system may include one or more joysticks, instrumented (e.g. haptic) gloves, mouse type devices, space-balls and/or 3D input devices. In another embodiment, the input may be a pre-defined path drawn in a solid model and calculated and implemented by the system. In one embodiment, the input control system may include haptic feedback based on actual sensed forces on a distal catheter tip or impedance measured from the distal catheter tip. In one embodiment, the input control system may include haptic feedback based on virtual catheter tip proximity to virtual cardiac anatomy. In one embodiment, the visualization system may include an orientation vector display for showing direction of a thumb switch deflection for the input control system. In one embodiment, the input control system may include active tensioning of steering wires attached to the catheter and sheath. In one embodiment, the input control system may include pre-defined speed zones for varying speed of movement of the catheter and sheath in predetermined areas in the anatomy of a patient.

In one embodiment, a system and method for precise and dynamic automated control of a catheter and its related components may include a robotic catheter system including one or more robotic manipulator assemblies supported on a manipulator support structure. The robotic manipulator assembly may include one or more removably mounted robotic first surgical instrument device cartridges and robotic second surgical instrument device cartridges, with each cartridge being generally linearly movable relative to the robotic manipulator assembly. An input control system may control operation of the robotic manipulator assembly. A visualization system may include one or more displays for displaying a position of one or more first and second surgical instruments respectively attached to the robotic first and second surgical instrument device cartridges.

For the robotic catheter system described above, in one embodiment, the manipulator support structure may include an attachment assembly for attaching the robotic manipulator assembly to an operation bed. In one embodiment, the manipulator support structure may include one or more retractable wheels for facilitating transport of the robotic manipulator assembly. In one embodiment, the manipulator support structure may include one or more support arms for adjustably supporting the robotic manipulator assembly, or multiple support arms for supporting multiple robotic manipulator assemblies. In one embodiment, the support arm may adjustably position the robotic manipulator assembly in a plane disposed at an acute angle relative to a generally horizontally disposed operation bed. Alternatively, the support arm may adjustably position the robotic manipulator assembly in plane disposed generally orthogonal to a generally horizontally disposed operation bed. In one embodiment, the support arm may adjustably position the robotic first and second surgical instrument device cartridges for movement in a plane disposed at an acute angle relative to a generally horizontally disposed operation bed. Alternatively, the support arm may adjustably position the robotic first and second surgical instrument device cartridges for movement in a plane disposed generally orthogonal to a generally horizontally disposed operation bed.

For the robotic catheter system described above, in one embodiment, the robotic manipulator assembly support structure may be substantially fixedly disposed relative to an operation bed. In one embodiment, a case may be provided for transport and sterile use of the robotic manipulator assembly. In one embodiment, a sterile shield may be provided for preventing contamination of the robotic manipulator assembly. In one embodiment, the robotic catheter system may be portable (e.g. movable without lifting). In one embodiment, one or more of the first and second surgical instrument device cartridges may be rotatable relative to the robotic manipulator assembly.

For the robotic catheter system described above, in one embodiment, the robotic manipulator assembly may include a support member including one or more first surgical instrument manipulation bases and one or more second surgical instrument manipulation bases movable relative to each other and to the support member, with each respective manipulation base being releasably connectable to the first and second surgical instrument device cartridges. In one embodiment, the first surgical instrument manipulation base or the first surgical instrument device cartridge may include one or more first elements engageable with one or more complementary second elements slidably engaged with the other one of the first surgical instrument manipulation base or the first surgical instrument device cartridge for controlling movement of the first surgical instrument by pulling a steering wire attached to the first surgical instrument and the first or second element. Alternatively, the second surgical instrument manipulation base or the second surgical instrument device cartridge may include one or more first elements engageable with one or more complementary second elements slidably engaged with the other one of the second surgical instrument manipulation base or the second surgical instrument device cartridge for controlling movement of the second surgical instrument by pulling a steering wire attached to the second surgical instrument and the first or second elements.

For the robotic catheter system described above, in one embodiment, the first and second surgical instrument manipulation bases may be linearly movable relative to each other and to the support member. In one embodiment, the first surgical instrument manipulation base may be disposed generally behind the second surgical instrument manipulation base to allow insertion of the first surgical instrument into the second surgical instrument. In one embodiment, the input control system may include one or more joysticks, instrumented (e.g. haptic) gloves, mouse type devices, space-balls and/or 3D input devices. In another embodiment, the input may be a pre-defined path drawn in a solid model and calculated and implemented by the system. In one embodiment, the input control system may include haptic feedback based on actual sensed forces on a distal first surgical instrument tip or impedance measured from the distal first surgical instrument tip. In one embodiment, the input control system may include haptic feedback based on virtual first surgical instrument tip proximity to virtual cardiac anatomy. In one embodiment, the visualization system may include an orientation vector display for showing direction of a thumb switch deflection for the input control system. In one embodiment, the input control system may include active tensioning of steering wires attached to the first and second surgical instruments. In one embodiment, the input control system may include pre-defined speed zones for varying speed of movement of the first and second surgical instruments in predetermined areas in the anatomy of a patient. In one embodiment, the first and/or second surgical instruments may be a transseptal needle, a catheter or a sheath. The manipulator support structure, in one embodiment, may be an integrated system including a RF generator, a saline pump and/or saline bags. The robotic manipulator assembly, in one embodiment, may include a cartridge override (e.g. emergency or on/off switch) for preventing and/or disabling movement of the cartridges.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 1 is an isometric diagrammatic view of a robotic catheter system, illustrating an exemplary layout of various system components;

FIGS. 3a-3c are enlarged isometric, and FIGS. 3d-3i are respectively enlarged left side, right side, top, front, back and a corresponding left side view of a first embodiment of a robotic catheter manipulator assembly.

FIGS. 4d-4g are respectively enlarged top and right side, and respectively sections A-A and B-B taken generally along lines A-A and B-B in FIG. 4d, of a first embodiment of a manipulation base;

FIGS. 8a-8c are isometric and related diagrammatic views of a third embodiment of a robotic catheter manipulator support structure, and various components thereof;

FIGS. 9a and 9b are isometric and related diagrammatic views of a fourth embodiment of a robotic catheter manipulator support structure;

FIGS. 10a-10c are isometric and related diagrammatic views of a fifth embodiment of a robotic catheter manipulator support structure;

FIGS. 11a-11h are isometric and related diagrammatic views of a sixth embodiment of a robotic catheter manipulator support structure, and various components thereof;

FIGS. 14a-14j are isometric and related diagrammatic views of a ninth embodiment of a robotic catheter manipulator support structure, and various components thereof;

DETAILED DESCRIPTION OF EMBODIMENTS OF THE INVENTION

Figure 2A:
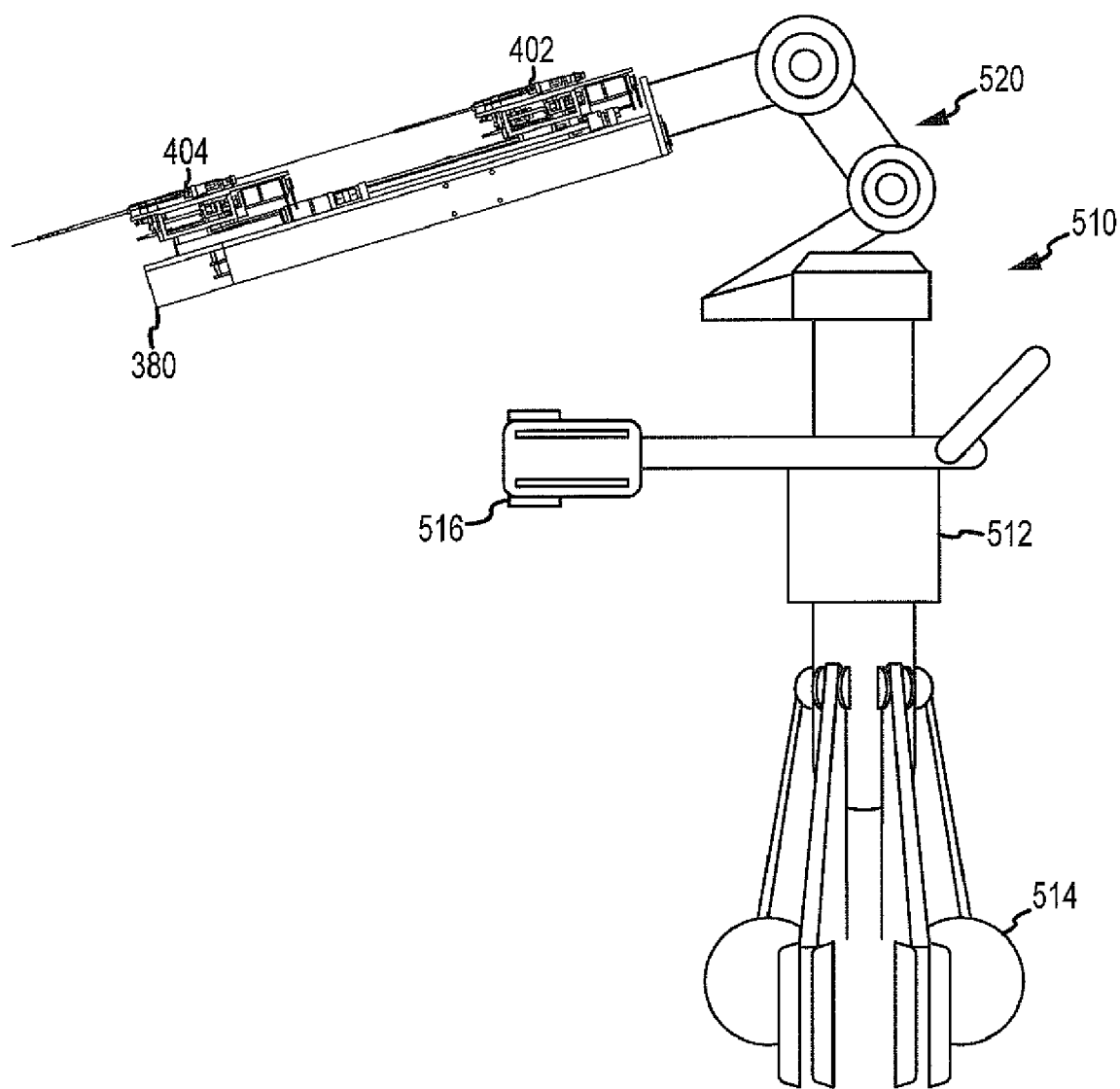
FIGS. 2a-2c are isometric and related diagrammatic views of a first embodiment of a robotic catheter manipulator support structure, with FIG. 2a illustrating a robotic catheter manipulator slightly angled from a generally horizontal position.
Figure 2B:
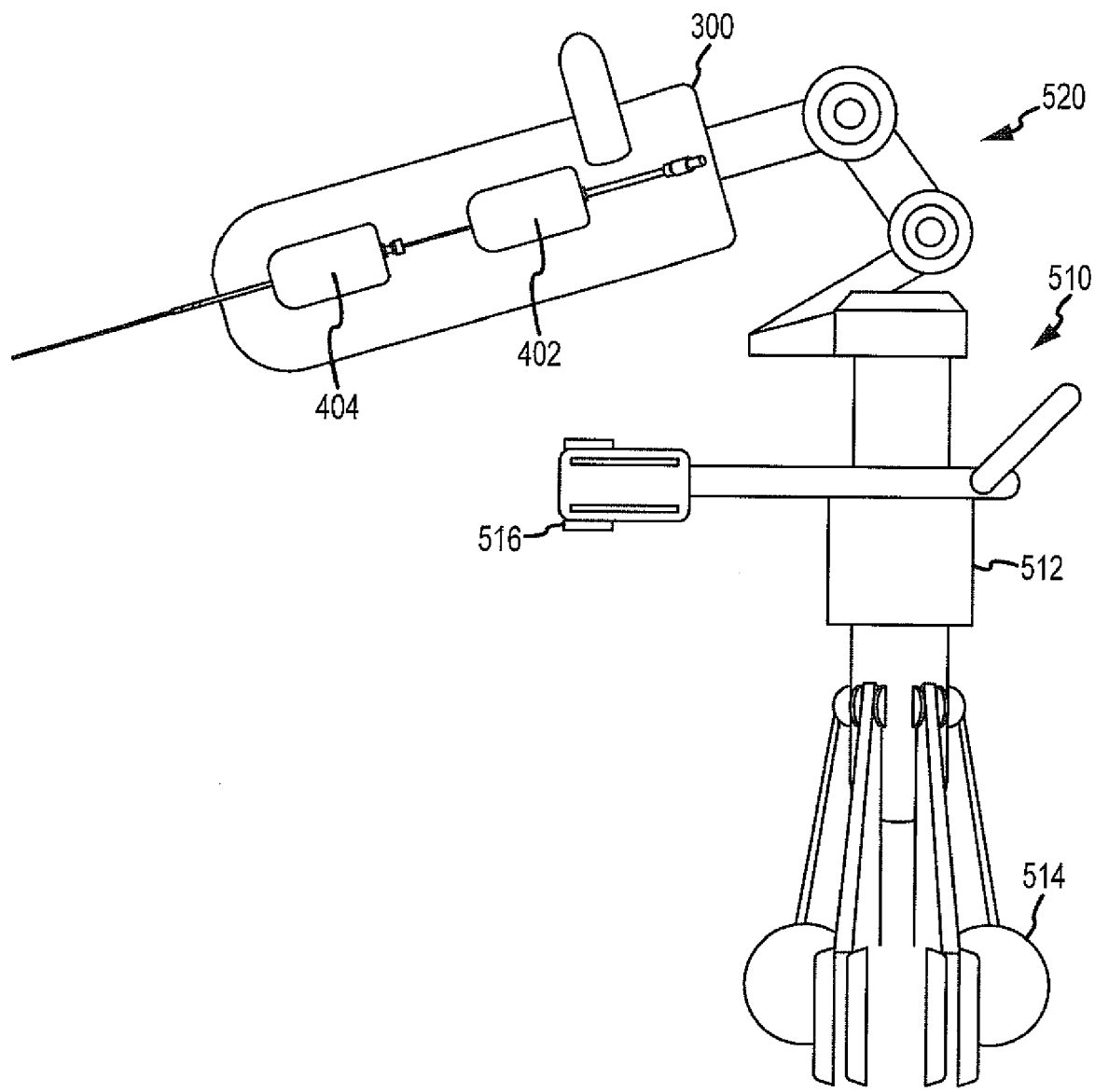
Figure 2C:
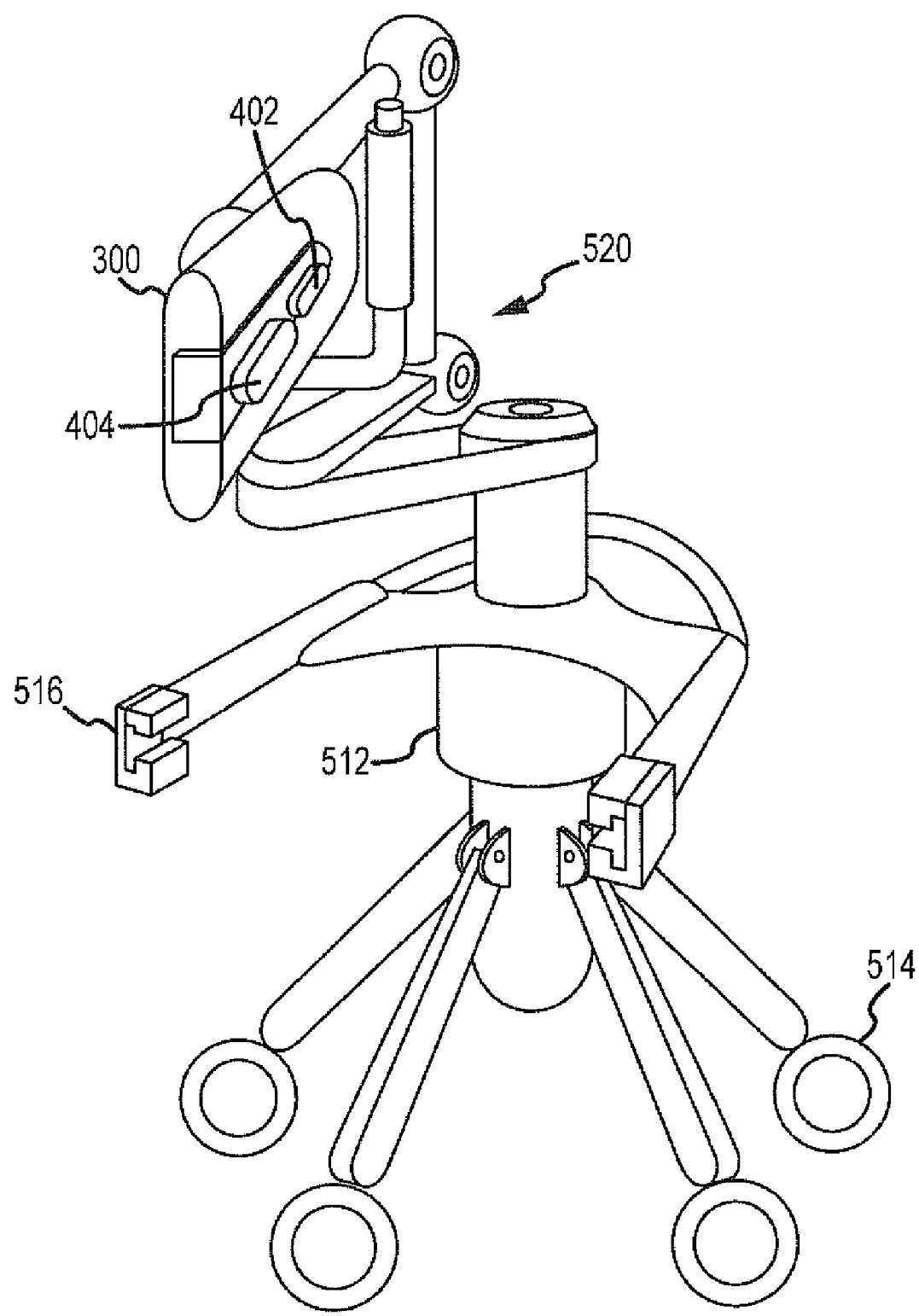

Referring now to the drawings wherein like reference numerals are used to identify identical components in the various views, an embodiment of robotic catheter system 10 (described in detail below), also referred to as "the system," may be likened to power steering for a catheter system. The system may be used, for example, to manipulate the location and orientation of catheters and sheaths in a heart chamber or in another body cavity. As shown in FIG. 1 and described in detail below, robotic catheter system 10 may generally incorporate a human input device and control system (referred to as "input control system") 100, e.g., a joystick and related controls (described below and in detail in commonly owned and copending applications titled "Robotic Catheter System Input Device" and "Robotic Catheter System Including Haptic Feedback"), that a user such as an electrophysiologist (EP) may interact with, an electronic control system 200 (described in detail in commonly owned and copending application titled "Robotic Catheter System with Dynamic Response") that translates motions of the user at the input device into a resulting movement of a catheter tip, and a visualization system 12 that provides a user with real-time or near-real-time positioning information concerning the catheter tip. The system may further include closed-loop feedback using an EnSite NavX system 14 and/or optical force transducers, a robotic catheter manipulator assembly 300 (described in detail in commonly owned and copending application titled "Robotic Catheter Manipulator Assembly") for operating a robotic catheter device cartridge 400 (described in detail in commonly owned and copending applications titled "Robotic Catheter Device Cartridge" and "Robotic Catheter Rotatable Device Cartridge"), and manipulator support structure 500 (described in detail below). The system provides the user with a similar type of control provided by a conventional manual system, but allows for repeatable, precise, and dynamic movements. The respective disclosures of the above-identified and other commonly owned and copending applications discussed in this application are incorporated herein by reference.

An embodiment of robotic catheter system 10 may involve automated catheter movement. A user, such as an EP, could identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then perform the desired treatment or therapy—which may further be in accordance with a defined algorithm. This system could enable full robotic control by using optimized path planning routines together with closed-loop position control. Furthermore, the system could automate certain "best-practices," such as pulling the catheter across the surface, or making contact at an oblique angle.

Referring to FIG. 1, input control system 100 will be described briefly.

Input control system 100 of commonly owned and copending application titled "Robotic Catheter System Input Device," may generally allow a user to control the movement and advancement of both the catheter and sheath. Generally, several types of joysticks may be employed, including, without limitation, instrumented traditional catheter handle controls, oversized catheter models, instrumented, user-wearable gloves, and traditional joysticks. In embodiments, for example and without limitation, the joystick may be spring centering so that any movement from the center position causes an incremental movement of the actual catheter tip, or the joystick may work in absolute terms. Haptic feedback may also be incorporated to provide a user with a sense of when contact has been made.

Referring to FIG. 1, electronic control system 200 will be described briefly.

As discussed in detail in commonly owned and copending applications titled "Robotic Catheter System Input Device," and "Robotic Catheter System with Dynamic Response," many additional features may be included with embodiments of the system to, for example, improve the accuracy or effectiveness of the system. Such features may include, closed-loop feedback using EnSite NavX system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

Visualization system 12 may provide a user with real-time or near-real-time positioning information concerning the catheter tip. In an exemplary embodiment, system 12 may include an EnSite NavX monitor 16 for displaying cardiac chamber geometries or models, displaying activation timing and voltage data to identify arrhythmias, and for facilitating guidance of catheter movement. A fluoroscopy monitor 18 may be provided for displaying a real-time x-ray image or for assisting a physician with catheter movement. Additional exemplary displays may include an ICE and EP Pruka displays, 20, 22, respectively.

Referring to FIG. 1, EnSite NavX system 14 will be described briefly.

EnSite NavX system 14 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. EnSite NavX system 14 may collect electrical data from catheters and use this information to track or navigate their movement and construct three-dimensional (3-D) models of the chamber.

Referring to FIGS. 1-6*c*, robotic catheter manipulator assembly 300 for operating robotic catheter device cartridges 400 will be described briefly.

As generally shown in FIGS. 1-6*c*, robotic catheter system 10 may include one or more robotic catheter manipulator assemblies 300 that serve as the mechanical control for the movements or actions of one or more robotic catheter device cartridges 400. FIG. 1 illustrates a generally vertically oriented manipulator assembly 300 for minimizing approach angle, and FIG. 2*a* illustrates a manipulator assembly 380 slightly angled from a generally horizontal position. FIGS. 3*a* and 6*a*-6*c* respectively illustrate first-fourth embodiments of assemblies 300, namely assemblies 302, 370, 372 and 374, described in detail in commonly owned and copending application titled "Robotic Catheter Manipulator Assembly." Manipulator assembly 302 and its associated components will be described herein for facilitating an understanding of robotic catheter system 10.

Referring to FIGS. 1 and 3*a*-5*e*, the catheter and sheath configuration of robotic catheter manipulator assembly 300 and robotic catheter device cartridges 400 will be described in detail.

As generally shown in FIGS. 1 and 3*a*-5*e* and discussed in greater detail below, the first embodiment of manipulator assembly 302 may respectively include both catheter and sheath manipulator mechanisms 304, 306. In this arrangement, the catheter and sheath manipulator mechanisms 304, 306 may be aligned such that the catheter can pass through the sheath in a coaxial arrangement. Each mechanism 304, 306 may be further capable of independent advancement/retraction (shown generally as directions $D_1$ and $D_2$) and independent four-wire steering control (e.g., eight total steering wires, comprising four sheath control wires and four catheter control wires), as discussed in detail below.

With a configuration of robotic catheter system 10, such as shown in FIGS. 1 and 3*a*-5*e*, there will be relative travel of a first embodiment of catheter and sheath cartridges 402, 404 and relative movement associated with a portion of a catheter 406 between the two cartridges 402, 404. For many embodiments, there may be a water-tight fit of a proximal sheath opening 408, which can sometimes create resistance to catheter advancement. In order to help eliminate/reduce the potential issue of columnar buckling of catheter 406, a length of stiff material, such as, for example, a solid metal rod or fiber reinforced composite, may be incorporated on the interior of the proximal portion of catheter 406. Such a material may locally increase the catheter's bending stiffness and provide enhanced buckling support. Thus catheter 406 may be proximally stiffened so that the length of the catheter proximally extending from sheath cartridge 404 is less likely to buckle during relative translation, as the entire length of catheter 406 extends into sheath 410.

Referring to FIGS. 1 and 3*a*-5*e*, the first embodiment of robotic catheter manipulator assembly 302 will be described in detail.

As generally shown in FIGS. 1 and 3*a*-5*e*, robotic catheter system 10 which includes one or more robotic catheter manipulator assemblies 300, includes the first embodiment of robotic catheter manipulator assembly 302 including both catheter and sheath manipulation mechanisms 304, 306 for manipulating, for example, catheter and sheath cartridges 402, 404. Manipulator assembly 302 may include interconnected/interlocking manipulation bases 308, 310 for catheter and sheath cartridges 402, 404, and likewise may include electrical "handshake" functionality as discussed below. Each interlocking base 308, 310 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 3*a*, each interlocking base may be translated by high precision drive mechanisms 312, 314. Such drive mechanisms may include, for example and without limitation, a motor driven lead screw or ball screw.

Figure 4A:
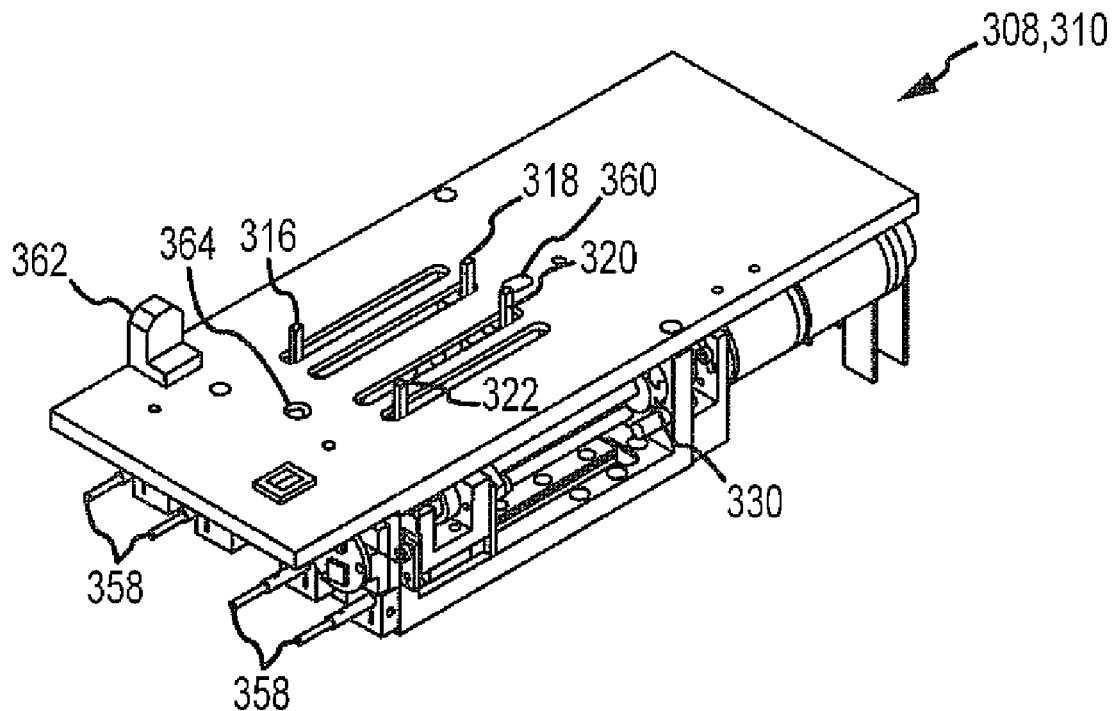
FIGS. 4a-4c are enlarged isometric views.
Figure 4B:
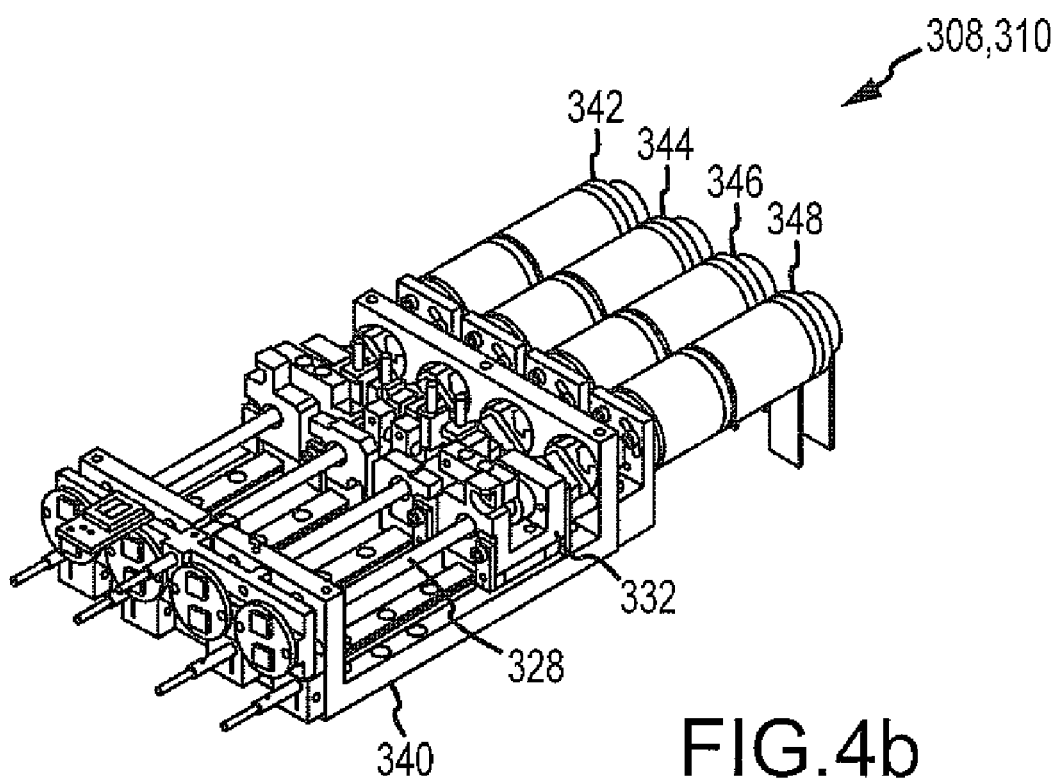
Figure 4C:
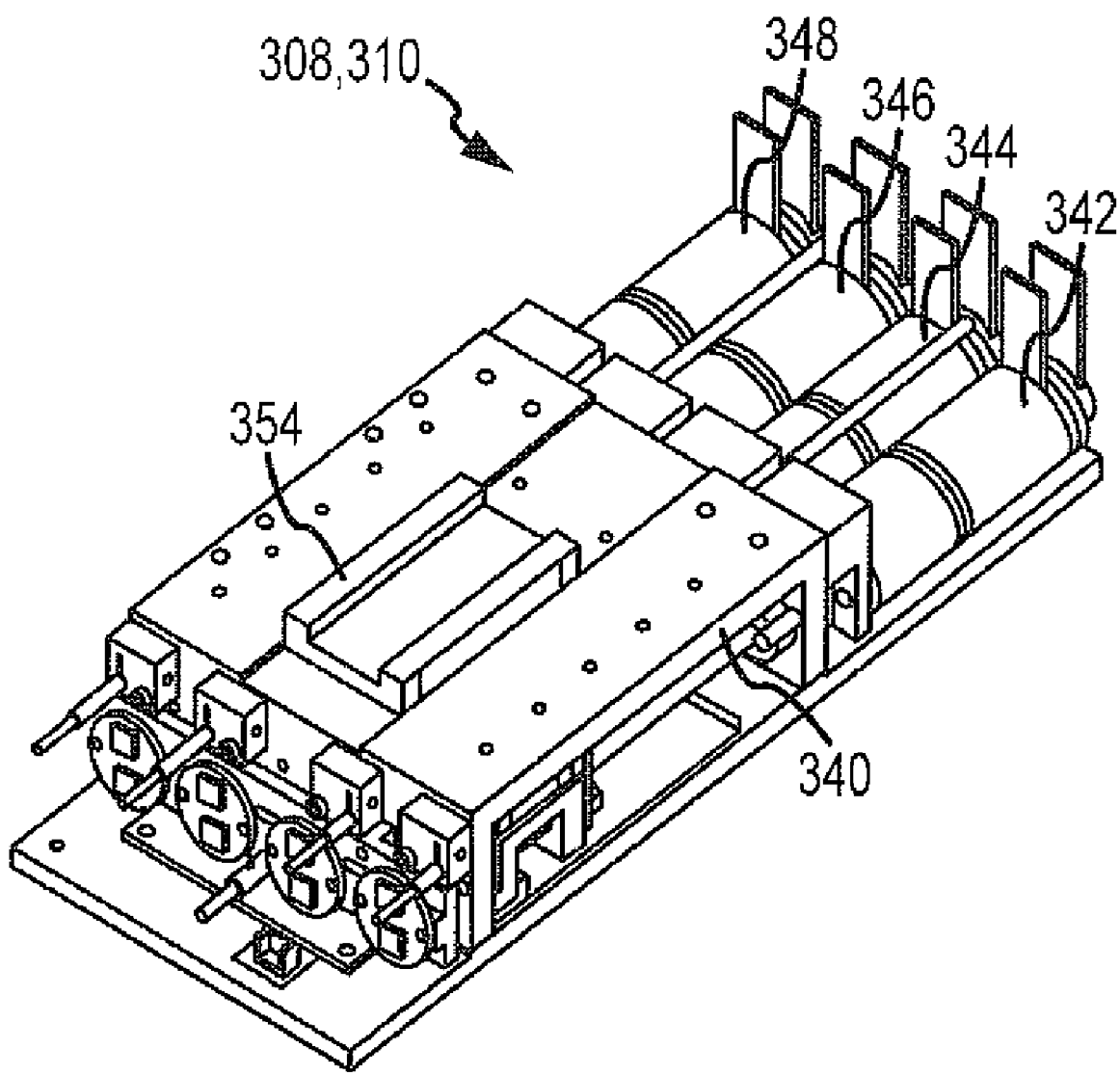
Figure 4D:
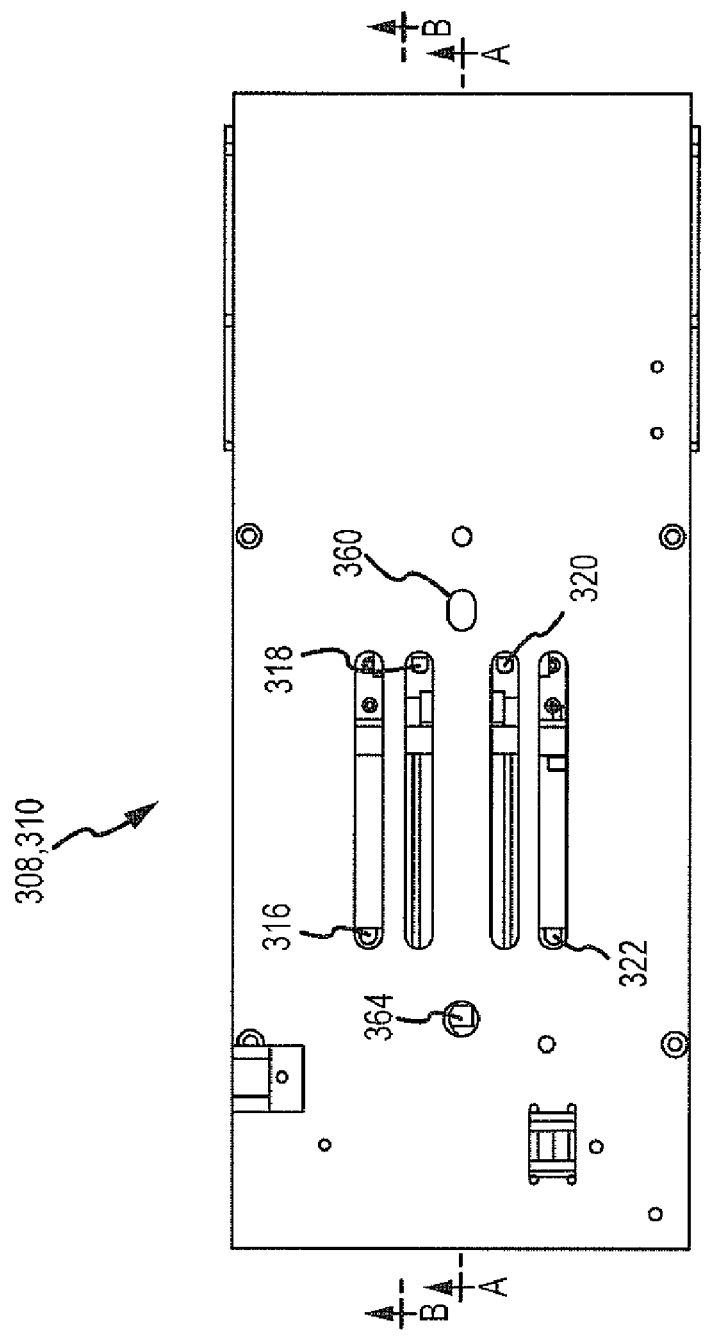
Figure 4E:
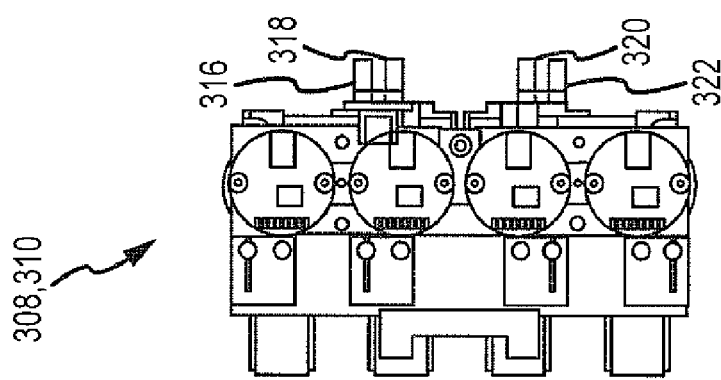

As shown in FIGS. 3*a*-3*i* and 4*a*-4*g*, for each cartridge 402, 404, an associated manipulation base 308, 310 may include a plurality of fingers 316, 318, 320 and 322, (e.g., one per steering wire) that extend or protrude upwardly to contact and interact with the steering wire slider blocks (such as slider blocks 412, 414, 416, 418) to independently tension select steering wires 420, 422, 424, 426. Each finger can be configured to be independently actuated by a precision drive mechanism, such as a motor driven ball screw 324, and may be outfitted with force sensors to measure corresponding steering wire tension. Each motor driven ball screw (for both finger control and cartridge translation control) may further include encoders to measure a relative and/or an absolute position of each element of the system. As shown in FIG. 4*a*, bearing 332 and coupler 330 of ball screw 324 may engage frame 340 of respective bases 308, 310 and a corresponding finger 316, 318, 320 or 322 may be mounted adjacent a strain gauge for measuring the corresponding steering wire tension.

Referring to FIGS. 4*a*-4*g*, bases 308, 310 may include exemplary components such as motors 342, 344, 346 and 348, respectively coupled to fingers 316, 318, 320 and 322. A bearing 354 may be provided for sliding of bases 308, 310 on track 356. A plurality of inductive sensors (e.g. home sensors) 358 may be provided for guiding each manipulation base to a safe position.

Manipulator assembly 302 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference. In an embodiment, high-precision drive mechanisms 312, 314 for translating each of the catheter and sheath cartridges 402, 404 may be positioned generally below the manipulator bases 308, 310 to allow the respective cartridges to be positioned toward the lower area of the manipulator. By holding a close distance, the ingress angle of the catheter/sheath may be minimized, and the manipulator control may be positioned more closely to an insertion site.

Figure 3C:
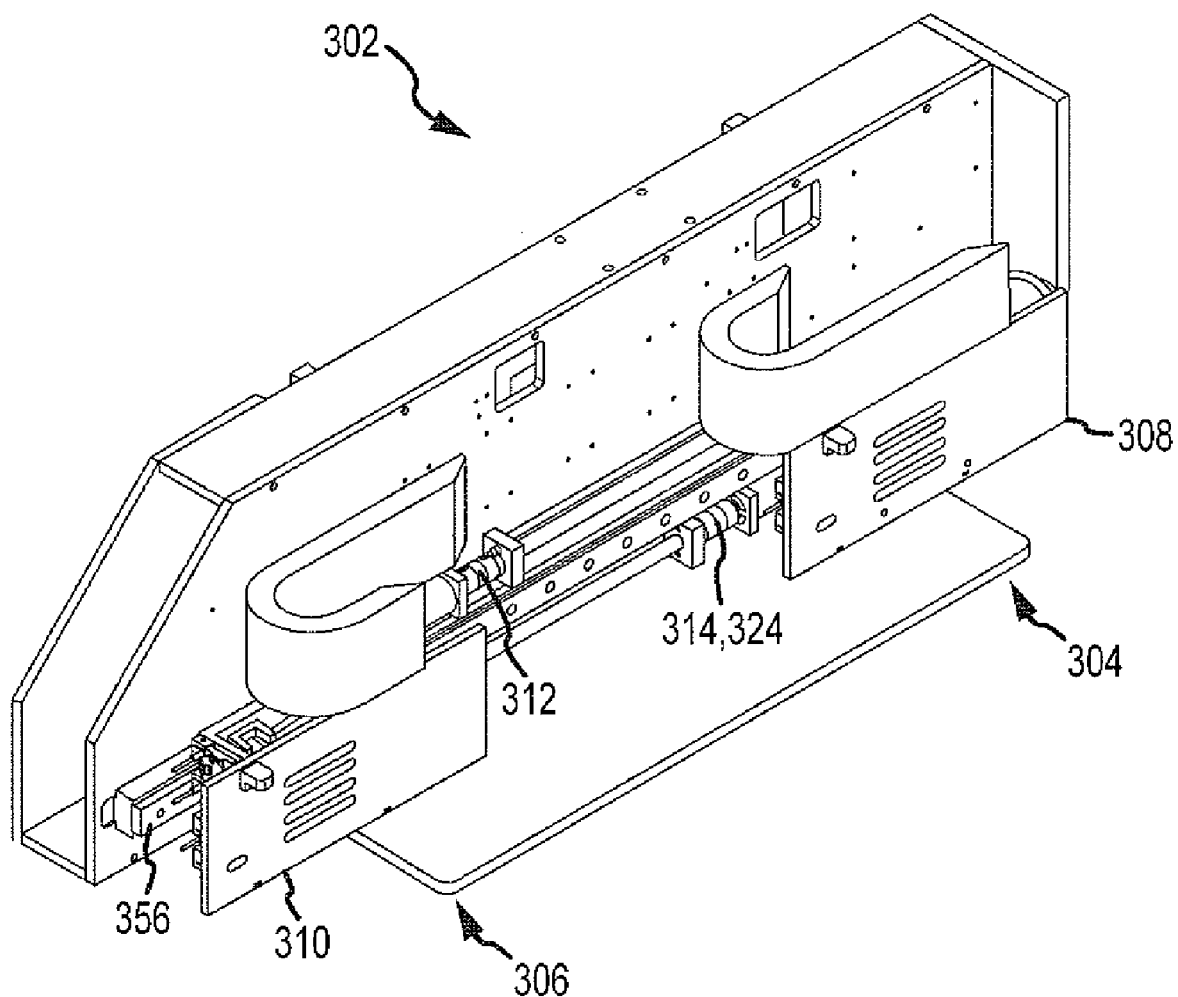
Figure 3H:
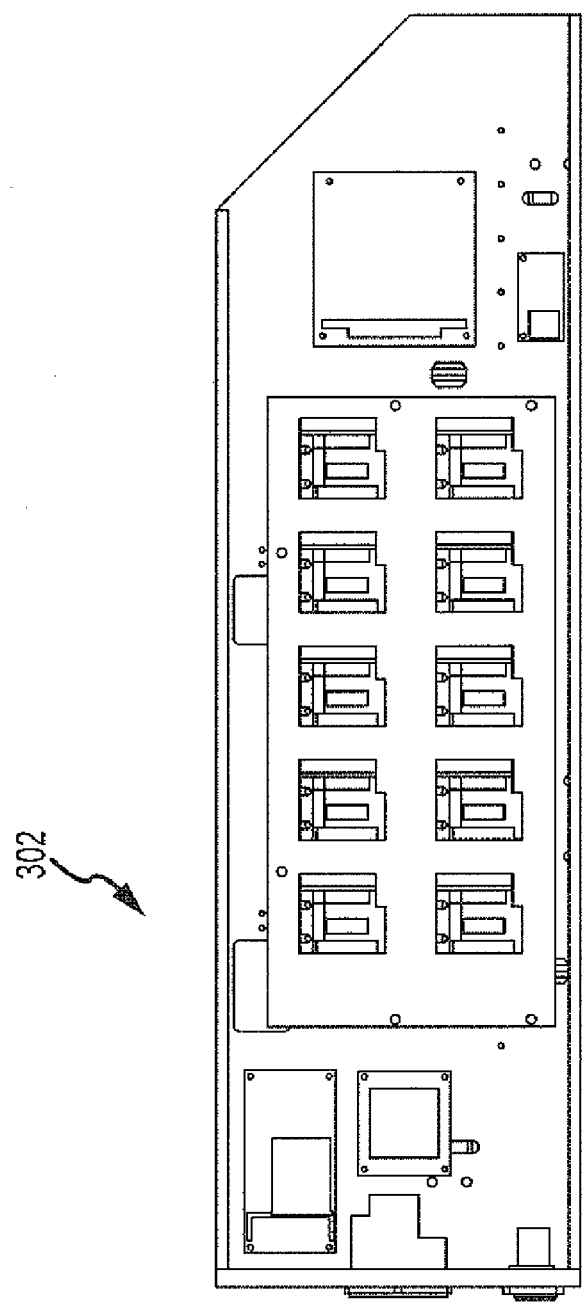
Figure 3I:
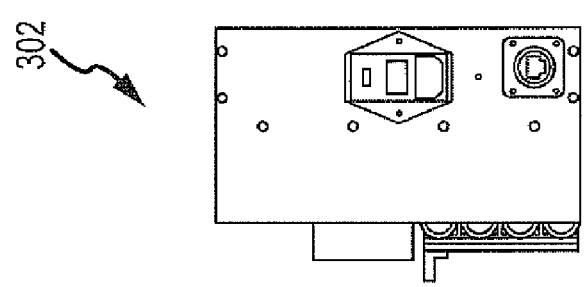
Figure 3K:
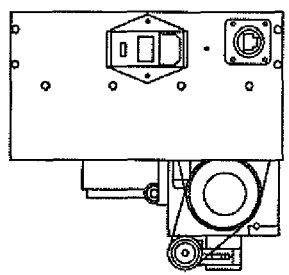
FIGS. 3j-3m are respectively enlarged left side, right side, top and front views of the robotic catheter manipulator assembly of FIG. 3a, illustrating use of the manipulator assembly with a robotic catheter rotatable device cartridge.
Figure 3L:
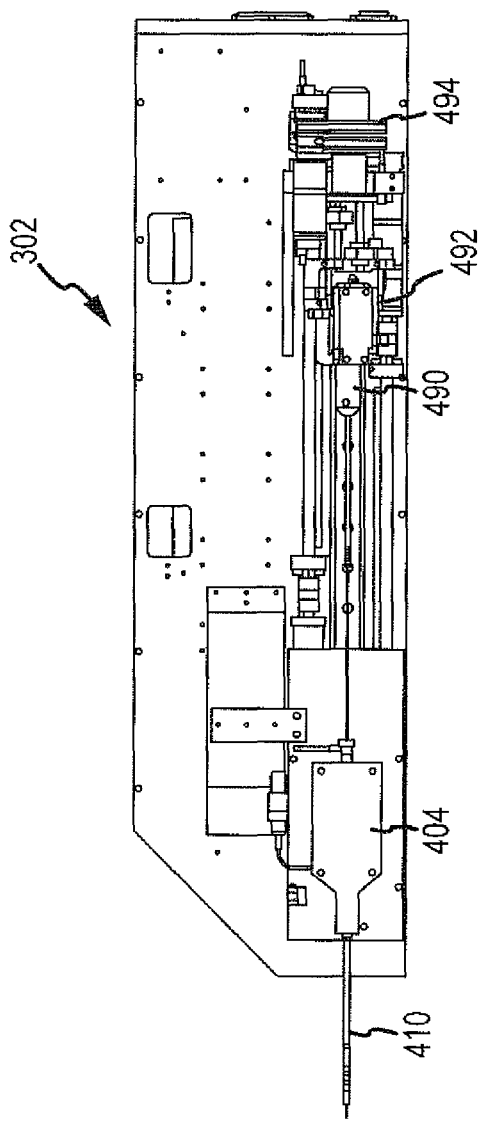
Figure 3J:
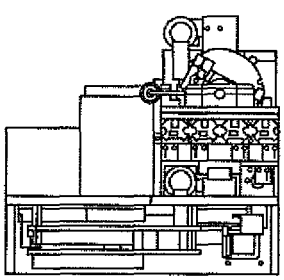
Figure 3M:
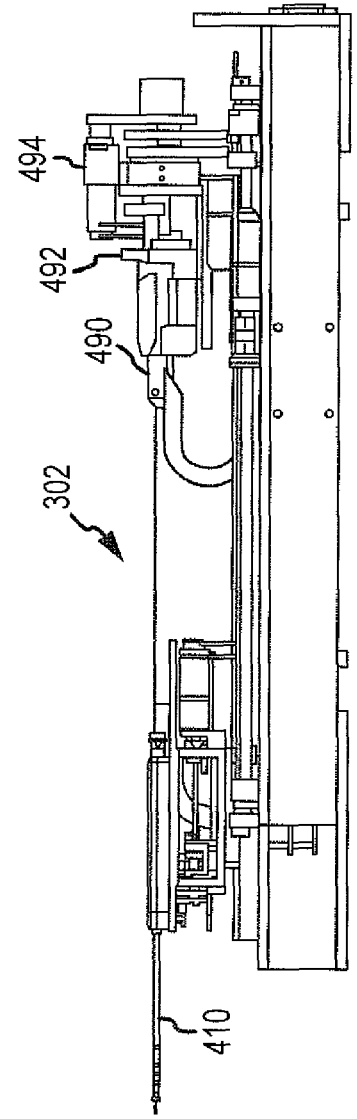

Referring to FIGS. 1-3*m*, particularly FIGS. 3*j*-3*m*, robotic catheter manipulator assembly 302 may be usable with a robotic catheter rotatable device cartridge 490, described in detail in commonly owned and copending application titled "Robotic Catheter Rotatable Device Cartridge." As shown in FIG. 3*m*, manipulator base 308 may be replaced with a robotic catheter rotatable drive head 492 and a robotic catheter rotatable drive mechanism 494, described in detail in commonly owned and copending application titled "Robotic Catheter Rotatable Drive Mechanism."

Referring to FIGS. 1 and 5*a*-5*e*, catheter and sheath cartridges 402, 404 will be described in detail.

As briefly discussed above, robotic catheter system 10 may include one or more cartridges 400, with manipulator 302 including at least two cartridges 402, 404, each of which may be respectively designed to control the distal movement of either the catheter or the sheath. With respect to catheter cartridge 402, catheter 406 may be substantially connected or affixed to cartridge 402, so that advancement of cartridge 402 correspondingly advances catheter 406, and retraction of the cartridge retracts the catheter. As further shown in FIGS. 5*a*-5*e* and discussed above, in an embodiment, each cartridge 402, 404 may include slider blocks (e.g., 412, 414, 416, 418), each rigidly (and independently) connected or affixed to one of a plurality of catheter steering wires (e.g., 420, 422, 424, 426) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 404 may be designed in a similar manner as the catheter cartridge 402, but will typically be configured to provide for the passage of catheter 406. Assembly 302 may include a plurality (e.g., as many as ten or more) of independent driving mechanisms (e.g. motor driven ball screws 324).

For some embodiments, the catheter and sheath cartridge can be designed to be substantially similar, and in that context a reference to either may relate to both. For example, as shown in FIGS. 5*a*-5*e*, the design of the catheter/sheath cartridge may include upper and lower cartridge sections 428, 430, and independent slider blocks 412, 414, 416, 418. The system is not generally limited to specific material selection or formation techniques. However, in an embodiment, the upper and lower cartridge sections 428, 430 may be injection molded using a polycarbonate material. Each slider block 412, 414, 416, 418 may be connected to a separate catheter steering wire 420, 422, 424, 426, and may be formed of a Teflon-like material such as, for example, Delrin AF. When in contact with the cartridge housing portions 428, 430, such Teflon-like slider blocks may maintain a low static and dynamic coefficient of friction and may avoid the need for additional lubrication.

Figure 5A:
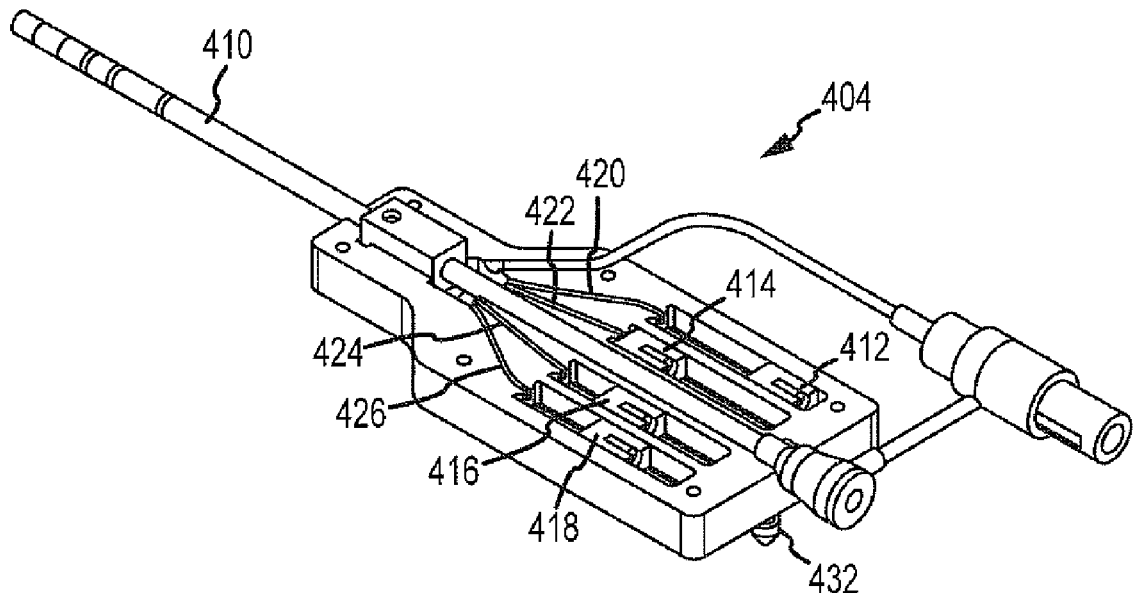
FIGS. 5a-5e are enlarged isometric views of a first embodiment of a robotic catheter device cartridge, with FIG. 3a illustrating an exemplary usage of the robotic catheter device cartridge.
Figure 5B:
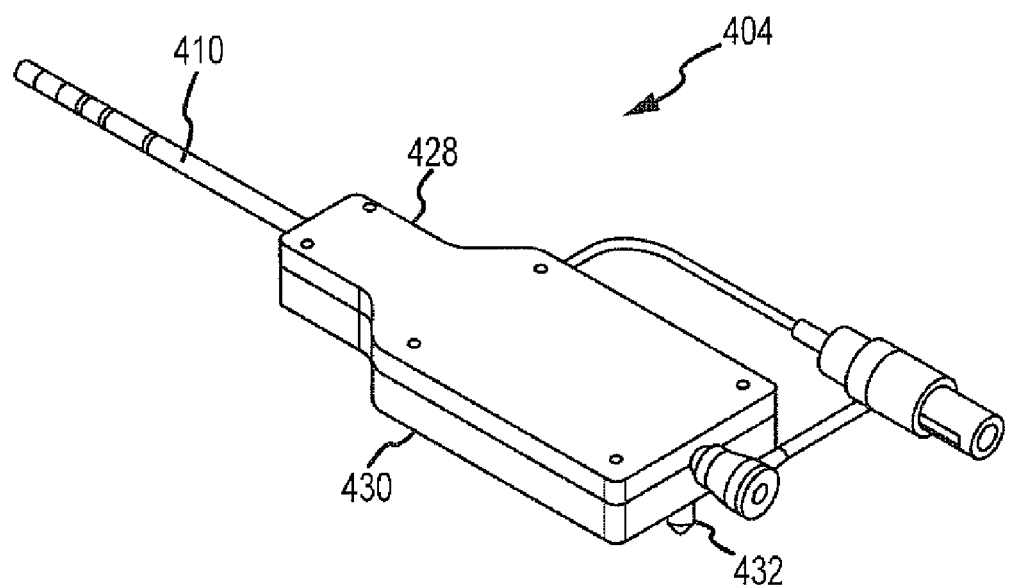
Figure 5C:
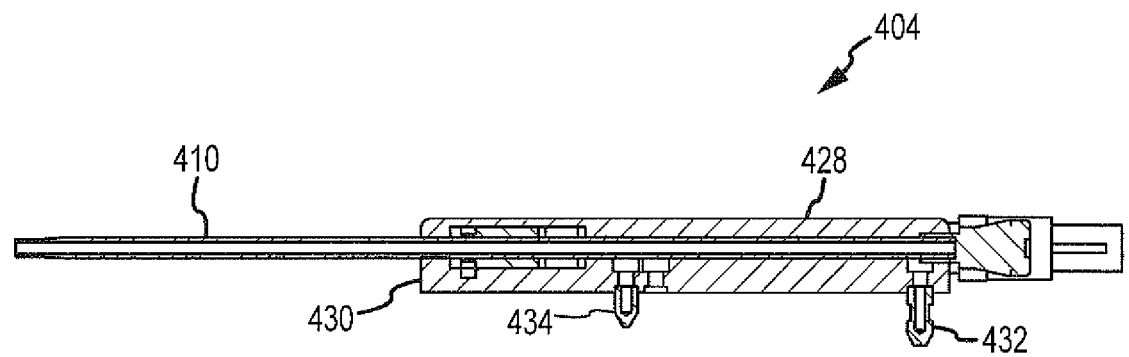
Figure 5D:
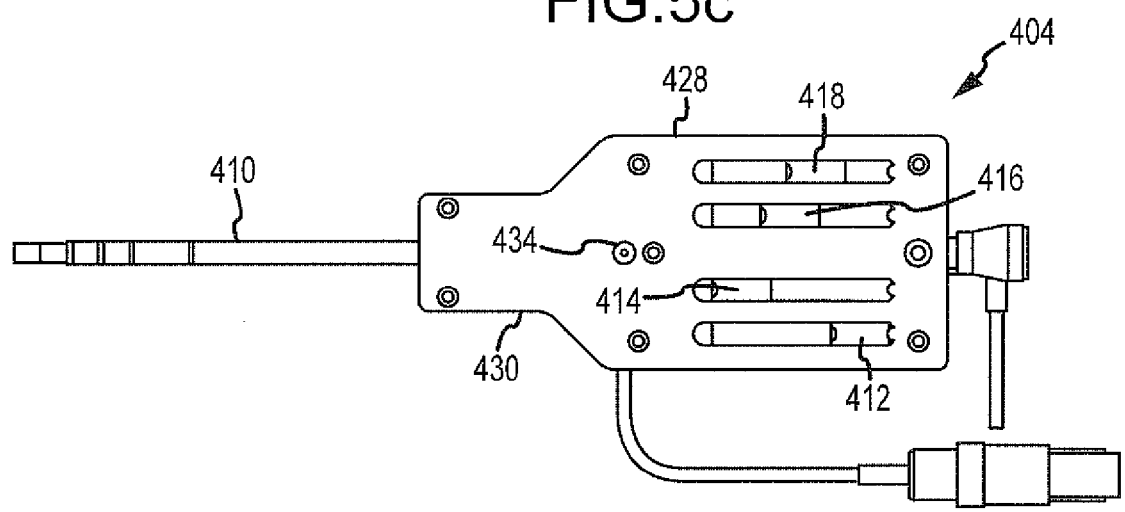
Figure 5E:
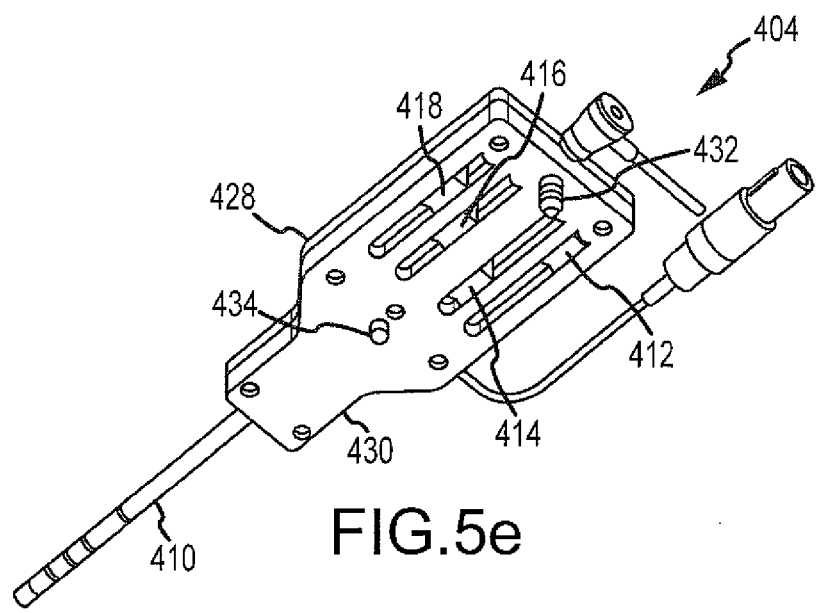
Figure 6A:
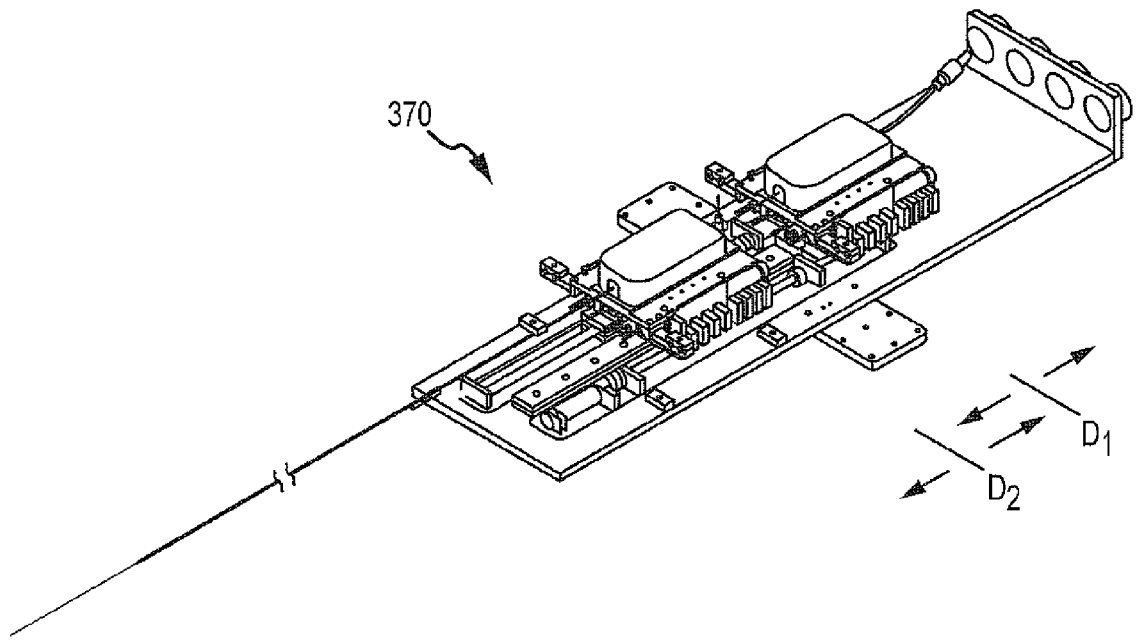
FIGS. 6a-6c are enlarged isometric views of second to fourth embodiments of a robotic catheter manipulator assembly.
Figure 6B:
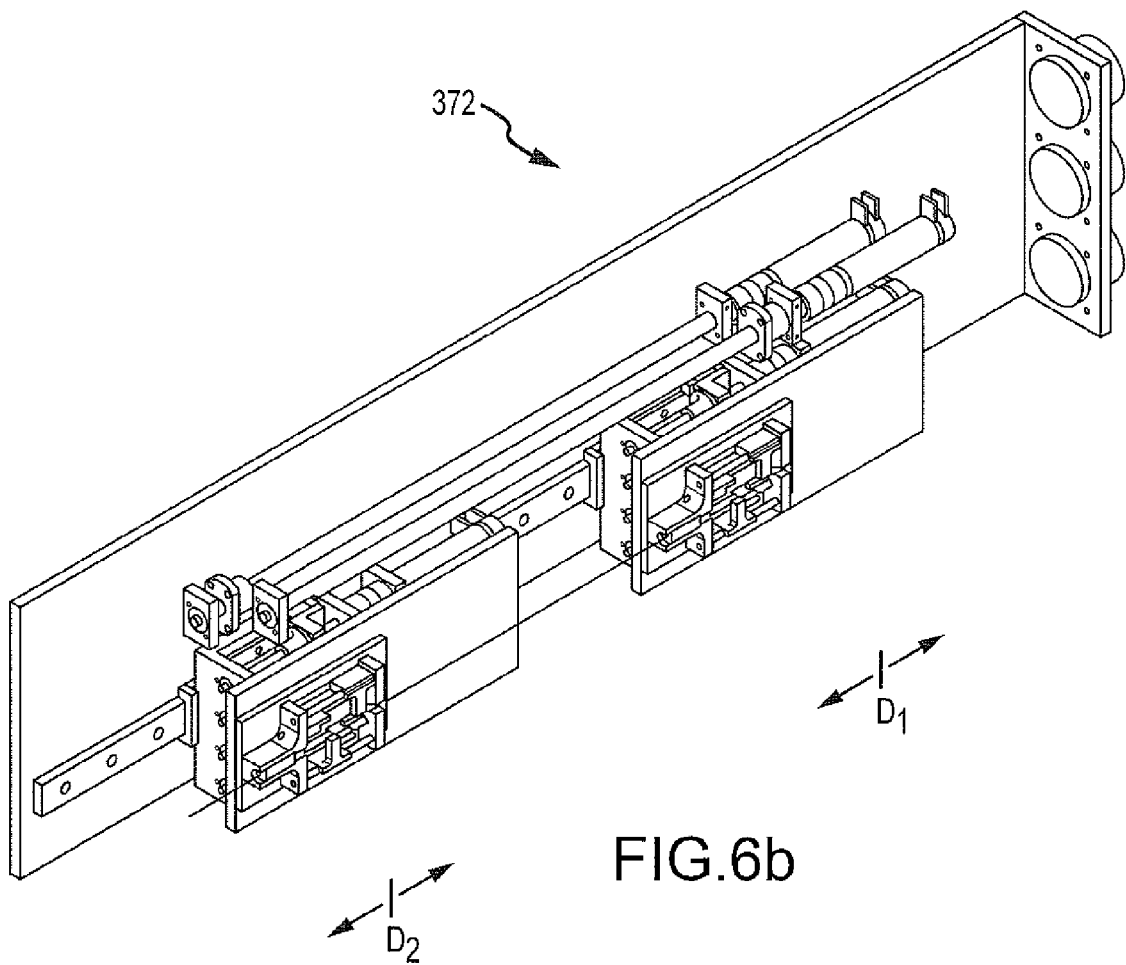
Figure 6C:
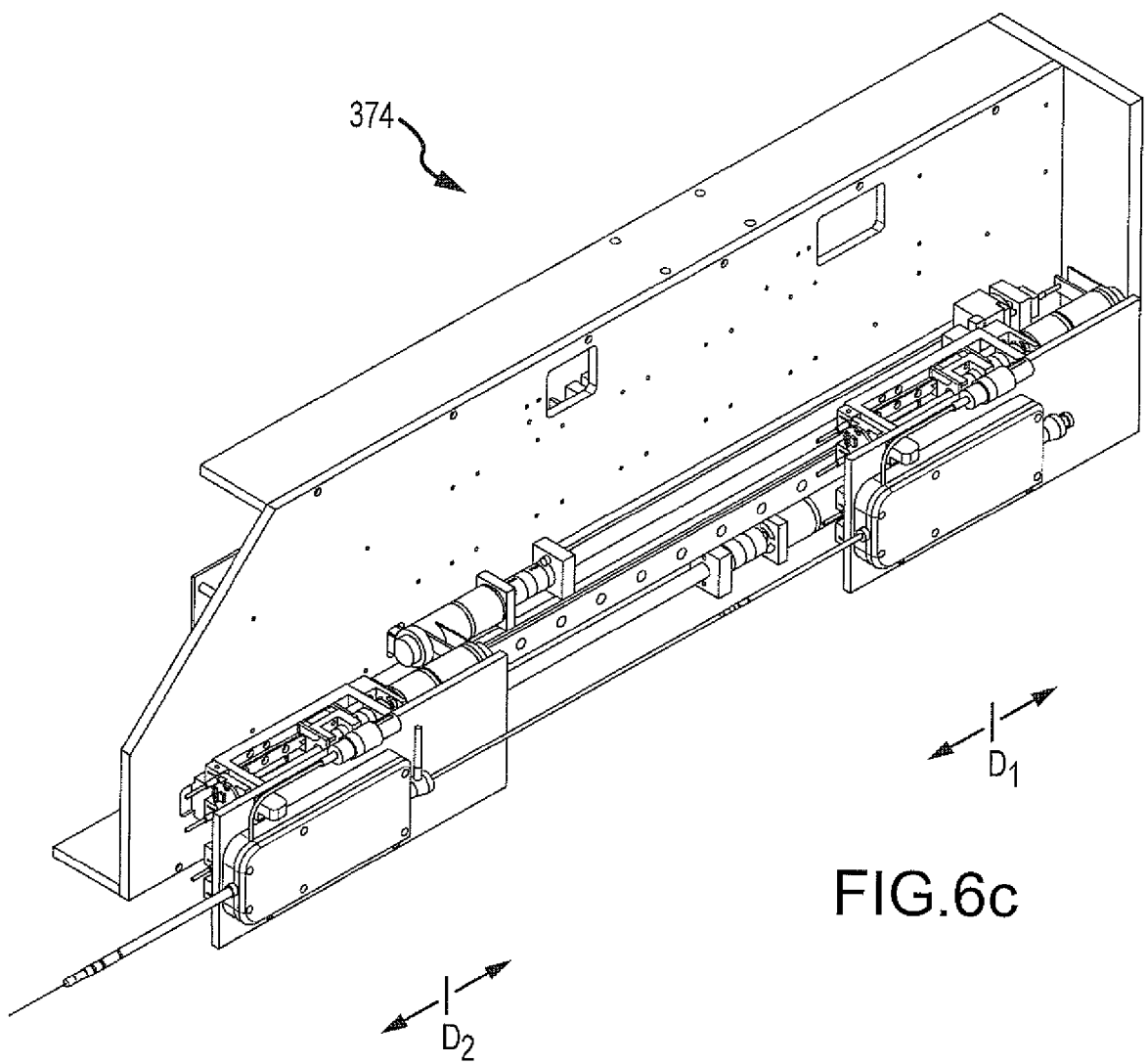

Referring to FIGS. 3*a*-5*e* and as discussed above, catheter and sheath cartridges 402, 404 may be configured to secure or lock down onto respective interconnecting catheter and sheath manipulation bases 308, 310. To couple cartridge 402 (and 404) with base 308 (and 310), one or more locking pins (e.g., 432 in FIGS. 5*a*, 5*d* and 5*e*) on the cartridge may engage one or more mating recesses 360 in the base (see FIG. 4*a*). In an embodiment, such recesses 360 may include an interference lock such as a spring detent or other locking means. In an embodiment, such other locking means may include a physical interference that may require affirmative/positive action by the user to release the cartridge. Such action may include or require actuation of a release lever 362. Additionally, as shown in FIGS. 5*c*, 5*d* and 5*e*, cartridge 402 (and 404) may include one or more locator pins 434 that are configured to passively fit into mating holes on the base (e.g., 364 in FIG. 4*a*).

In an embodiment, a user (e.g. an EP) may first manually position catheter 406 and sheath 410 (with catheter 406 inserted in sheath 410) within the vasculature of a patient. Once the devices are roughly positioned in relation to the heart, the user may then engage or connect (e.g., "snap-in") the catheter cartridge into place on interconnecting/interlocking bases 308, 310 of manipulator assembly 302, for example, by inserting the locking/locating pins 432, 434 of the cartridges into mating holes 360, 364 of respective base 308, 310. When the cartridge is interconnected with the base, each of the plurality of fingers 316, 318, 320 or 322 may fit into recesses formed between the distal edge of slider blocks 412, 414, 416, 418 and a lower portion of the cartridge housing. Such recesses are shown in, for example, FIGS. 5*d* and 5*e*.

Each finger may be designed to be actuated in a proximal direction to correspondingly push each respective slider block. The slider block can be configured to force the finger to self center on its geometry when contact is first made. Such a centering feature may be facilitated by the contact surface of the slider block. For example, as shown in FIGS. 5d and 5e, the slider block may include an engagement surface (e.g., shaped as a semi-cylindrical recess in the forward facing portion). This surface may be configured to mate or communicate with a matching round portion of a corresponding finger.

With sufficiently rigid coupling between each slider block and a corresponding steering wire, pushing a slider block in a proximal direction may cause an attached steering wire to tension and thus laterally deflect the distal end of the catheter and sheath 406, 410. Moreover, in such an embodiment, because there is no rigid connection between each finger and its associated slider block, the manipulator assembly 302 cannot pull the steering wire in a forward direction. That is, when each block is actuated, it is only possible to tension the steering wire. Furthermore, because the push-actuation of each slider block occurs near that block's bottom surface, a moment may be imposed on the block. Because such a moment may increase the likelihood of the block binding during travel, the length of the block may be optimized to reduce or minimize contact forces between the block and the cartridge housing.

The aforementioned electrical handshake between manipulation bases 308, 310 and catheter and sheath cartridges 402, 404 will be described briefly.

Robotic catheter system 10 may be useful for a variety of procedures and in connection with a variety of tools and/or catheters. Such tools and/or catheters may include, without limitation, spiral catheters, ablation catheters, mapping catheters, balloon catheters, needle/dilator tools, cutting tools, cauterizing tools, and/or gripping tools. The system may additionally include a means of identifying the nature and/or type of catheter/tool cartridge that is installed for use, and/or position or connection related information. The system may automatically access/obtain additional information about the cartridge, such as, without limitation, its creation date, serial number, sterilization date, prior uses, etc.

Further, some embodiments of the system may include an ability to "read" or detect the type or nature of the connected cartridge through the use of memory included with the disposable cartridge together with some data/signal transmission means. By way of example, each cartridge may contain a chip (e.g., an EEPROM chip) that can be electrically interfaced by the manipulator head. Such a chip could, for instance, be programmed during the manufacturing process and may electronically store various data, such as the make; model; serial number; creation date; and/or other special features associated with the cartridge or tool. Additionally the chip may contain other worthwhile information, such as an indication of previous use, catheter specific calibration data, and/or any other information that may relate to the safety or performance of the particular device.

In an embodiment, upon interconnecting the cartridge (e.g. 402, 404) with the manipulator head (e.g. 302), a detection means, such as an optical or magnetic sensor, may initially detect the presence of the cartridge. Once presence is detected, the manipulator may energize a chip and initiate data/signal retrieval. Such retrieved data/signal may then be used by the system to control or alter various features and/or displays based on the type of device and/or information provided. While one embodiment may use a chip (e.g., EEPROM), due to its design flexibility, another embodiment may include a wireless transmission device, such as an RFID, which may be employed to facilitate the data storage/transfer instead of, or in addition to a chip.

Referring to FIGS. 1, 2a-2c and 7a-14j generally, various embodiments of manipulator support structure 500 are disclosed.

Figure 7A:
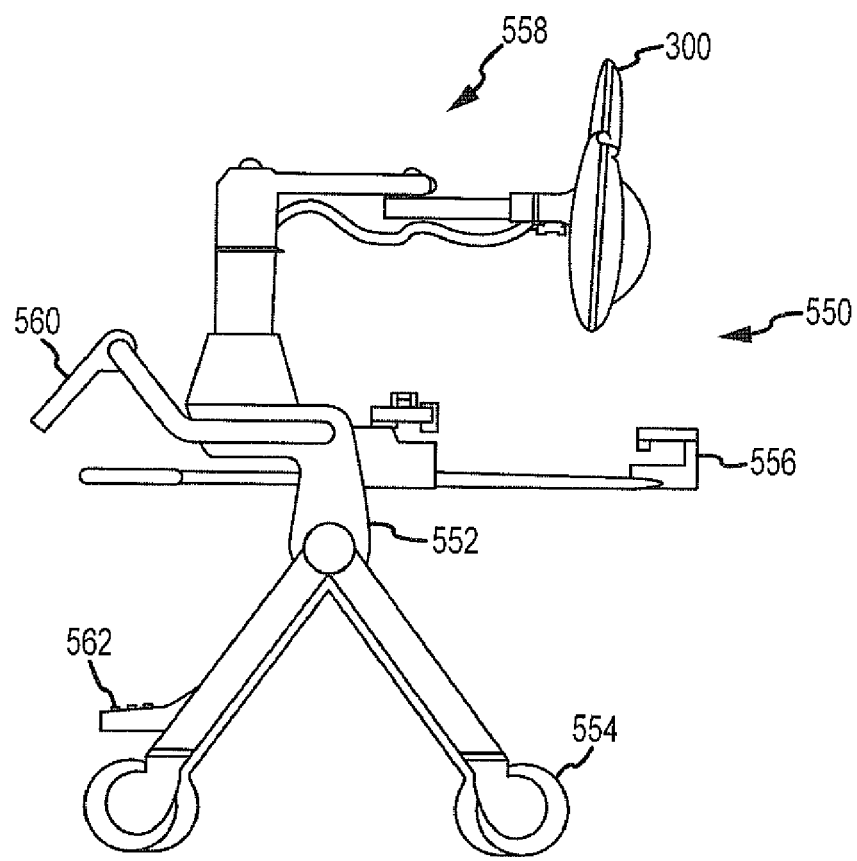
FIGS. 7a and 7b are diagrammatic views of a second embodiment of a robotic catheter manipulator support structure.
Figure 7B:
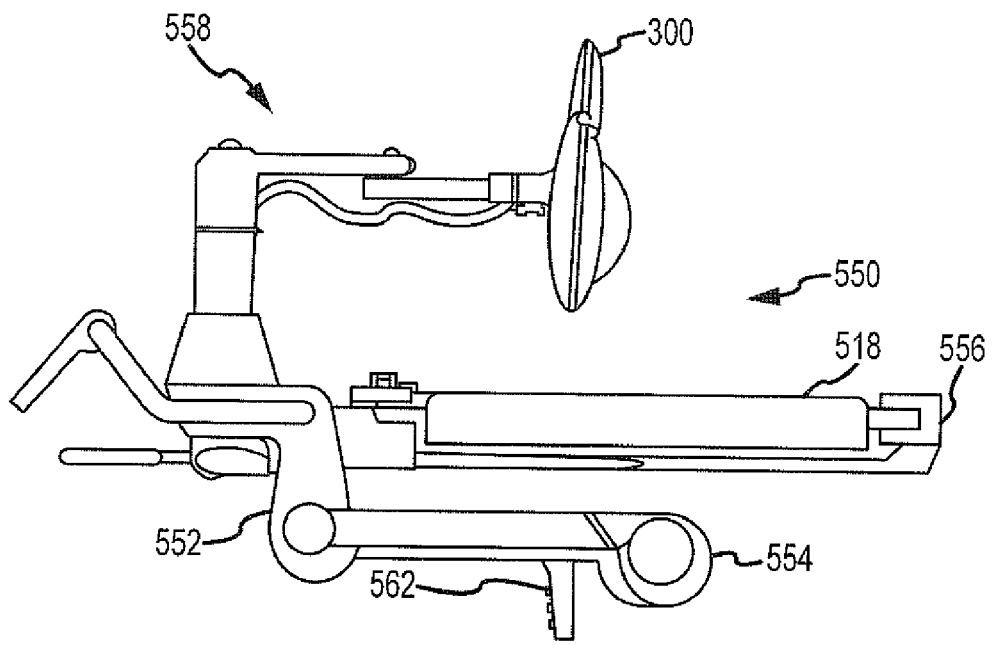

Specifically, referring to FIGS. 1 and 2a-2c, isometric diagrammatic views of a first embodiment of a robotic catheter manipulator support structure 510 (hereinafter "manipulator support structure") are illustrated. Manipulator support structure 510 may generally include a support frame 512 including retractable wheels 514 and attachment assembly 516 for attachment to operation bed 518. A plurality of support linkages 520 may be provided for accurately positioning robotic catheter manipulator assembly 300/302. As shown in FIGS. 7a and 7b for a second embodiment 550 of manipulator support structure, in use, manipulator support structure 510 may be wheeled to operation bed 518 and attached thereto by attachment assembly 516. Thereafter, wheels 514 may be retracted as shown in FIG. 7b.

Referring to FIGS. 7a and 7b, isometric diagrammatic views of the second embodiment of a manipulator support structure 550 are illustrated. Manipulator support structure 550 may generally include a support frame 552 including retractable wheels 554 and attachment assembly 556 for attachment to operation bed 518. A plurality of support linkages 558 may be provided for accurately positioning robotic catheter manipulator assembly 300. As shown in FIG. 7a, a handle 560 may be provided for assisting a user with extending attachment assembly 556 to an opposite side of bed 518. As shown in FIGS. 7a and 7b, in use, manipulator support structure 550 may be wheeled to operation bed 518 and attached thereto by attachment assembly 556. Thereafter, wheels 554 may be pivoted upwards upon release by a steppedal system 562 to be positioned out of the path of operating personnel.

Referring to FIGS. 8a-8c, isometric and related diagrammatic views of a third embodiment of a manipulator support structure 600, and various components thereof are illustrated. Manipulator support structure 600 may generally include a portable unit 602 for transportation of manipulator support structure 600 and its related components. Structure 600 may include attachment assembly 604 for attachment to operation bed 518, and a plurality of support linkages 606 for accurately positioning robotic catheter manipulator assembly 300. Referring to FIGS. 8a and 8b, in use, manipulator support structure 600 may be wheeled to operation bed 518 and attached thereto by attachment assembly 604, and thereafter detached and placed in portable unit 602 for transportation.

Referring to FIGS. 9a and 9b, isometric and related diagrammatic views of a fourth embodiment of a manipulator support structure 650 are illustrated. Manipulator support structure 650 may generally include a track mounted unit 652 for movement of manipulator support structure 650 and its related components. Structure 650 may include attachment assembly 654 for attachment to ceiling or otherwise mounted track 656, and a plurality of support linkages 658 for accurately positioning robotic catheter manipulator assembly 300. Referring to FIGS. 9a and 9b, in use, manipulator support structure 650 may be positioned relative to operation bed 518 and locked in position during use, and moved out of the use position or otherwise re-configured to a stowed position by re-positioning of support linkages 658. As shown in FIG. 9b, manipulator support structure may be moved generally horizontally and vertically for positioning and removal from the area of operation bed 518.

Referring to FIGS. 10a-10c, isometric and related diagrammatic views of a fifth embodiment of a manipulator support structure 700 are illustrated. Manipulator support structure 700 may generally include a fixed unit 702 for movement of manipulator support structure 700 and its related components. Structure 700 may include attachment assembly 704 for attachment to the floor, and a plurality of support linkages 706 for accurately positioning robotic catheter manipulator assembly 300. In use, manipulator support structure 700 may be mounted in place relative to operation bed 518, or alternatively, bed 518 may be positioned adjacent structure 700. After use, structure 700 may be re-configured to a stowed position by re-positioning of support linkages 706.

Figure 11C:
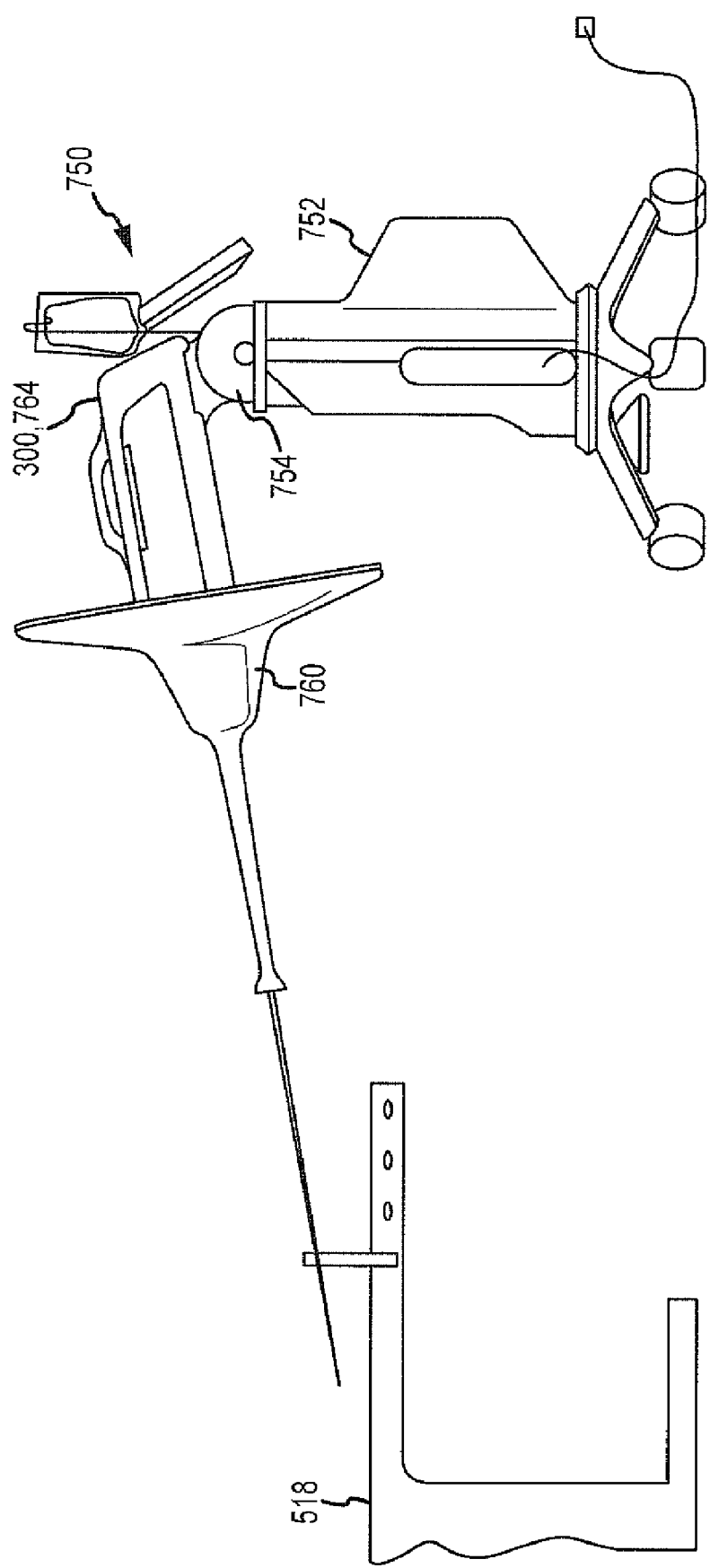
Figure 11D:
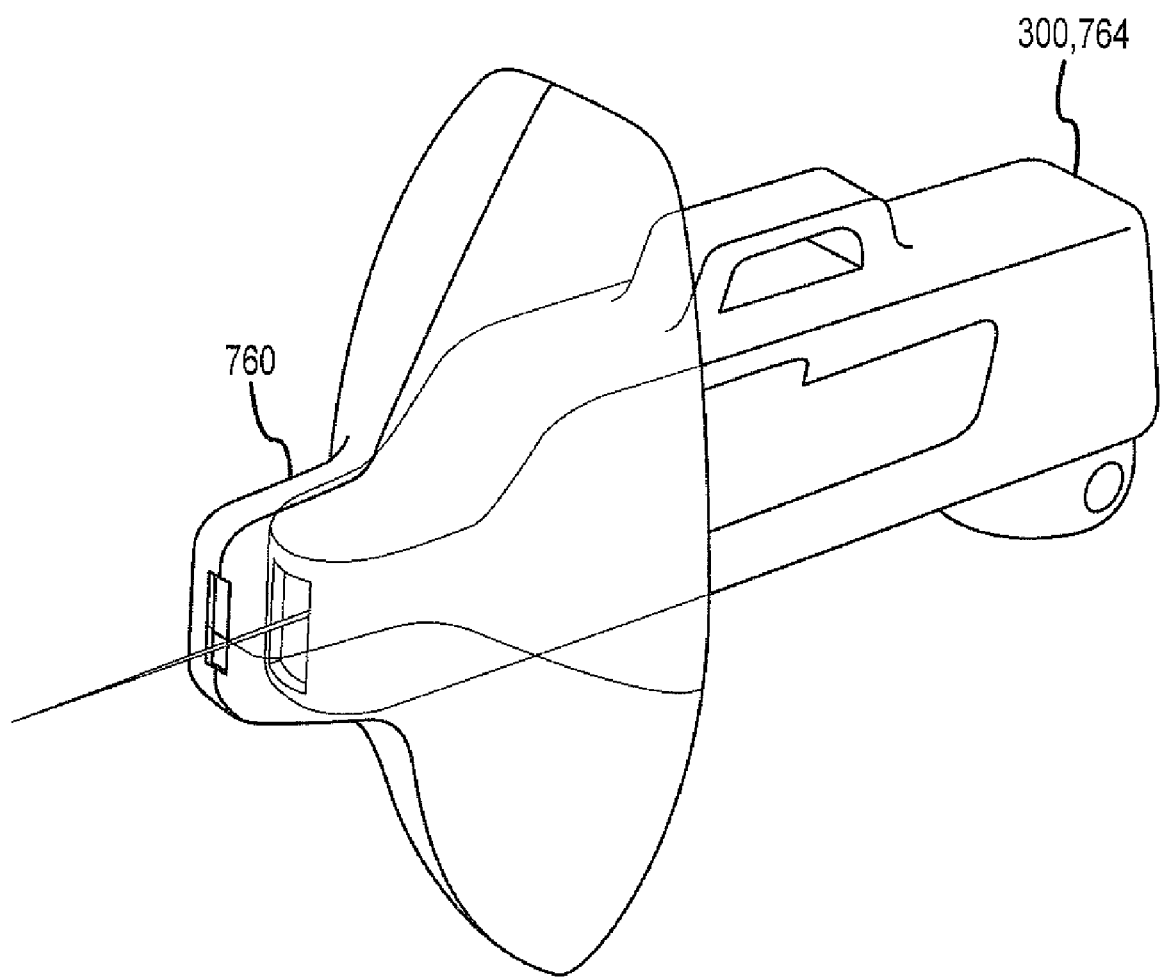
Figure 11E:
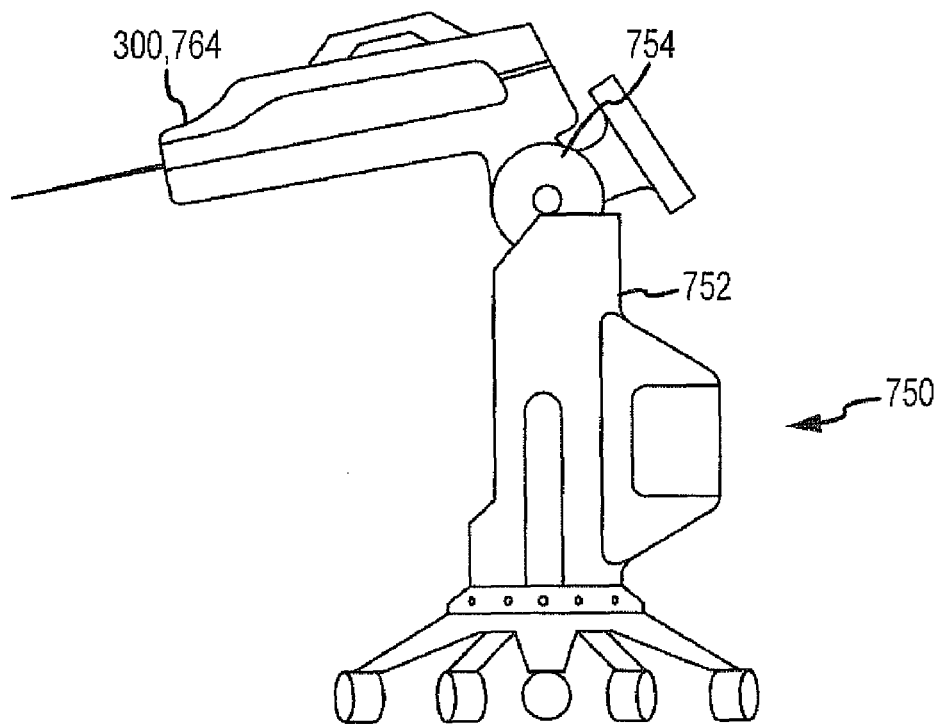

Referring to FIGS. 11a-11h, isometric and related diagrammatic views of a sixth embodiment of a manipulator support structure 750, and various components thereof are illustrated. Manipulator support structure 750 may generally include a portable unit 752 for movement of manipulator support structure 750 and its related components. Structure 750 may include a pivotable support 754 for accurately positioning robotic catheter manipulator assembly 300. Pivotable support 754 may be pivotable about generally vertical and horizontal axis 756, 758. As shown in FIGS. 11c and 11d, a disposable sterile shield 760 may be positionable on robotic catheter manipulator assembly 300. Sterile shield 760 may isolate the manipulator from a sterile field in an operating room/EP lab environment. The sterile interface may optionally include a sealing material or component, such as a pliable gasket-type material, to allow the manipulator fingers (e.g. 316, 318, 320 and 322) to interact with the cartridge (e.g. 402, 404) without operational interference, but while maintaining a necessary degree of sterility. Such a barrier or drape may permit the manipulator to be re-used without requiring additional sterilization.

Figure 11F:
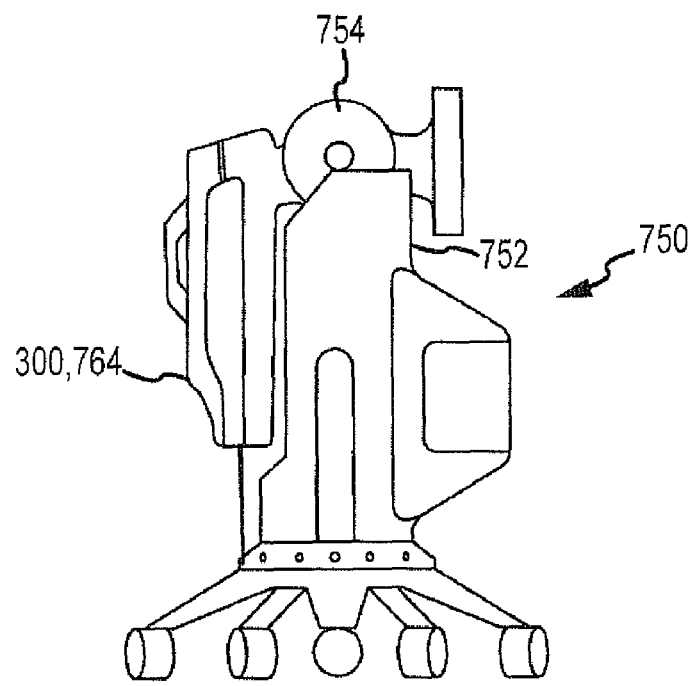
Figure 11G:
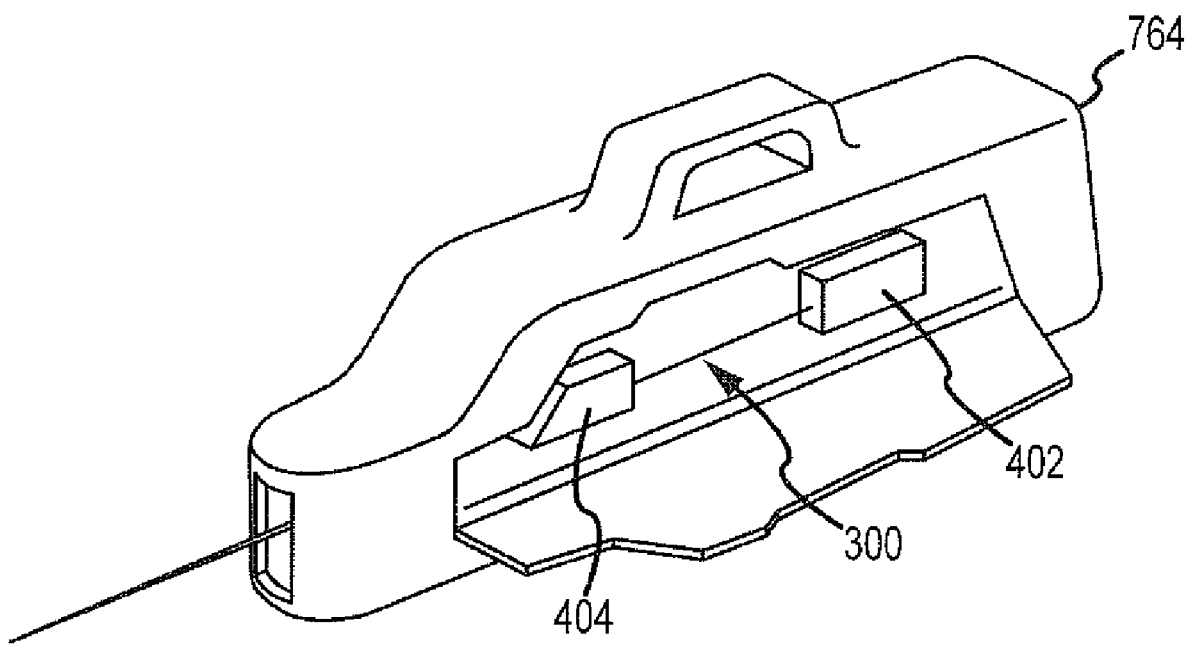
Figure 11H:
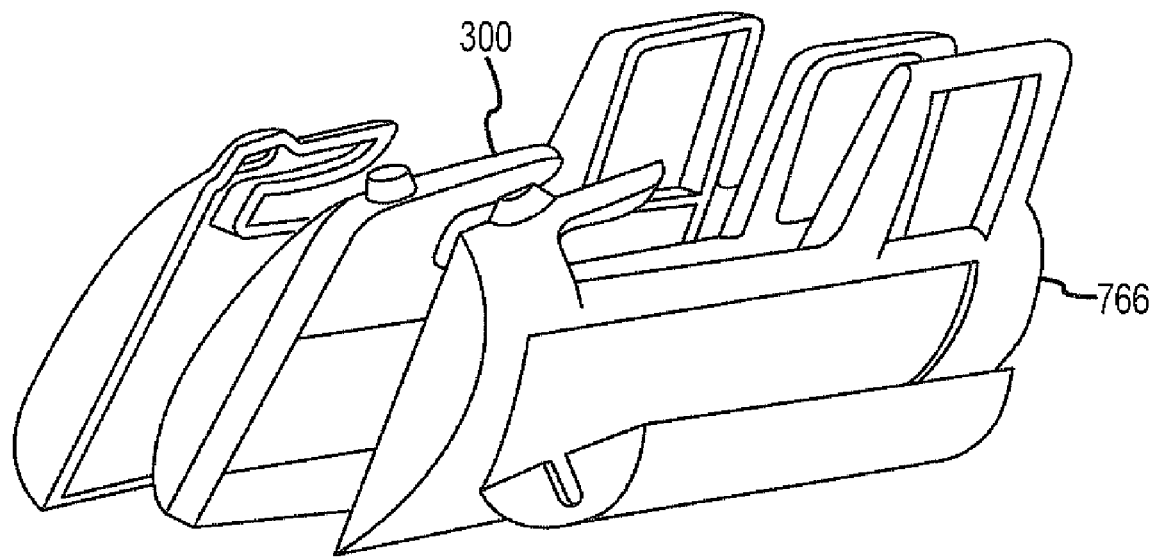

Referring to FIGS. 11a-11h, in use, manipulator support structure 750 may be placed next to operation bed 518, or alternatively, bed 518 may be positioned adjacent structure 750, with an appropriate sterile shield 760 disposed on robotic catheter manipulator assembly 300. After use, structure 750 may be collapsed as shown in FIG. 11f. As shown in FIG. 11g, cartridges 402, 404 may be attached or replaced as needed by access via a hinged cover of manipulator case 764, or alternatively, as shown in FIG. 11h, a sectioned case 766 may be provided for cartridge replacement or access to robotic catheter manipulator assembly 300.

Figure 12A:
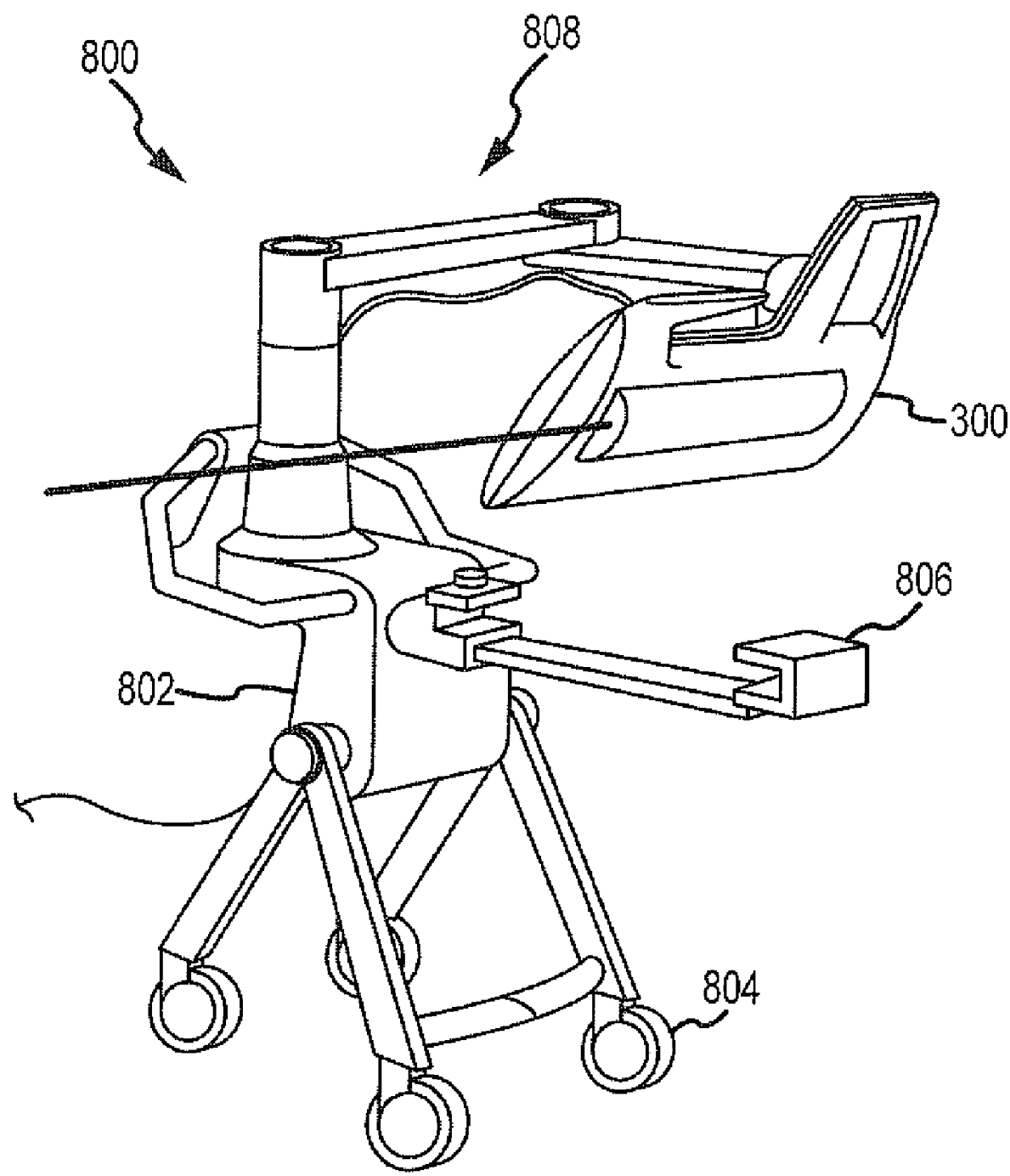
FIGS. 12a-12c are isometric and related diagrammatic views of a seventh embodiment of a robotic catheter manipulator support structure.
Figure 12B:
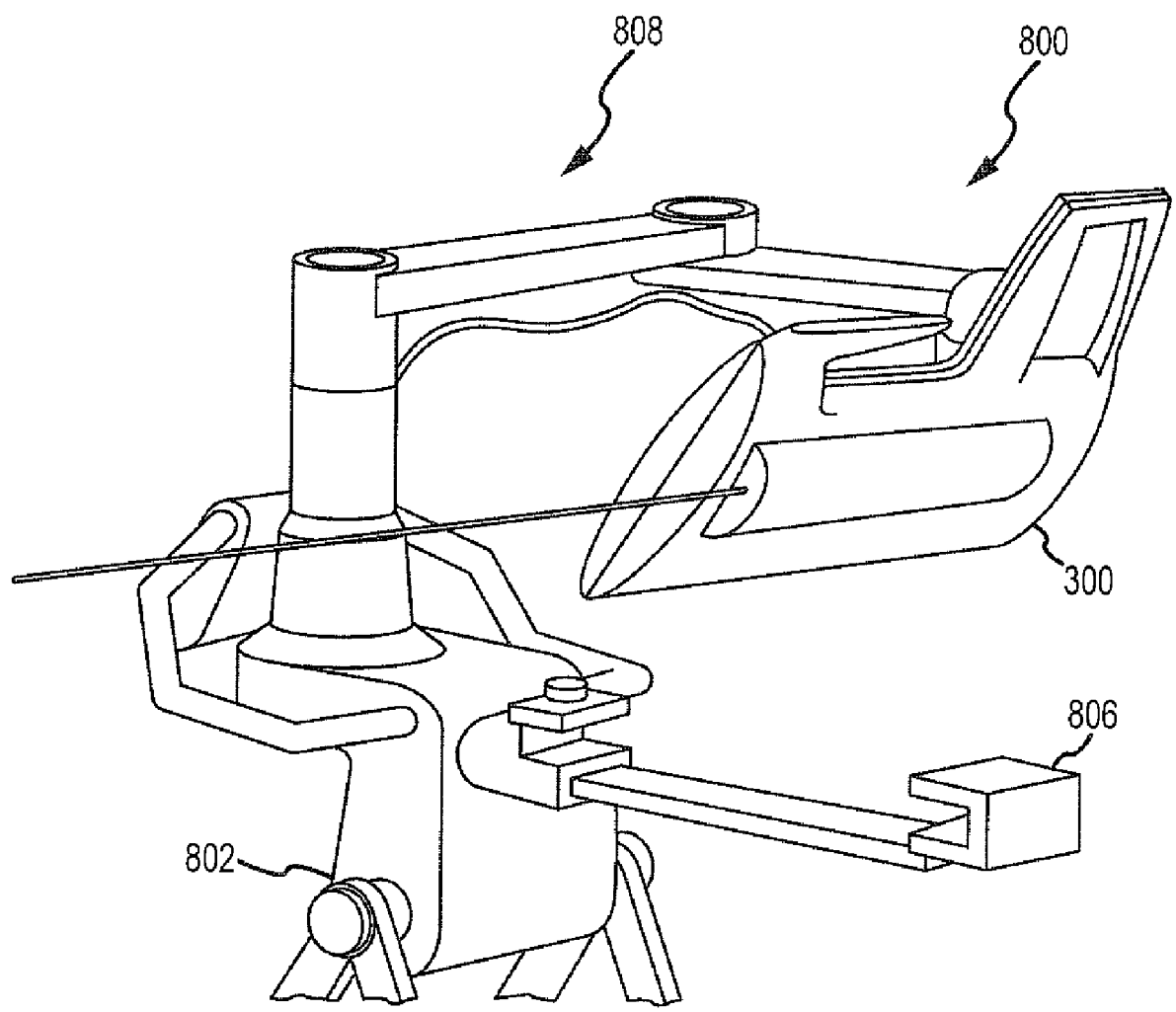
Figure 12C:
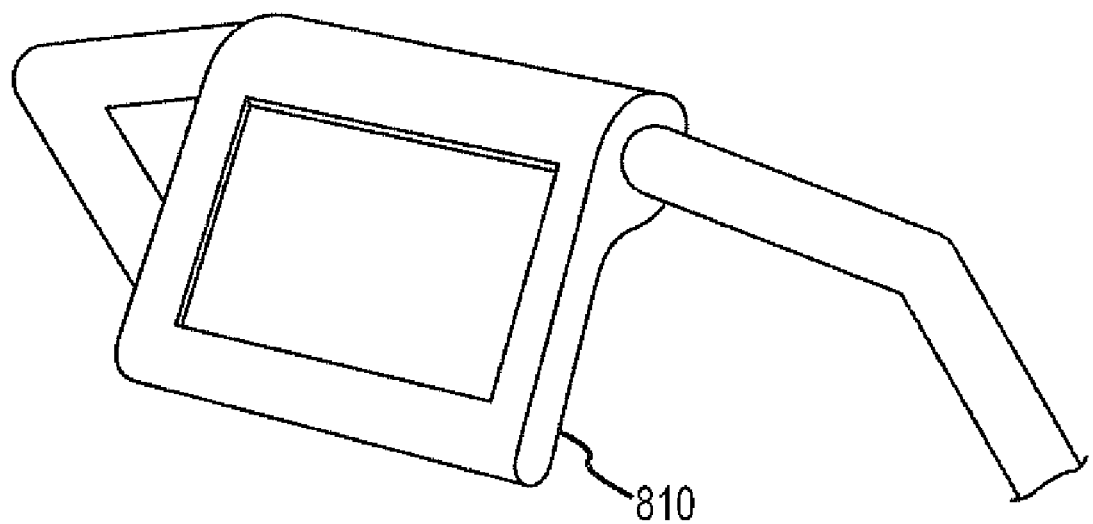

Referring to FIGS. 12a-12c, isometric and related diagrammatic views of a seventh embodiment of a manipulator support structure 800, and related components are illustrated. Manipulator support structure 800 may be similar in design to support structure 550 of FIGS. 7a and 7b. Manipulator support structure 800 may generally include a support frame 802 including wheels 804 and attachment assembly 806 for attachment to operation bed 518. A plurality of support linkages 808 may be provided for accurately positioning robotic catheter manipulator assembly 300. As shown in FIG. 12c, a touch-screen interface 810 may be provided for controlling operation of robotic catheter manipulator assembly 300. As shown in FIGS. 12a and 12b, and FIGS. 7a and 7b for support structure 550, in use, manipulator support structure 800 may be wheeled to operation bed 518 and attached thereto by attachment assembly 806.

Figure 13B:
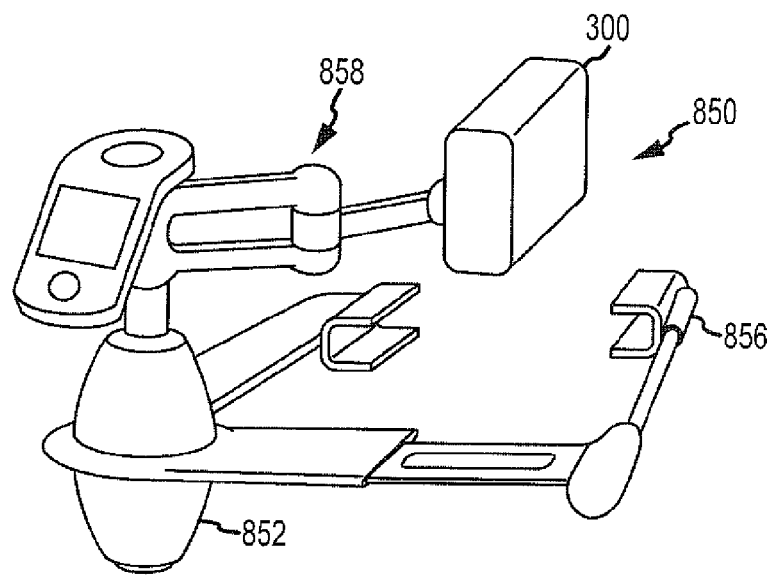
FIGS. 13a-13o are isometric and related diagrammatic views of a eighth embodiment of a robotic catheter manipulator support structure.
Figure 13C:
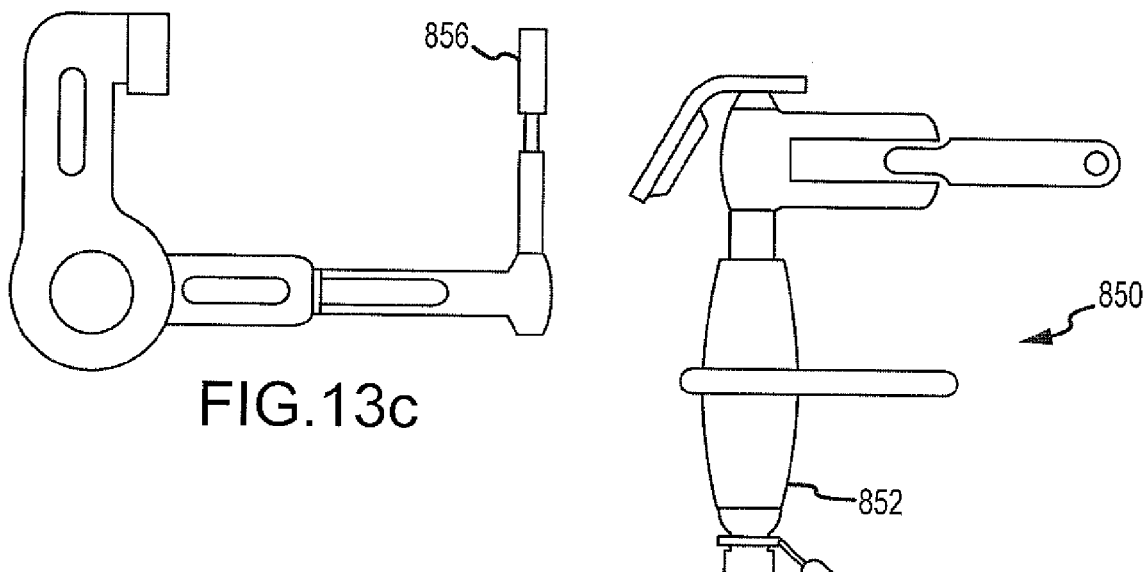
Figure 13A:
Figure 13D:
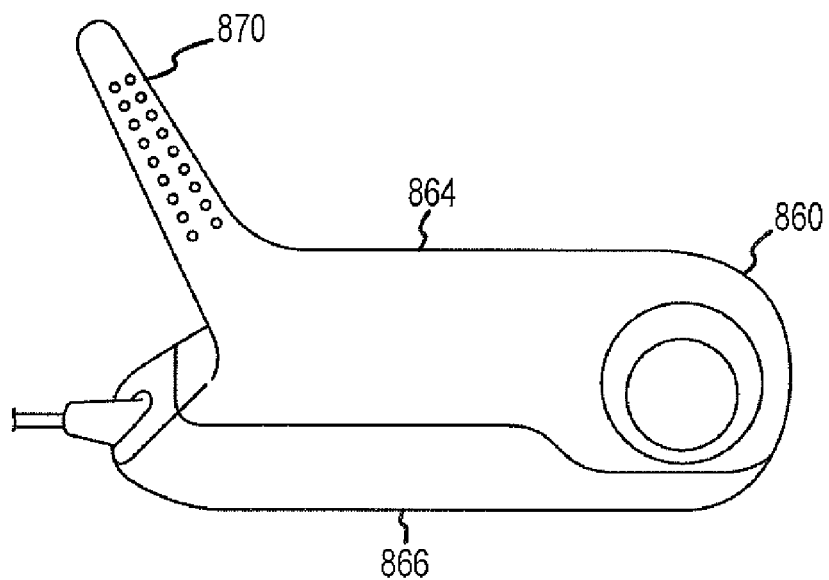
Figure 13E:
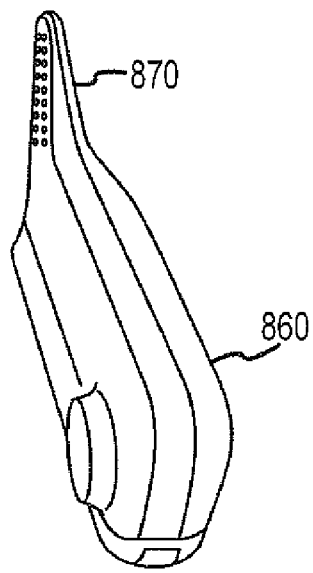
Figure 13F:
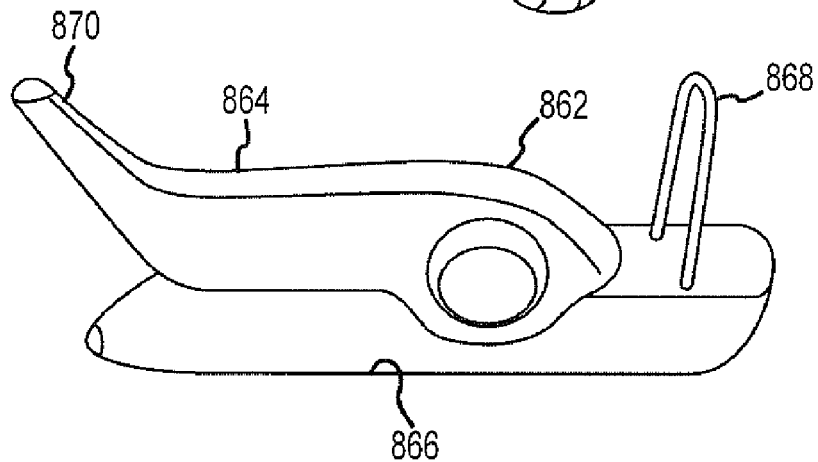
Figure 13G:
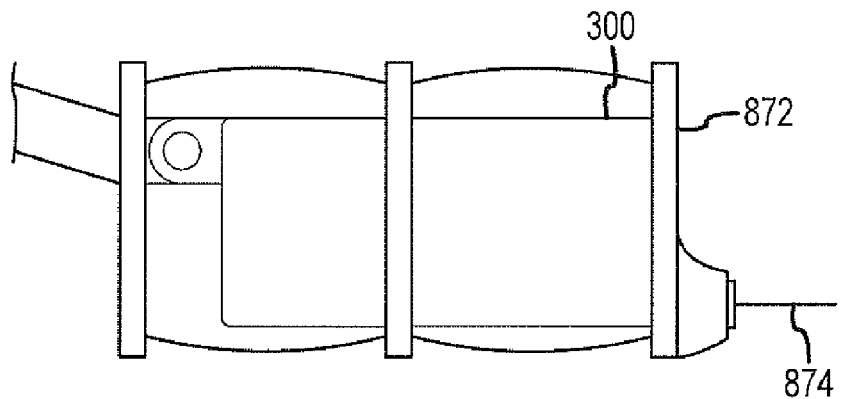
Figure 13H:
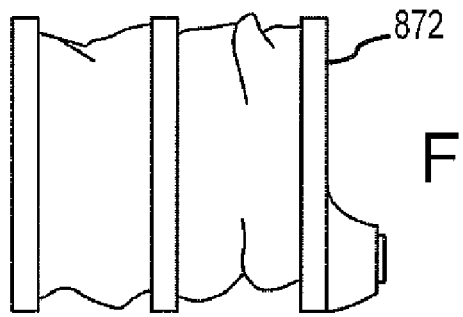
Figure 13I:
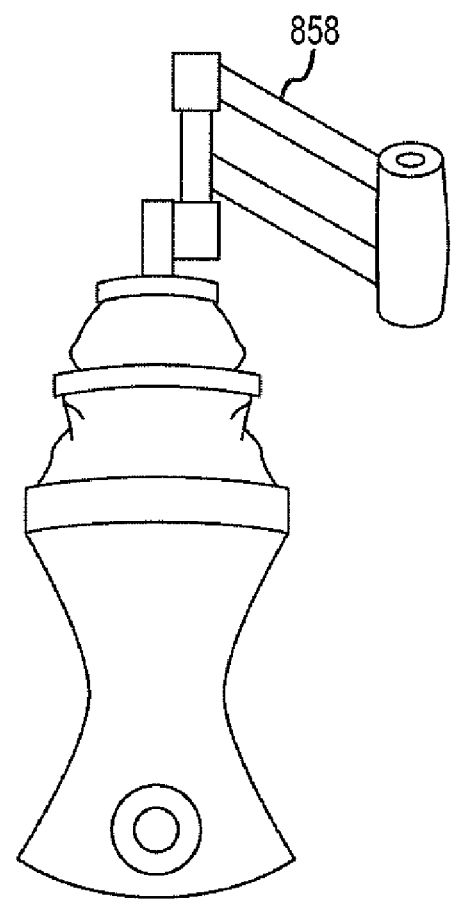
Figure 13J:
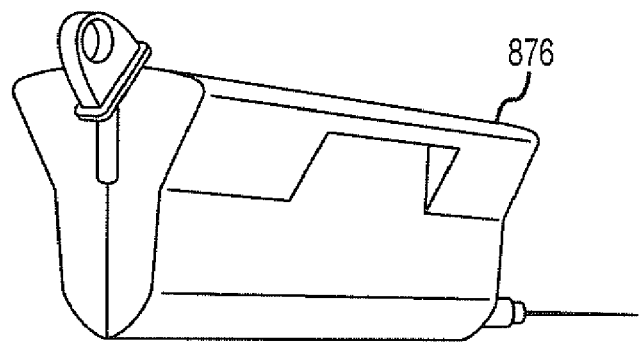
Figure 13K:
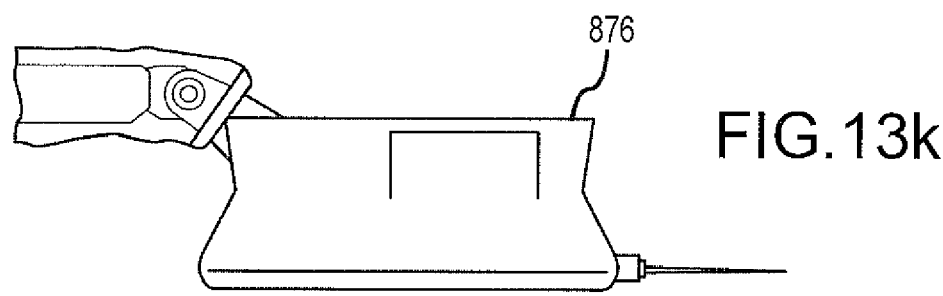
Figure 13N:
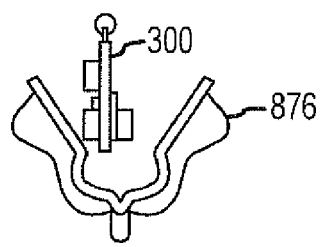
Figure 13L:
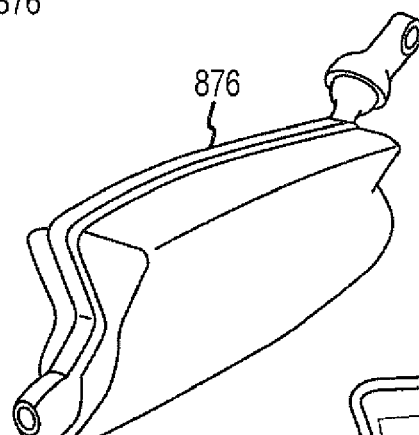
Figure 13M:
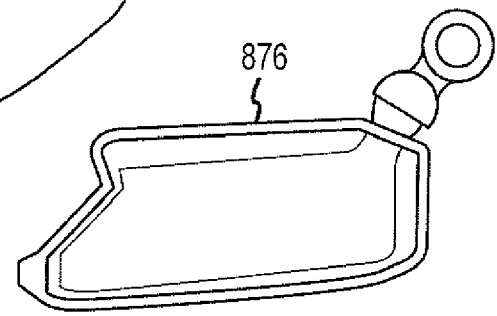
Figure 13O:
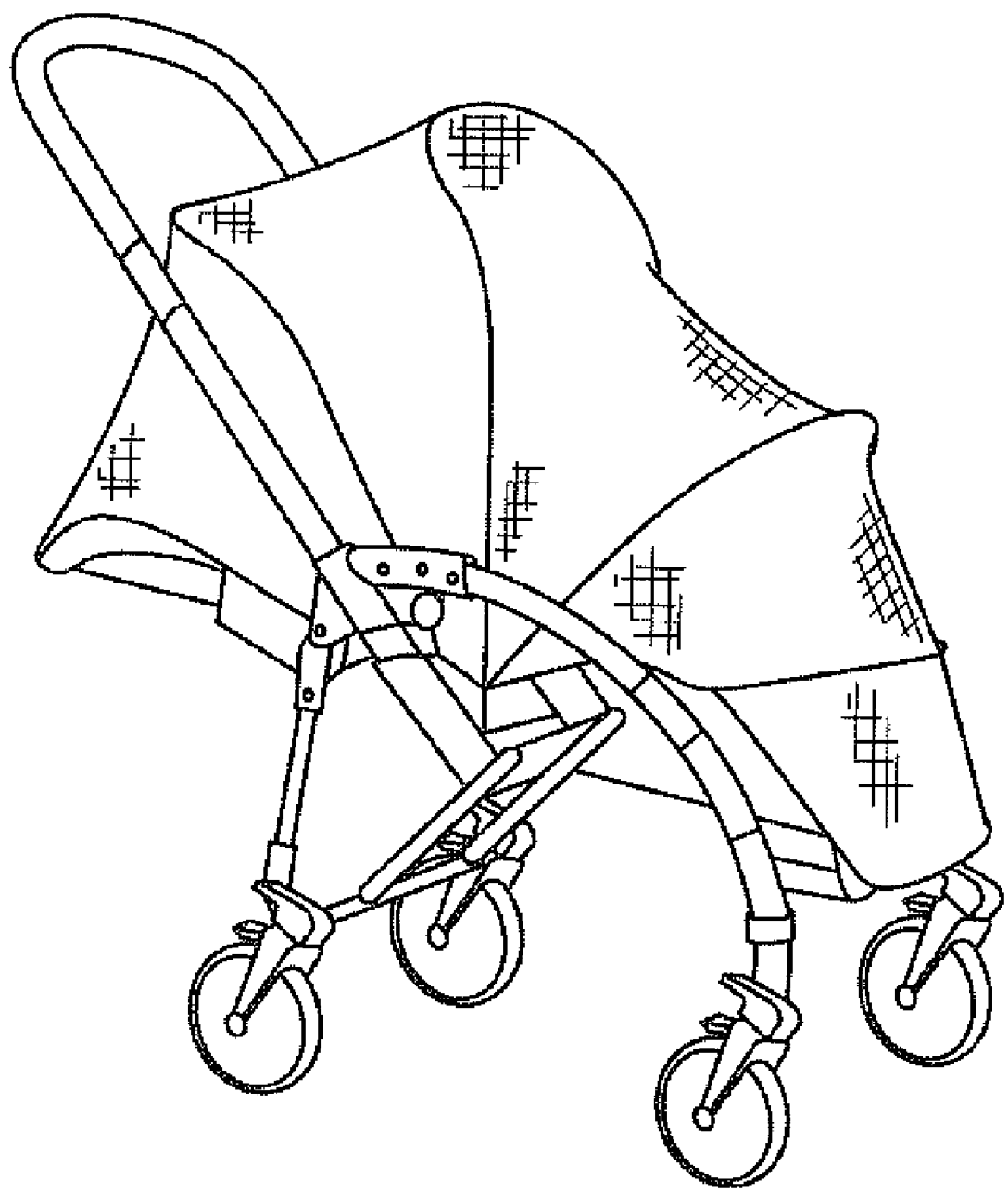

Referring to FIGS. 13a-13o, isometric and related diagrammatic views of an eighth embodiment of a manipulator support structure 850, and related components are illustrated. Manipulator support structure 850 may be similar in design to support structure 550 of FIGS. 7a and 7b. Manipulator support structure 850 may generally include a support frame 852 including wheels 854 and attachment assembly 856 for attachment to operation bed 518. A plurality of support linkages 858 may be provided for accurately positioning robotic catheter manipulator assembly 300. As shown in FIG. 13a, and FIGS. 7a and 7b for support structure 550, in use, manipulator support structure 850 may be wheeled to operation bed 518 and attached thereto by the attachment assembly 856. Referring to FIGS. 13d and 13e, a disposable cover 860 may be provided for robotic catheter manipulator assembly 300, with the cover being used with any of the embodiments of manipulator support structures disclosed herein. As shown in FIGS. 13d-13f, disposable covers 860 and 862 may include a two part top and bottom cover 864, 866, with a saline bag attachment loop 868 and integrated handle 870. As shown in FIGS. 13g and 13h, cover 872 may be collapsible for permitting use of robotic catheter manipulator assembly 300 by exposing catheter/sheath 874. As shown in FIGS. 13j-13n, a cover 876 may be opened and removed to permit unrestrained operation of manipulator assembly 300. As shown in FIG. 13o, another transportation system for the aforementioned manipulator support structures and related components is illustrated.

Figure 14A:
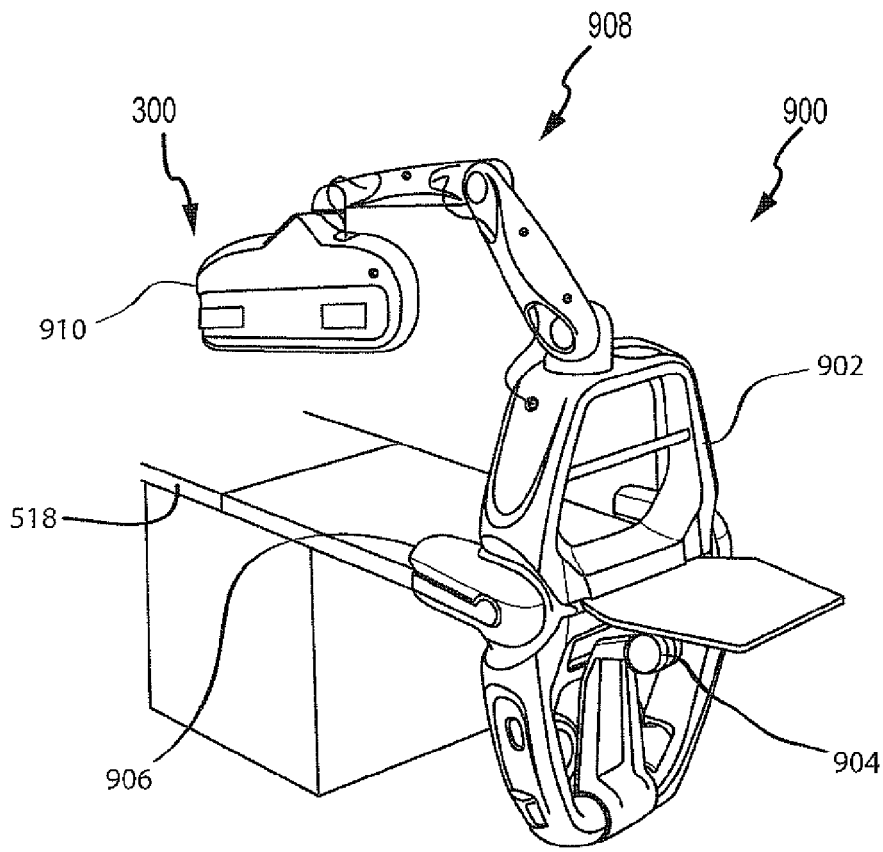
Figure 14B:
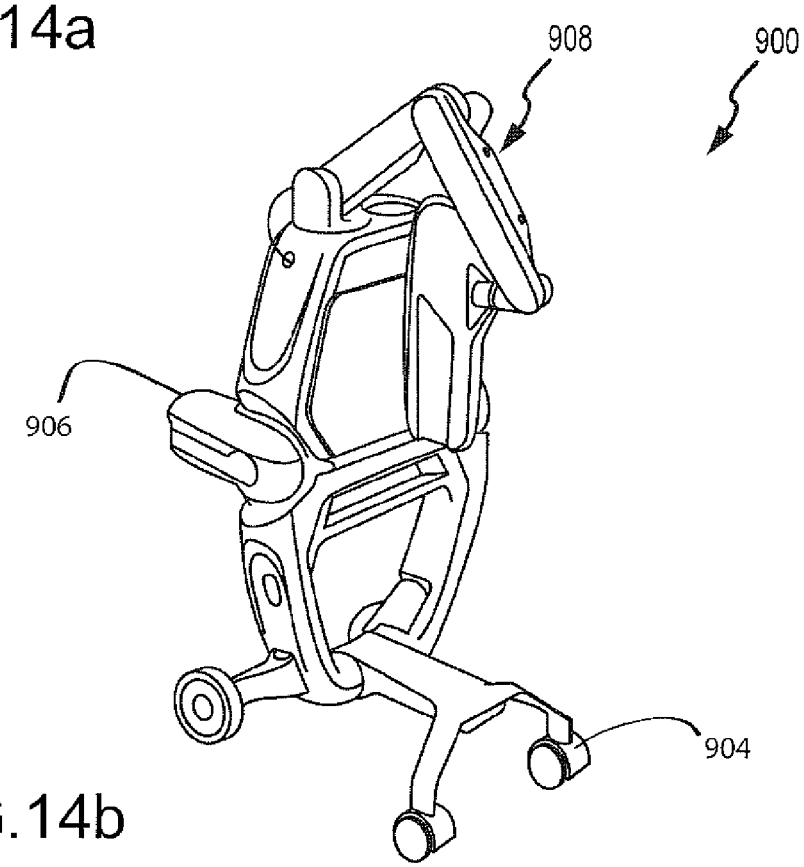

Referring to FIGS. 1 and 14a-14j, isometric diagrammatic views of a ninth embodiment of a manipulator support structure 900 and various components thereof are illustrated. Manipulator support structure 900 may generally include a support frame 902 including retractable wheels 904 and releasable attachment assembly 906 for attachment to operation bed 518. A plurality of support linkages 908 may be provided for accurately positioning robotic catheter manipulator assembly 300. As shown in FIGS. 14a and 14b, manipulator support structure 900 is illustrated as respectively disposed in the use and stowed/transport configurations. As shown in FIGS. 14a and 14b, in use, manipulator support structure 900 may be wheeled to operation bed 518 and attached thereto by attachment assembly 906. Thereafter, wheels 904 may be pivoted upwards upon release by a step-pedal (not shown) to be positioned out of the path of operating personnel.

Figure 14C:
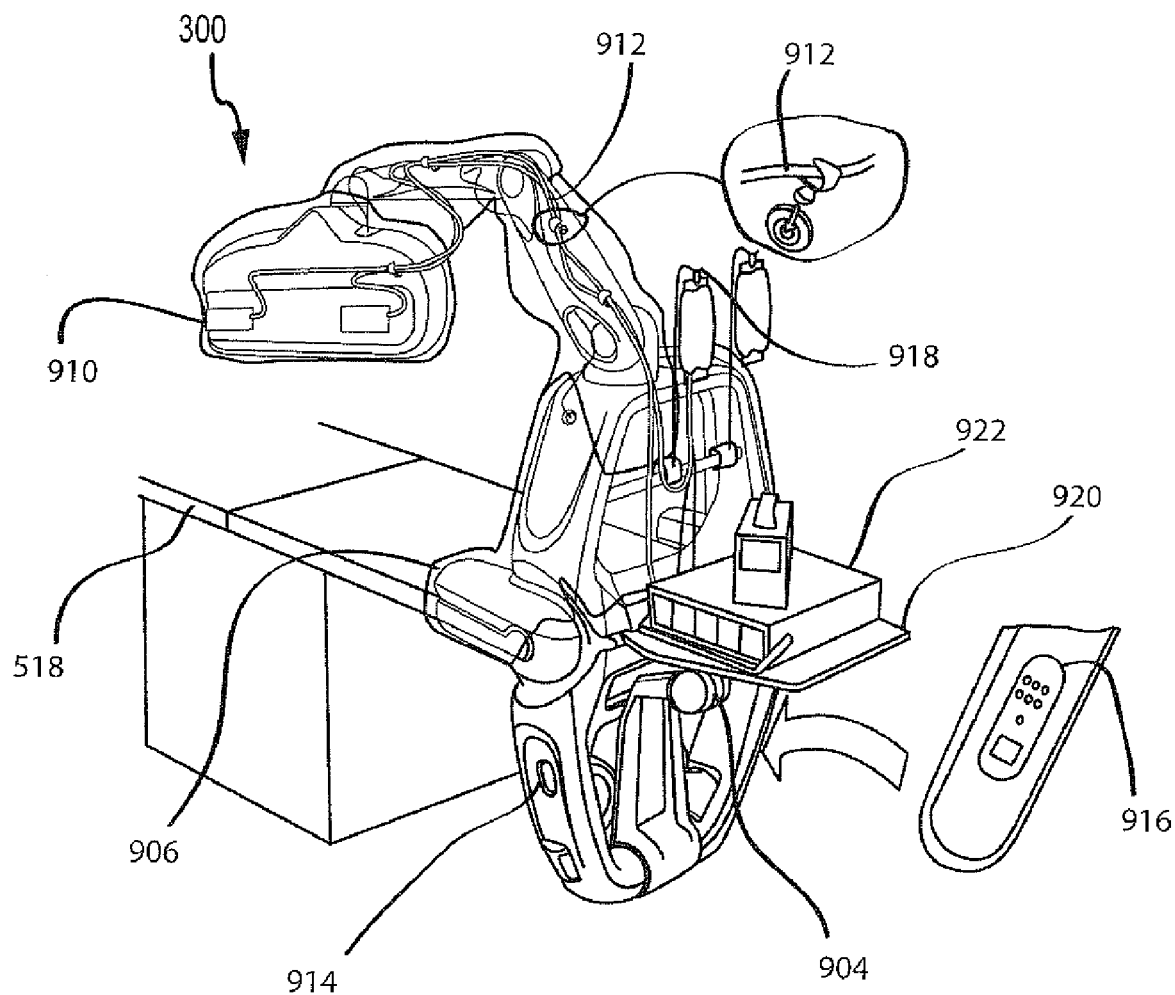

Referring to FIGS. 14a-14c, manipulator support structure 900 may include a sterile cover 910 disposed over manipulator assembly 300. Other components may include irrigation tubes 912, a USB/power connector 914, and a control module 916 including a power port, network port and an EnSite™ system connection. Saline bags may be removably hung at hangers 918, and a foldable shelf 920 may be provided for equipment, such as, a saline pump and/or ablation generator 922.

Figure 14D:
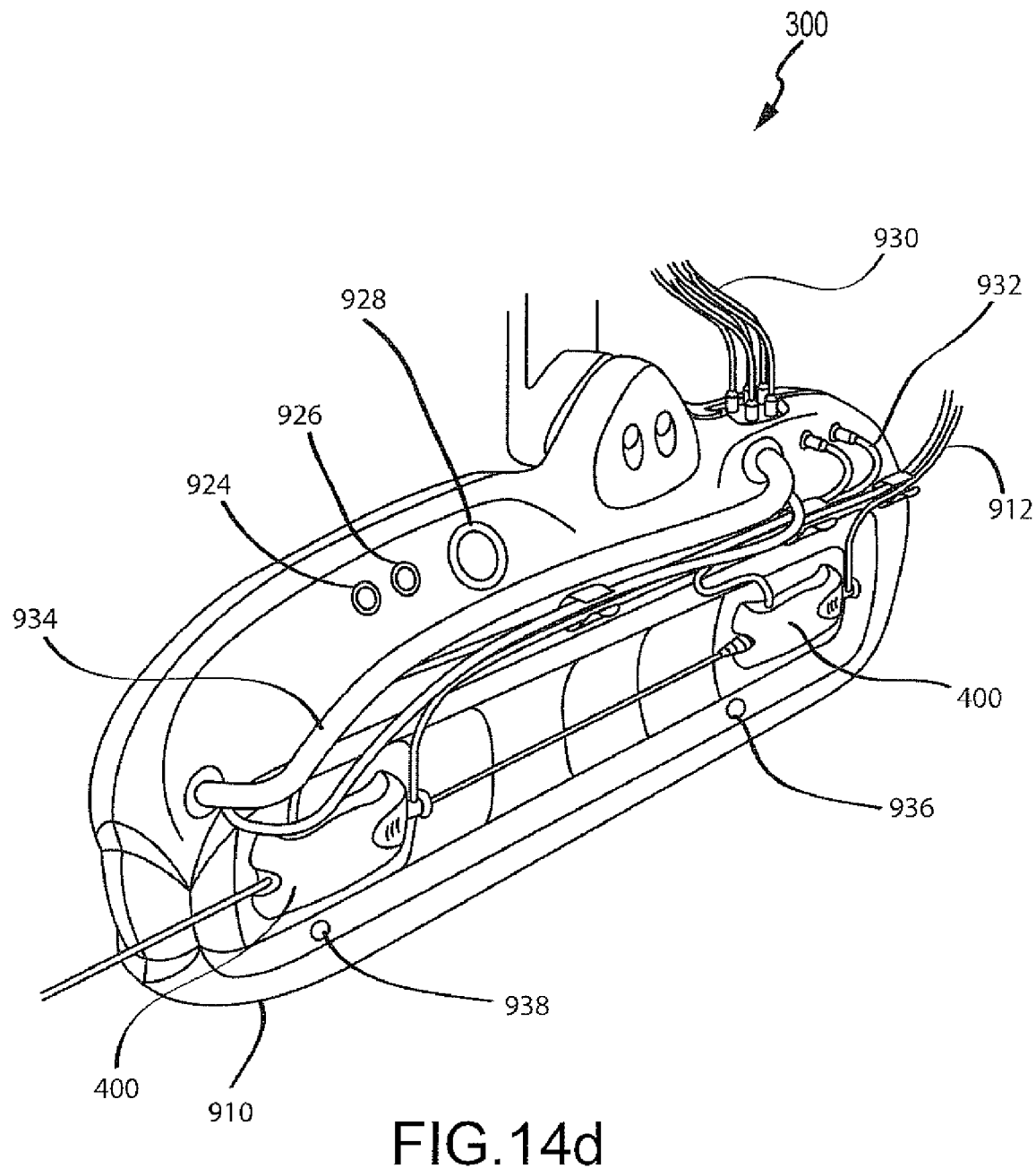
Figure 14E:
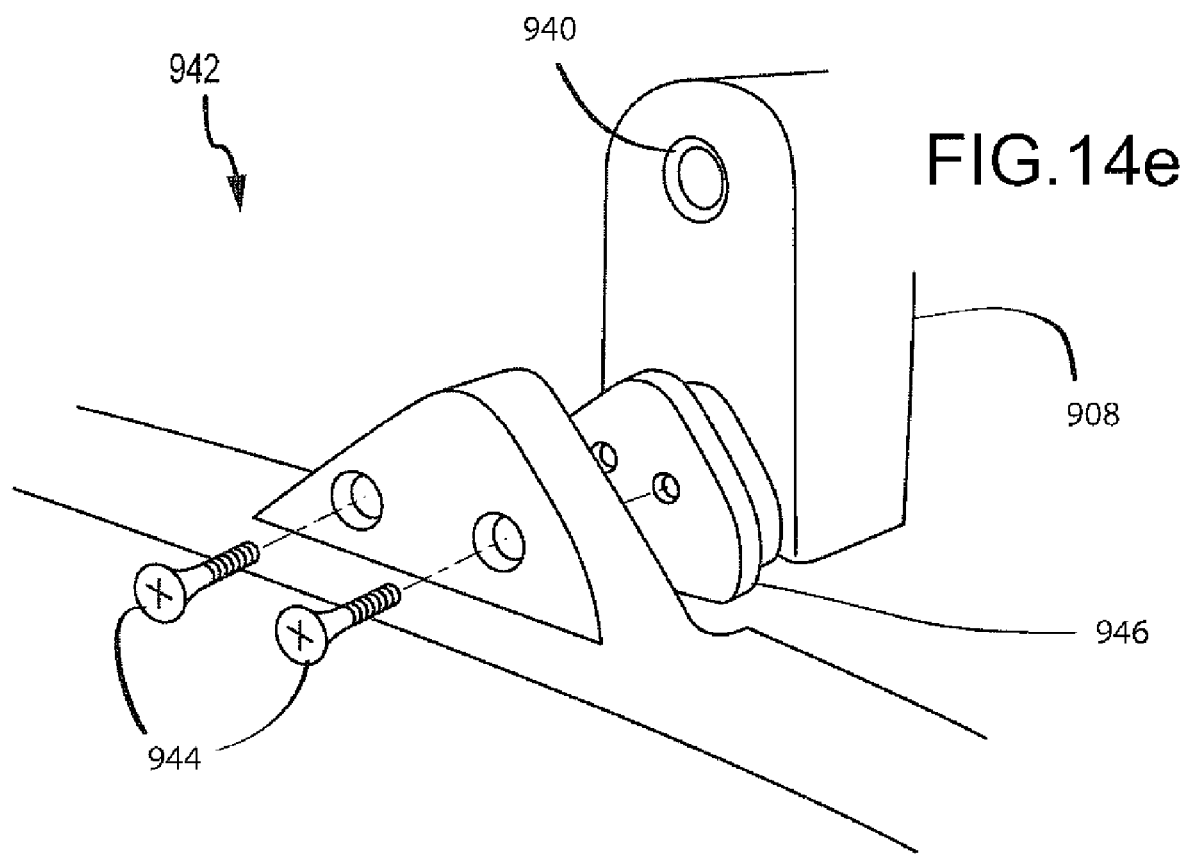
Figure 14F:
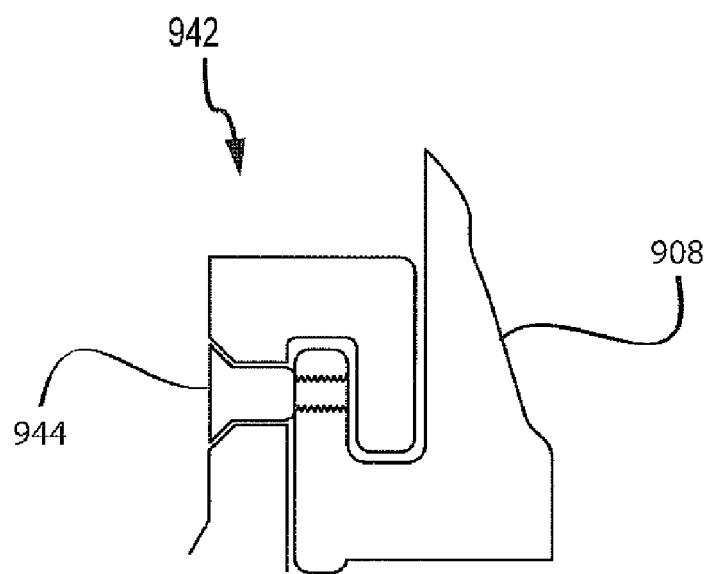

Referring to FIG. 14d, an enlarged view of manipulator assembly 300 of FIG. 1 is illustrated. As shown in FIG. 14d, manipulator assembly 300 including sterile cover 910 may further include power on/off switches 924, 926, and an emergency power switch 928. The manipulator and cartridge electrical/control connections may be provided at 930, 932. A handle 934 may be used to maneuver manipulator assembly 300 as needed. Appropriate LEDs 936, 938 may be provided for indicating proper connection of the catheter and sheath cartridges. As shown in FIGS. 14d-14f, manipulator assembly 300 may be pivotally connected to support linkages 908 at pivot point 940 by a two point rigid connection 942 including fasteners 944 and washer/aligner 946.

Referring to FIGS. 14a-14c and 14g-14j, for the ninth embodiment of manipulator support structure 900, cartridges 400 may include a cut-out 950 sized for a resistance snap-fit onto detent 952 of a manipulation base. A release button 954 may be provided for release of the cartridges from manipulator assembly 300. As shown in FIG. 14g, cartridges 400 may include a flexible connection for the catheter/sheath at strain relief connection 956, and electrical connection 968. As shown in FIG. 14h, an ergonomic grip area 958 may be provided for facilitating attachment, detachment and grasp of the cartridges. Referring to FIG. 14i, each cartridge may include a guide keel 960 including control pin slots 962 and control detent 964 engageable with respective detents and slots in the manipulation base (see FIG. 14g). Further, as shown in FIG. 14j, a sterile cap 966 may be provided for storage and transport of the cartridges, and removal of the cap for use. Those skilled in the art would readily appreciate in view of this disclosure that the cartridge designs of FIGS. 14g-14j may be utilized in combination with any of the other manipulator assemblies and sub-components disclosed herein, or in the above-identified commonly owned and copending applications.

Based on the discussion above, the aforementioned articulated support structures may hold manipulator assembly 300 in a position to better facilitate treatment or therapy (e.g., adjacent the femoral vein/artery to promote catheterization). Such support structures discussed in reference to FIGS. 2a-14j may, without limitation, include joints that may include a gas or hydraulic assist on each joint, and may further include a braking mechanism to decelerate or lock any moving component in place. The gas-hydraulic assist mechanisms may be provided on all joints to aid in vertical or other motion of the manipulator assembly. Additionally, electronic or electromechanical braking may be provided on all joints and at all degrees of freedom. The brake(s) may be configured to default to a locked state so that power is needed to enable any motion. A normally-locked configuration may be provided so that momentary power loss will not cause any unlocking or joint movement. The system may also be designed with sufficient stability to prevent movement, even under minor impacts.

Figure 15A:
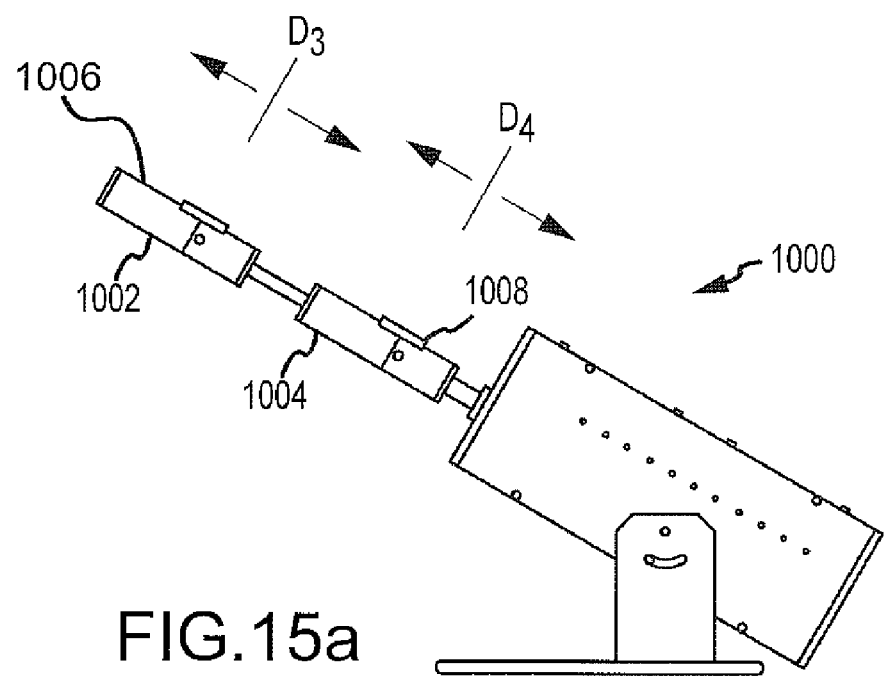
FIGS. 15a and 15b are exemplary joysticks usable with the robotic catheter system of FIG. 1.
Figure 15B:
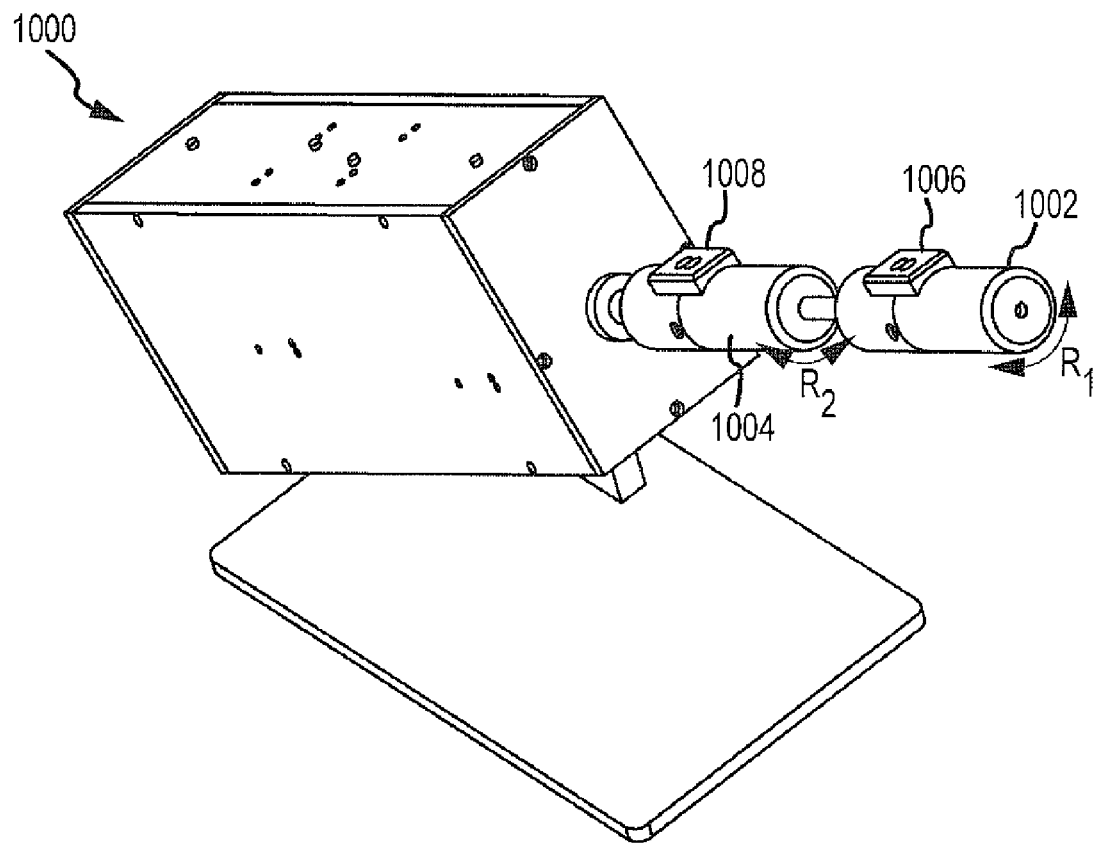

Referring to FIGS. 1, 15a and 15b, for input control system 100 discussed in greater detail in commonly owned and copending applications titled "Robotic Catheter System Input Device" and "Robotic Catheter System with Dynamic Response," an exemplary joystick usable with robotic catheter system 10 of FIG. 1 is disclosed.

Specifically, an embodiment of robotic catheter system 10 can include a user interface device 1000. For some embodiments such a device may be analogous to a joystick—allowing a user to provide input to the system in a manner mimicking traditional catheter handle controls. As generally shown in FIGS. 15a and 15b, an embodiment of the system may provide instrumented sheath and catheter handles 1002, 1004 (or vice-versa), respectively, that are able to longitudinally translate (e.g., in directions $D_3$ and $D_4$), independently rotate (in directions $R_1$ and $R_2$), and/or include one or more movable thumb tabs (e.g., elements 1006, 1008). To record the user's input, each degree of movement may be instrumented, for example, with a potentiometer or motor/encoder.

Mimicking traditional, manual catheter control, an embodiment of robotic catheter system 10 may be configured such that longitudinally translating the input handle may cause a respective longitudinal translation of the catheter/sheath distal tip. However, unlike the traditional, manual catheter, the automated catheter system would generally effectuate this translation by advancing or retracting the cartridge. Further, robotic catheter system 10 can be configured so that the rotation of either handle causes a virtual rotation of the catheter/sheath tip, and movement of a thumb tab causes a deflection in the current deflection plane.

In an embodiment of user interface device 1000, any or all motion controls of the device can be associated with/employ a spring centering feature that returns each control element to a set or "home" location after the element is released. Such a centering feature can allow for highly precise movement corrections of the distal tip by registering various input movements as incremental movement from the "home" location rather than by registering movement entirely in absolute terms.

In an embodiment, instead of thumb tab-type controls, user interface device 1000 may additionally include or substitute displacement dial controls. Furthermore, to suit the desires of the user, an embodiment of such a user interface device may permit the handles to be fully interchangeable so that various combinations of controls (e.g., dial and thumb tab handles) can be used for catheter/sheath input. In another embodiment, user interface device 1000 may further include safety buttons (e.g. "dead-man switches") that must be pressed for any joystick movement to be registered by the system. This design would prevent inadvertent motion from affecting the position of the actual catheter tip. In yet another embodiment, user interface device 1000 may further include a virtual reality surgical system, wherein the physician could be positioned within a cardiac environment (see FIG. 1), and physically position the catheter where desired or needed.

Figure 16A:
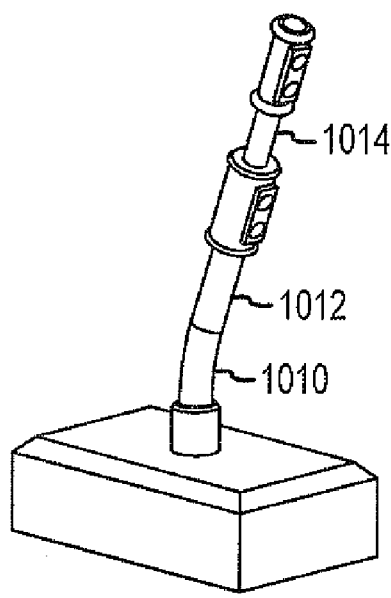
FIGS. 16a-16e are views of an exemplary construction of the joysticks of FIGS. 14a and 14b.
Figure 16B:
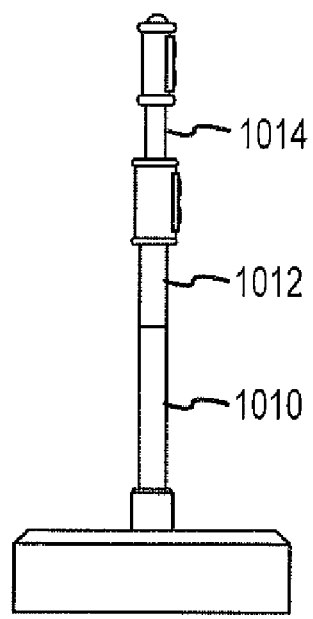
Figure 16C:
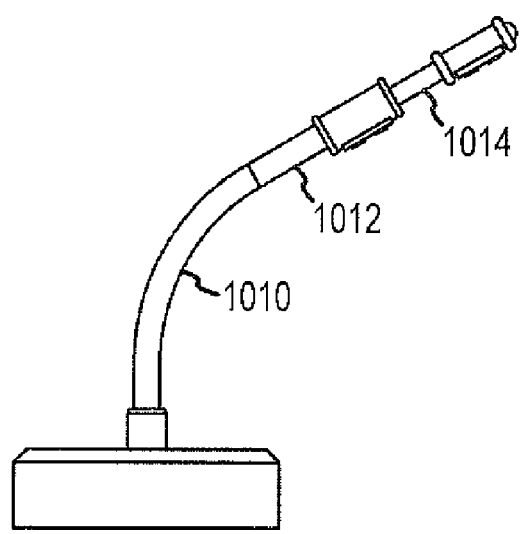
Figure 16D:
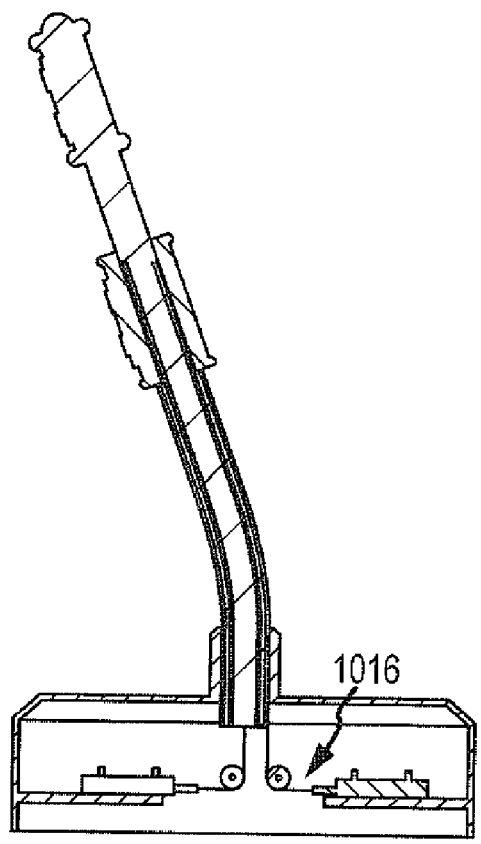
Figure 16E:
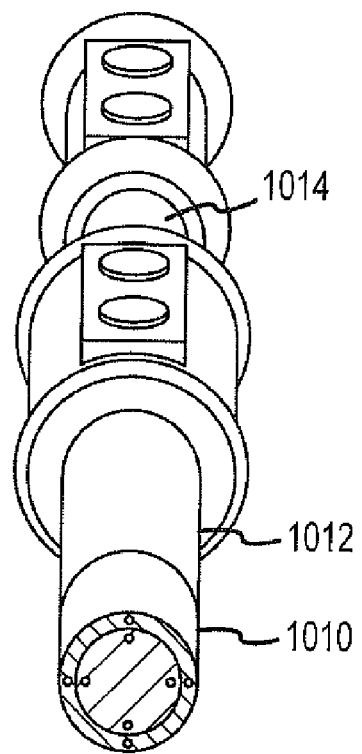

As generally shown in FIGS. 16a-16e, the physical construction of such a device for user interface device 1000 may be similar to that of an actual catheter, though on a different scale. As shown in FIGS. 16d and 16e, by way of example, the various sections may be constructed with pull wires, wire ducts, and variable stiffness sections 1010, 1012, 1014 associated with a conventional catheter. In an embodiment, all motions of this device may be configured with a centering feature (e.g., a spring centering mechanism 1016), wherein the device inherently returns to an initial position when released. This configuration may be useful or suitable for an incremental input control scheme.

In other embodiments, the device may be constructed without a centering mechanism, where the absolute position of the device might instead be used to control the absolute position of the actual sheath and catheter. With such an absolute approach, the input device's physical limitations may be designed to mimic an actual catheter's and sheath's physical limitations (e.g., movement restrictions based on bend radius, catheter retracted into sheath, etc.).

To record user input, each degree of movement can generally be instrumented with either a potentiometer or motor/encoder. If a motor/encoder is used, the system may also provide haptic feedback upon certain events—such as a "feel" if the catheter were to contact a virtual wall. An embodiment of this invention may also include an ablation activation button on the distal end of the device.

A user interface device in the form of an instrumented glove will now be discussed.

For some embodiments of robotic catheter system 10, user interface device 1000 may include or take the form of an instrumented glove. In an embodiment, the user's/wearer's index finger may be instrumented to act as a virtual catheter tip. In another embodiment, the user may have the ability to manipulate the actual catheter tip by interacting with a virtual representation of the tip. For such a user interface device, the user may wear a glove instrumented with sensors (such as accelerometers and position sensors). This device may then manipulate or interact with a 3-dimensional visualization of the catheter and/or heart anatomy, for instance, through holographic imagery.

In an embodiment of such an input control means, a remote control "glove-type" system may be further implemented within a liquid tank (e.g., water tank), where field generators (such as those associated with the NavX™ control system marketed by St. Jude Medical) are externally attached. For such embodiments, an instrumented glove may extend into the tank while a user's finger (e.g., index finger) or other portions of the glove are instrumented with electrodes to enable detection of position and orientation information for the entire glove or portions of the glove.

In an embodiment, electrodes (e.g., NavX-type electrodes) may be positioned on a user's index finger to correspond with similar electrodes on the catheter, where a movement of the glove electrodes can be configured to cause a corresponding movement of the actual catheter electrodes. Further, if desired, an incremental movement control scheme may be implemented by incorporating an activation switch, such as, for example, a foot pedal. Such a control/switch may indicate to the system that successive movements should be recorded for later use (e.g., for the purpose of control).

Haptic feedback based on actual sensed forces on a distal catheter tip will now be discussed.

An embodiment of user interface device 1000 may include touch-type feedback, often referred to as "haptic feedback," which may involve forces generated by a motor connected to user interface device 1000 that the user can feel while holding the device, also disclosed in commonly owned and copending application titled "Robotic Catheter System including Haptic Feedback," incorporated by reference in its entirety. These forces may be based on actual or computed forces being applied to a physical catheter tip. In an embodiment, the unit may sense forces using a force and/or impedance sensor in the tip of the catheter and generate a corresponding force on an input handle. In other embodiments, the forces can be based on a computed geometric model of the cardiac anatomy, such as that associated with the St. Jude Medical, Inc. EnSite™ system.

In an embodiment, haptic feedback may be conveyed to a user by employing an input device instrumented with motors/encoders on each degree of freedom. Though the motors may operate in a passive mode for a majority of the procedure, if feedback is required by the system, the motors may be energized to produce a torque on the input controls capable of retarding the user's movement in particular degrees of freedom. While in a passive mode, the motor typically will not produce a significant retarding force, however the attached encoder may record the input for use in visualization and control routines.

Prior to a haptic response being conveyed, the system may first calculate the appropriateness and magnitude of such a force. In an embodiment, such a force may attempt to replicate a contact between an actual catheter tip and a portion of the cardiac anatomy. In an embodiment, such contact may be either directly sensed through one or more force sensors on the distal tip of the catheter/sheath, or may be calculated based on a virtual catheter/sheath position within a rendered geometric computer model.

In an embodiment where haptic forces are based on actual catheter contact, the catheter's distal tip may be instrumented with a force sensor. Such a force sensor may include, without limitation, load cells, shape memory alloy based force sensors, piezoelectric force sensors, strain gauges, or optical-based or acoustic-based force sensors. In other embodiments, a contact sensor may be based on electrical contact, such as those associated with detected impedance.

In an embodiment employing actual contact sensing, the sensor may generate a signal representative of the actual physical or electrical contact. Based on the magnitude and direction of the force, as well as the current position of the input device, the system may produce a corresponding torque on the input device that may resist further movement through the obstructing anatomy. The system can be configured so that the user would "feel" this reaction force as if the input device was impacting a "virtual wall."

Based on the system calibration, the resistive force the user feels at the input joystick could be more or less "spongy." That is, the system could be tuned so that a tip impact with the cardiac wall is either felt like a rigid impact with an immovable object, or perhaps as a contact with a soft sponge.

Haptic feedback based on virtual catheter tip proximity to virtual cardiac anatomy will now be discussed.

As discussed above, in an embodiment, haptic feedback forces may be conveyed to a user based on contact forces computed from the proximity between a virtual catheter model and a computer-generated representation of the cardiac anatomy. In an embodiment, the catheter positioning may be obtained through an impedance-based position detection system (e.g., such as associated with St. Jude Medical's NaVX™ system). Further such a computer-generated representation of the cardiac anatomy may be derived from prior CT or MRI data, or a model (such as that created or maintained by St. Jude Medical's EnSite™ system).

With such embodiments/configurations, a user may have a previously obtained geometric model of the cardiac anatomy. This model may be visible to an EP user through a visualization system (such as St. Jude Medical's EnSite™ system). This model may be assembled using, for example, previously captured CT or MRI images, and/or "skinned" geometry obtained by sensing actual position data of a mapping catheter (e.g., with St Jude Medical's NavX™ system). Once the model is assembled, a catheter locating system (e.g., St. Jude Medical's NavX™ System) could then place the working catheter inside the computed geometric model. In an embodiment, as the catheter is moved within the geometry, a haptic system could be used to compare the positioning of the catheter to that of the generated geometry. If the catheter is perceived to be in contact with the generated geometry, a resistive force could then be generated in connection with the associated input device—e.g., using attached motors.

In an embodiment, the geometric model may be registered to a repeating physiological signal such as, for example, the cardiac rhythm or respiration rhythm. As this signal is sensed in the actual procedure, the model geometry may dynamically change. This may then enable computed haptic feedback to provide a more accurate representation of the contact actually occurring within the patient.

Figure 17:
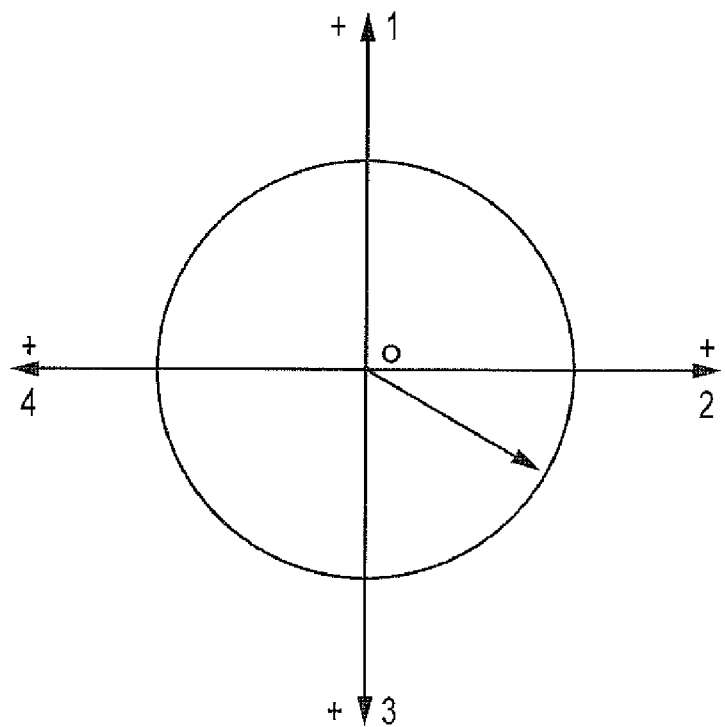
FIG. 17 is a graph of catheter deflection as a function of steering wire tension.

Referring to FIG. 17, orientation vector display in visualization software to show direction of thumb switch deflection will now be discussed.

With some traditional, non-robotic catheter procedures, a thumb switch on the catheter handle causes catheter deflection by tensioning a corresponding steering wire. Such a switch typically allows the distal tip of a catheter to laterally deflect in one of two opposing directions in a single plane. If deflection is desired in more than one plane, a user commonly must physically rotate the catheter about its longitudinal axis to cause the deflection plane to rotate.

Unlike traditional non-robotic controls, robotic catheter system 10 does not require physical rotation of the catheter to achieve a similar positioning result. The system instead can achieve 360-degree movement of the distal tip through the use of four (or more) steering wires (except when using a rotatable cartridge as discussed in commonly owned and copending application titled "Robotic Catheter Rotatable Device Cartridge"). In an embodiment, each of four steering wires is equally spaced around the catheter's/sheath's circumference (e.g., positioned 90 degrees apart). In an embodiment incorporating instrumented traditional catheter handle input controls, as described above, an indicator (see exemplary arrow in FIG. 17) is provided to give the user an idea of which direction the distal tip will deflect if the thumb switch is actuated.

An embodiment of robotic catheter system 10 provides an indication of the deflection direction by including a representation (e.g., a deflection plane vector) on a computer visualization (e.g., a display such as provided in connection with St. Jude Medical's EnSite™ system). In an embodiment, such a representation (e.g., vector) may include an arrow superimposed near the tip of the virtual representation of a physical catheter. Such an arrow may indicate the direction the catheter would move if the thumb switch were pulled toward the user. Similarly, pushing a control (e.g., thumb switch) may cause the catheter to deflect in the opposite, arrow tail direction. The user may then cause a rotation of this vector by rotating an input handle, which may then be sensed by the attached motor/encoder or potentiometer. Similarly, a deflection vector could be associated with sheath visualization.

Active tensioning of "passive" steering wires will now be briefly discussed with reference to FIGS. 5a-5e (as discussed above) and 18.

Figure 18:
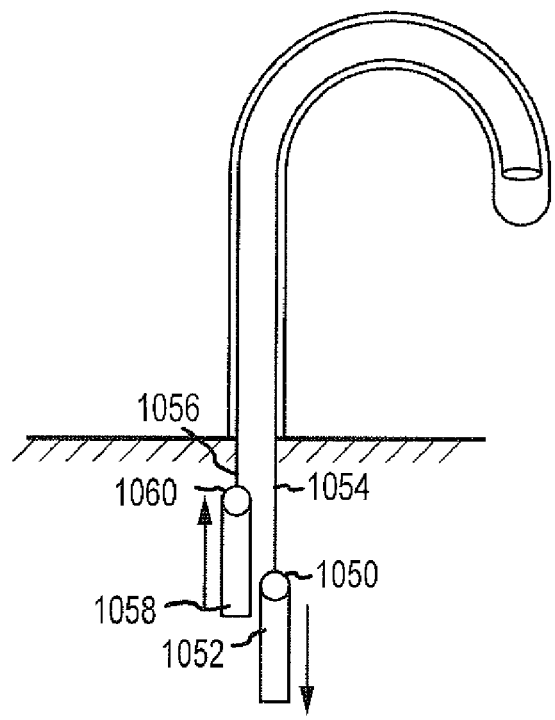
FIG. 18 is an exemplary view of steering wire movement for a two-wire catheter.

An embodiment of robotic catheter system 10 employs a plurality (e.g., four) independently-controlled steering wires to permit 360 degrees of deflection of a catheter tip. As generally shown in FIG. 18, a four wire embodiment provides that, for any given motion, either one or two (of the plurality) of adjacent steering wires may be tensioned in a proximal direction to cause a desired distal tip deflection. By selectively controlling which steering wires are tensioned, the automated catheter system has the ability to obtain 360 degrees of distal tip deflection without requiring physical rotation of the catheter about its shaft longitudinal axis.

As generally illustrated in FIG. 18 using a simplified, two-wire catheter, during any deflection, the steering wires not being directly tensioned (the "passive" steering wires) may tend to retract in a distal direction.

As described above, an embodiment of robotic catheter system 10 may provide for tensioning of the steering wires (e.g., by moving fingers/slider blocks in a proximal direction). As generally shown in FIG. 18, active manipulator finger 1050 pushes slider block 1052 in a proximal direction. This motion causes the attached steering wire 1054 to tension, resulting in a distal deflection of the catheter tip. To allow the displacement, steering wire 1056 must move in a distal direction due, in part, to the radius of curvature of the catheter bend. This causes the attached slider block 1058 to be pulled in a distal direction. In an embodiment, the manipulator fingers are not allowed to freely move due to their mechanical mounting (e.g., on a high-precision drive mechanism). To then allow the passive slider block 1058 to move distally, manipulator finger 1060 may be compelled to move in a distal direction.

In an embodiment, to help prevent fingers 1060 from impeding passive steering wires 1056, each finger may be retracted to a "home" position when it is not controllably tensioning a steering wire. Such a return-to-home configuration can, at least in part, help ensure that each finger 1060 will not obstruct the distal motion of passive slider blocks 1058. It may be desirable, however, for such a configuration to include features to address issues associated with reduced system response time and potential step-wise distal tip motion, attributable to the time needed to move fingers 1060 back into contact with slider-blocks 1058 when the passive slider blocks must be tensioned to cause a desired movement.

In another embodiment, passive slider blocks 1058 may be allowed to freely retract yet avoid contact latencies by incorporating a force sensor in mechanical communication each manipulator finger 1060. In such an embodiment, each passive finger 1060 may be controllably positioned such that a minimal contact force between finger 1060 and the passive steering wire slider block 1058 is always maintained. This ensures that all passive steering wires 1056 are maintained in a "ready" state yet are not significantly impeded. Such "active tensioning" may involve a closed loop algorithm that constantly monitors the force exerted on each finger 1060 through the use of, for example, strain gauges. The "active tensioning" control routine then may translate corresponding passive fingers 1060, by actuating a connected drive mechanism, to maintain contact force between finger 1060 and slider block 1058 within a bounded range (e.g., 50-100 grams of force).

Figure 19:
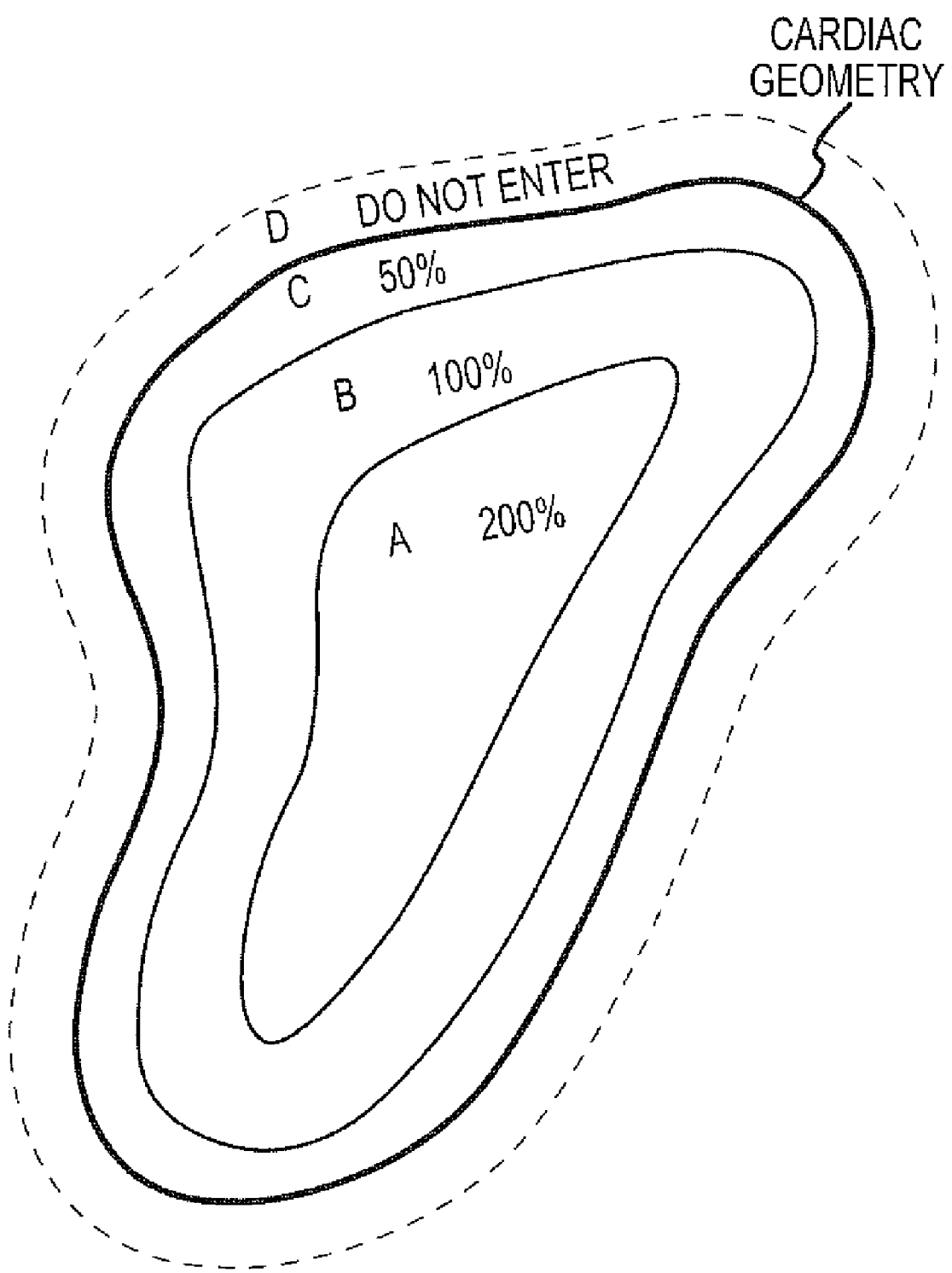
FIG. 19 is an exemplary view of speed-zones for optimizing movement of a catheter tip.

Pre-defined catheter "speed zones" will now be briefly discussed with reference to FIG. 19.

To aid users in navigating a catheter safely, yet quickly, around a cardiac chamber, robotic catheter system 10 may employ pre-defined "speed zones" to optimize the movement of the catheter tip. As described in relation to FIG. 19, zone A may be defined as the most central, and safest area in the cardiac chamber. In zone A, the catheter tip could be sped up so that the catheter tip can traverse this area at a faster than normal rate, e.g., 200% of the input motion. As the user moves the catheter closer to the cardiac wall, he/she may desire enhanced precision rather than speed. Therefore, zones B and C may purposefully and gradually reduce the scaling factor between input motion and tip movement. Finally, the user may have the ability to define a region exterior to the geometry, e.g., zone D, into which the catheter is prevented from entering. Alternatively, this "exterior zone" may be modeled to provide a force that would "push" the catheter back into the acceptable area.

If desired, the system may include a corresponding haptic response in the input joystick. For zones A, B, and C, such a haptic response may involve changing the dampening force on the handle (e.g., as the tip moves closer to the wall, the user might feel as if the tip is caught in an increasingly dense sludge). Once the tip starts to cross the barrier between zone C and zone D, this feeling may be accompanied by a force that prevents inadvertent continued motion.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A robotic catheter system comprising:
   a robotic catheter manipulator assembly comprising:
      a support member having a longitudinal axis and comprising a catheter manipulation base configured for linear movement along the longitudinal axis of the support member and a sheath manipulation base configured for linear movement along the longitudinal axis of the support member;

a robotic catheter device cartridge removably mounted to the catheter manipulation base, wherein the robotic catheter device cartridge is configured to be generally linearly movable relative to the support member along the longitudinal axis of the support member; and a robotic sheath device cartridge removably mounted to the sheath manipulation base, wherein the robotic sheath device cartridge is generally linearly movable relative to the support member along the longitudinal axis of the support member;

wherein at least one of the robotic catheter device cartridge and the robotic sheath device cartridge comprises a locking pin or recess and at least one of the catheter manipulation base and the sheath manipulation base comprises a complementary locking pin or recess to secure at least one of the robotic catheter device cartridge to the catheter manipulation base and the robotic sheath device cartridge to the sheath manipulation base;

an input control system for controlling operation of the robotic catheter manipulator assembly; and a visualization system including at least one display monitor for displaying a position of at least one of a catheter attached to the robotic catheter device cartridge and a sheath attached to the robotic sheath device cartridge.

2. The robotic catheter system according to claim 1, further comprising a manipulator support structure configured to support the robotic catheter manipulator assembly, wherein the manipulator support structure includes an attachment assembly for attaching the robotic catheter manipulator assembly to an operation bed.

3. The robotic catheter system according to claim 1, further comprising a manipulator support structure configured to support the robotic catheter manipulator assembly, wherein the manipulator support structure includes at least one retractable wheel for facilitating transport of the robotic catheter manipulator assembly.

4. The robotic catheter system according to claim 1, further comprising a manipulator support structure configured to support the robotic catheter manipulator assembly, wherein the manipulator support structure includes at least one support arm for adjustably supporting the robotic catheter manipulator assembly.

5. The robotic catheter system according to claim 4, wherein the support arm adjustably positions the robotic catheter manipulator assembly in a plane disposed at an acute angle relative to a generally horizontally disposed operation bed.

6. The robotic catheter system according to claim 4, wherein the support arm adjustably positions the robotic catheter manipulator assembly in a plane disposed generally orthogonal to a generally horizontally disposed operation bed.

7. The robotic catheter system according to claim 4, wherein the support arm adjustably positions the robotic catheter device cartridge and the robotic sheath device cartridge for movement in a plane disposed at an acute angle relative to a generally horizontally disposed operation bed.

8. The robotic catheter system according to claim 4, wherein the support arm adjustably positions the robotic catheter device cartridge and the robotic sheath device cartridge for movement in a plane disposed generally orthogonal to a generally horizontally disposed operation bed.

9. The robotic catheter system according to claim 1, wherein the robotic catheter manipulator assembly support structure is substantially fixedly disposed relative to an operation bed.

10. The robotic catheter system according to claim 1, further comprising a case for transport and sterile use of the robotic catheter manipulator assembly.

11. The robotic catheter system according to claim 1, further comprising a sterile shield for preventing contamination of the robotic catheter manipulator assembly.

12. The robotic catheter system according to claim 1, wherein the robotic catheter system is portable without lifting.

13. The robotic catheter system according to claim 1, wherein at least one of the robotic catheter device cartridge and the robotic sheath device cartridge is rotatable relative to the robotic catheter manipulator assembly.

14. The robotic catheter system according to claim 1, wherein the catheter manipulation base and the sheath manipulation base are movable relative to each other.

15. The robotic catheter system according to claim 1, wherein one of the catheter manipulation base and the robotic catheter device cartridge includes at least one first element engageable with at least one complementary second element of the other one of the catheter manipulation base and the robotic catheter device cartridge, wherein linear movement of one of the first element and the second element is configured to cause corresponding linear movement of the other one of the first element and the second element and control deflection of the catheter by pulling a steering wire attached to the catheter and one of the first element and the second element.

16. The robotic catheter system according to claim 1, wherein one of the sheath manipulation base and the robotic sheath device cartridge includes at least one first element engageable with at least one complementary second element of the other one of the sheath manipulation base and the robotic sheath device cartridge, wherein linear movement of one of the first element and the second element is configured to cause corresponding linear movement of the other one of the first element and the second element and control deflection of the sheath by pulling a steering wire attached to the sheath and one of the first element and the second element.

17. The robotic catheter system according to claim 1, wherein the catheter manipulation base is disposed generally behind the sheath manipulation base to allow insertion of the catheter into the sheath.

18. The robotic catheter system according to claim 1, wherein the input control system includes at least one of a joystick, an instrumented glove, a mouse, a space-ball and a 3D input device.

19. The robotic catheter system according to claim 1, wherein the input control system includes haptic feedback based on one of actual sensed forces on a distal catheter tip, and impedance measured from the distal catheter tip.

20. The robotic catheter system according to claim 1, wherein the input control system includes haptic feedback based on virtual catheter tip proximity to virtual cardiac anatomy.

21. The robotic catheter system according to claim 1, wherein the visualization system includes an orientation vector display for showing direction of a thumb switch deflection for the input control system.

22. The robotic catheter system according to claim 1, wherein the input control system includes active tensioning of steering wires attached to the catheter and sheath.

23. The robotic catheter system according to claim 1, wherein the input control system includes pre-defined speed zones for varying speed of movement of the catheter and sheath in predetermined areas in the anatomy of a patient.

24. A robotic catheter system comprising:
a robotic manipulator assembly comprising:
   a support member having a longitudinal axis and comprising a first surgical instrument manipulation base configured for linear movement along the longitudinal axis of the support member and a second surgical instrument manipulation base configured for linear movement along the longitudinal axis of the support member;
   at least one robotic first surgical instrument device cartridge removably mounted to the first surgical instrument manipulation base, wherein the robotic first surgical instrument device cartridge is configured to be generally linearly movable relative to the support member along the longitudinal axis of the support member; and
   at least one robotic second surgical instrument device cartridge removably mounted to the second surgical instrument manipulation base, wherein the robotic second surgical instrument device cartridge is generally linearly movable relative to the support member along the longitudinal axis of the support member;
   wherein at least one of the robotic first surgical instrument device cartridge and the robotic second surgical instrument device cartridge comprises a locking pin or recess and at least one of the first surgical instrument manipulation base and the second surgical instrument manipulation base comprises a complementary locking pin or recess to secure at least one of the first surgical instrument device cartridge to the first surgical instrument manipulation base and the second surgical instrument device cartridge to the second surgical instrument manipulation base;
an input control system for controlling operation of the robotic manipulator assembly; and
a visualization system including at least one display for displaying a position of at least one of a first surgical instrument attached to the robotic first surgical instrument device cartridge and a second surgical instrument attached to the robotic second surgical instrument device cartridge.

25. The robotic catheter system according to claim 24, further comprising a manipulator support structure configured to support the robotic manipulator assembly, wherein the manipulator support structure includes an attachment assembly for attaching the robotic manipulator assembly to an operation bed.

26. The robotic catheter system according to claim 24, further comprising a manipulator support structure configured to support the robotic manipulator assembly, wherein the manipulator support structure includes at least one retractable wheel for facilitating transport of the robotic manipulator assembly.

27. The robotic catheter system according to claim 24, further comprising a manipulator support structure configured to support the robotic manipulator assembly, wherein the manipulator support structure includes at least one support arm for adjustably supporting the robotic manipulator assembly.

28. The robotic catheter system according to claim 27, wherein the support arm adjustably positions the robotic manipulator assembly in a plane disposed at an acute angle relative to a generally horizontally disposed operation bed.

29. The robotic catheter system according to claim 27, wherein the support arm adjustably positions the robotic manipulator assembly in a plane disposed generally orthogonal to a generally horizontally disposed operation bed.

30. The robotic catheter system according to claim 27, wherein the support arm adjustably positions the robotic first surgical instrument device cartridge and the second surgical instrument device cartridge for movement in a plane disposed at an acute angle relative to a generally horizontally disposed operation bed.

31. The robotic catheter system according to claim 27, wherein the support arm adjustably positions the robotic first surgical instrument device cartridge and the second surgical instrument device cartridge for movement in a plane disposed generally orthogonal to a generally horizontally disposed operation bed.

32. The robotic catheter system according to claim 24, wherein the robotic manipulator assembly support structure is substantially fixedly disposed relative to an operation bed.

33. The robotic catheter system according to claim 24, further comprising a case for transport and sterile use of the robotic manipulator assembly.

34. The robotic catheter system according to claim 24, further comprising a sterile shield for preventing contamination of the robotic manipulator assembly.

35. The robotic catheter system according to claim 24, wherein the robotic catheter system is portable without lifting.

36. The robotic catheter system according to claim 24, wherein at least one of the first surgical instrument device cartridge and the second surgical instrument device cartridge is rotatable relative to the robotic manipulator assembly.

37. The robotic catheter system according to claim 24, wherein the first surgical instrument manipulation base and the at least one second surgical instrument manipulation base are movable relative to each other.

38. The robotic catheter system according to claim 24, wherein one of the first surgical instrument manipulation base and the first surgical instrument device cartridge includes at least one first element engageable with at least one complementary second element of the other one of the first surgical instrument manipulation base and the robotic first surgical instrument device cartridge, wherein linear movement of one of the first element and the second element is configured to cause corresponding linear movement of the other one of the first element and the second element and control deflection of the first surgical instrument by pulling a steering wire attached to the first surgical instrument and one of the first element and the second element.

39. The robotic catheter system according to claim 24, wherein one of the second surgical instrument manipulation base and the robotic second surgical instrument device cartridge includes at least one first element engageable with at least one complementary second element of the other one of the second surgical instrument manipulation base and the robotic second surgical instrument device cartridge, wherein linear movement of one of the first element and the second element is configured to cause corresponding linear movement of the other one of the first element and the second element and control deflection of the second surgical instrument by pulling a steering wire attached to the second surgical instrument and one of the first element and the second element.

40. The robotic catheter system according to claim 24, wherein the first surgical instrument manipulation base is disposed generally behind the second surgical instrument manipulation base to allow insertion of the first surgical instrument into the second surgical instrument.

41. The robotic catheter system according to claim 24, wherein the input control system includes at least one of a joystick, an instrumented glove, a mouse, a space-ball and a 3D input device.

42. The robotic catheter system according to claim 24, wherein the input control system includes haptic feedback based on one of actual sensed forces on a distal first surgical instrument tip, and impedance measured from the distal first surgical instrument tip.

43. The robotic catheter system according to claim 24, wherein the input control system includes haptic feedback based on virtual first surgical instrument tip proximity to virtual cardiac anatomy.

44. The robotic catheter system according to claim 24, wherein the visualization system includes an orientation vector display for showing direction of a thumb switch deflection for the input control system.

45. The robotic catheter system according to claim 24, wherein the input control system includes active tensioning of steering wires attached to the first surgical instrument and the second surgical instrument.

46. The robotic catheter system according to claim 24, wherein the input control system includes pre-defined speed zones for varying speed of movement of the first surgical instrument and the second surgical instrument in predetermined areas in the anatomy of a patient.

47. The robotic catheter system according to claim 24, wherein the first surgical instrument and the second surgical instrument are each one of a transseptal needle, a catheter and a sheath.

48. The robotic catheter system according to claim 24, further comprising a manipulator support structure configured to support the robotic manipulator assembly, wherein the manipulator support structure is an integrated system including a RF generator, a saline pump and saline bags.

49. The robotic catheter system according to claim 24, wherein the robotic manipulator assembly includes a cartridge override for at least one of preventing and disabling movement of at least one of the robotic first surgical instrument device cartridge and the robotic second surgical instrument device cartridge.

50. A robotic catheter system comprising:
a robotic catheter manipulator assembly comprising:
a support member having a longitudinal axis and comprising a catheter manipulation base configured for linear movement along the longitudinal axis of the support member and a sheath manipulation base configured for linear movement along the longitudinal axis of the support member, wherein the catheter manipulation base and the sheath manipulation base have respective ranges of linear movement along the longitudinal axis of the support member that at least partially overlap;
a robotic catheter device cartridge removably mounted to the catheter manipulation base, wherein the robotic catheter device cartridge is configured to be generally linearly movable relative to the support member along the longitudinal axis of the support member; and
a robotic sheath device cartridge removably mounted to the sheath manipulation base, wherein the robotic sheath device cartridge is generally linearly movable relative to the support member along the longitudinal axis of the support member;
an input control system for controlling operation of the robotic catheter manipulator assembly; and
a visualization system including at least one display monitor for displaying a position of at least one of a catheter attached to the robotic catheter device cartridge and a sheath attached to the robotic sheath device cartridge.

51. The robotic catheter system of claim 50, wherein the respective ranges of linear movement along the longitudinal axis of the support member each have a length of approximately 8 inches.

* * * * *